United States Patent [19]
Haviv et al.

[11] Patent Number: 5,981,521
[45] Date of Patent: Nov. 9, 1999

[54] TETRAHYDROISOQUINOLINE DERIVATIVES AS LHRH ANTAGONISTS

[75] Inventors: Fortuna Haviv, Deerfield; Wesley J. Dwight, Evanston; Bradley W. Crawford, Gurnee; Rolf E. Swenson, Lawrenceville; Milan Bruncko, Lake Bluff; Michele A. Kaminski, Beach Park; Lisa M. Frey, Mundelein; John DeMattei, Gurnee; Jonathan Greer, Chicago, all of Ill.

[73] Assignee: Abbott Laboratories, Abbott Park, Ill.

[21] Appl. No.: 09/191,511

[22] Filed: Nov. 13, 1998

[51] Int. Cl.$^6$ .......................... C07D 217/04; A61K 31/47
[52] U.S. Cl. .......................... 514/213; 514/307; 540/576; 546/149
[58] Field of Search .................. 546/149; 540/576; 514/213, 307

[56] References Cited

U.S. PATENT DOCUMENTS

| | | | |
|---|---|---|---|
| 5,110,904 | 5/1992 | Haviv et al. | 530/313 |
| 5,140,009 | 8/1992 | Haviv et al. | 514/16 |
| 5,502,035 | 3/1996 | Haviv et al. | 514/15 |

FOREIGN PATENT DOCUMENTS

| | | |
|---|---|---|
| 0187700 | 4/1990 | European Pat. Off. . |
| 0712845 | 5/1996 | European Pat. Off. . |
| 9529900 | 11/1995 | WIPO . |
| 9721704 | 6/1997 | WIPO . |

OTHER PUBLICATIONS

Science, vol. 202, (OCt. 1978), Andrew V. Schally, pp. 18–28, "Aspects of Hypothalamic Regulation of the Pituitary Gland".

*Primary Examiner*—Zinna Norhtington Davis
*Attorney, Agent, or Firm*—Portia Chen

[57] ABSTRACT

Tetrahydroisoquinoline derivatives of the formula:

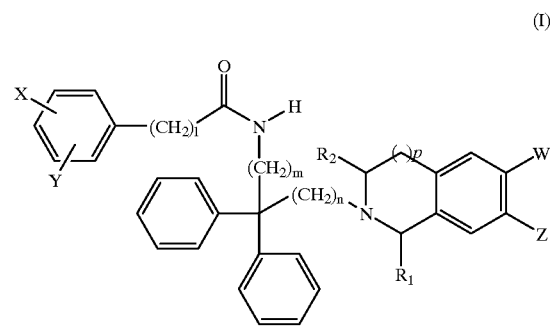

(I)

or a pharmaceutically acceptable salt, ester, or prodrug thereof, having activity as an LHRH antagonist, as well as pharmaceutical compositions containing the same, and methods for their use and preparation.

20 Claims, No Drawings

TETRAHYDROISOQUINOLINE DERIVATIVES AS LHRH ANTAGONISTS

TECHNICAL FIELD OF THE INVENTION

The present invention relates to novel tetrahydroisoquinoline derivatives having activity as luteinizing hormone releasing hormone (LHRH) antagonists. In particular, the invention relates to pharmaceuticals containing these compounds, a process for making them, as well as a method for treating various hormone dependent diseases, including prostate cancer, endometriosis, uterine fibroids, precocious puberty, benign prostate hypertrophy, and in vitro fertilization.

BACKGROUND OF THE INVENTION

The gonadotropin hormones, luteinizing hormone (LH) and follicle-stimulating hormone (FSH) regulate the fundamental reproductive processes, such as ovarian release and gamete maturation. LHRH released from the hypothalamus binds to a receptor on the pituitary gland causing the release of gonadotropin hormones. The ongoing system of feedback plays a major role in regulating the synthesis of the steroidal reproductive hormones from the gonads. ie. estrogen and progesterone in females and testosterone in males. Consequently, controlling the pulsatile release of LHRH provides an avenue for the design of novel compounds useful in treating various conditions related to dysfunction of the reproductive cycle and hormone dependent diseases.

Natural mammalian releasing hormone LHRH isolated and purified from porcine and human hypothalamus has been characterized as having the sequence:

(pyro)Glu-His-Trp-Ser-Tyr-Gly-Leu-Arg-Pro-Gly-$NH_2$ as described in A. V. Schally, *Science*, 202:6 (1978). Substitutions and derivatizations of amino acyl residues have been developed to achieve novel compounds useful in treating various disorders related to mammalian reproductive systems. Some derivatives of natural compounds have been shown to exhibit activity as LHRH agonists or as antagonists of LHRH.

Synthetic analogs evidencing activity in modulating LHRH secretion typically comprise peptides of naturally-occurring or non-naturally occurring amino acid residues. Peptide LHRH antagonists characterized by substitution of the nitrogen atom of at least one amide bond are described in U.S. Pat. No. 5,110,904, and U.S. Pat. No. 5,502,035.

Truncated peptide compounds developed as a series of smaller peptide analogs also exhibit biological activity and afford the added advantage of possibly improving oral bioavailability. "Pseudo" peptide compounds, see for example U.S. Pat. No. 5,140,009, are recognized LHRH antagonists. Reduced-size pentapeptides LHRH antagonists are described in pending U.S. application Ser. No. 132,999. Pending application U.S. Ser. No. 133,055 discloses heptapeptide analogs which provide active compounds truncated from the C-terminus of a decapeptide antagonist sequence.

Non-peptide heterocyclic reproductive hormone regulators have been reported in the literature, see for example, WO 95/29900 and WO 97/21704. Macrolide LHRH antagonists are described in the pending U.S. application Ser. No. 049,963; see also pending U.S. application Ser. No. 140,805. European Patent EP 0712845 discloses amine compounds exhibiting LHRH receptor antagonist activity; see also European Patent EP 0187700.

The non-peptide LHRH antagonists of the present invention comprise tetrahydro- isoquinoline derivatives not previously described by the prior art. The compounds are useful in the treating a variety of sex hormone related conditions including precocious puberty, benign prostatic hyperplasia, breast and ovarian tumors, prostate tumors, cryptorchidism, hirsutism in women, gastric motility disorders, dysmenorrhea and endometriosis.

SUMMARY OF THE INVENTION

In one aspect, the present invention relates to a compound having the formula:

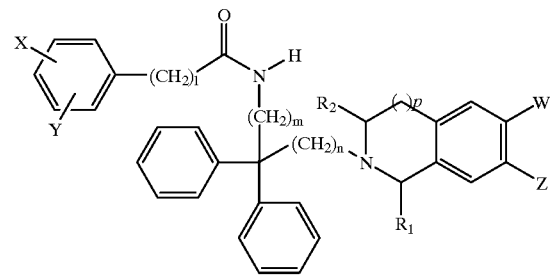

(I)

or a pharmaceutically acceptable salt, ester, or prodrug thereof, wherein:

l, m, and n are each independently 1, 2, 3, or 4;
p is I or 2;
$R_1$ is selected from the group consisting of:
(a) alkyl,
(b) cycloalkyl,
(c) aryl,
(d) cyano,
(e) —$(CH_2)_q$—$R_4$, wherein q is 0 to 10,
(f) -cycloalkyl-$R_5$, and
(g) -aryl-$R_5$;
$R_2$ is selected from the group consisting of:
(a) alkyl,
(b) hydrogen,
(c) alkoxycarbonyl,
(d) hydroxymethyl, and
(e) —$(CH_2)_q$—$R_4$, wherein q is 0 to 10;
$R_4$ is selected from the group consisting of:
(a) alkyl,
(b) alkoxy,
(c) aryl,
(d) aryloxy,
(e) cyano,
(f) cycloalkyl,
(g) hydroxy,
(h) halogen,
(i) phthalimido,
(j) -cycloalkyl-$R_5$,
(k) -aryl-$R_5$, and
(l) -$NR_6R_7$;
$R_5$ is selected from the group consisting of:
(a) alkyl,
(b) alkoxy,
(c) cyano,
(d) hydroxy,
(e) halogen, (f) trifluoromethyl, and (g) —(CH$_2$)$_q$—NR$_6$R$_7$, wherein q is 0 to 10;

R$_6$ and R$_7$ are independently selected from the group consisting of:

(a) hydrogen, (b) alkyl, (c) cycloalkyl, and (d) aryl, or

R$_6$ is hydrogen and R$_7$ is a group of the formula —COR$_8$, wherein R$_8$ is selected from the group consisting of:

(a) alkyl, (b) aryl, and (c) heterocycle;

X and Y are independently selected from the group consisting of:

(a) hydrogen, (b) halogen, (c) alkoxy, (d) alkyl, and (e) trifluoromethyl; and

W and Z are independently selected from the group consisting of:

(a) hydrogen, (b) hydroxy, (c) alkyl, (d) alkoxy, (e) alkoxycarbonyl, (f) nitro, (g) N-acyl, (h) halogen, and (i) trifluoromethyl, or W and Z taken together form a cyclic ring.

The compounds of the invention bind to LHRH receptors and are effective LHRH antagonists. Compounds within the scope of the invention are effective in the treatment of prostate cancer, endometriosis. precocious puberty and other types of diseases which are related to sex hormones.

In another aspect, the invention relates to a process of preparing a compound of the invention comprising treating a diphenyl-substituted aminoalkanol with an activated carboxylic acid to obtain an N-substituted aminoalkanol, oxidizing alcohol moiety of the N-substituted aminoalkanol to an aldehyde moiety, and alkylating the aldehyde moiety with a tetrahydroisoquinoline ring to afford a tetrahydroisoquinoline derivative of formula (I).

Another aspect of the invention relates to pharmaceutical compositions which are useful as LHRH antagonists and modulating levels of sex hormones in mammals.

Yet another aspect of the invention relates to a method of modulating levels of sex hormones in male and female mammals comprising admininstering to a host in need of such treatment a therapeutically effective amount of an LHRH compound of the invention.

DETAILED DESCRIPTION OF THE INVENTION

The terms "alkyl" and "lower alkyl" as used herein refer to straight or branched chain alkyl radicals containing from 1 to 10 carbon atoms, sometimes represented as Cx-Cy-alkyl where x and y respectively represent the minimum and maximum number of carbon atoms in the alkyl radical. Examples of lower alkyl include, but are not limited to, methyl, ethyl, n-propyl, isopropyl, n-butyl, isobutyl, sec-butyl, t-butyl, n-pentyl, 1-methylbutyl, 2,2-dimethylbutyl, 2-methylpentyl, 2,2-dimethylpropyl, n-hexyl, n-octyl, n-nonyl, n-decyl, and the like.

The term "alkoxy" as used herein refers to a lower alkyl group of one to three carbons, as defined above, which is bonded to an oxygen atom in an ether linkage. Examples of alkoxy groups include, but are not limited to, methoxy, ethoxy, isopropoxy, n-pentyloxy, t-butoxy, n-octyloxy and the like. This alkoxy radical can also contain a ring which includes, but is not limited to, a five or six atom ring composed of carbons, and up to one or two heteroatoms such as nitrogen, oxygen, or sulfur.

The term "alkoxycarbonyl" as used herein refers to an alkoxy group as described above wherein an oxygen atom is linked to the parent molecular moiety via a carbonyl group.

The term "cyclic ring" as used herein refers to hydrocarbon chain of one to four carbon atoms carbon-carbon bonded to $\alpha,\beta$-adjacent carbons on the parent molecular moiety or respectively linked by an ether linkage at the $\alpha$- or $\beta$- carbon, for example, acetonido.

The term "cycloalkyl" as used herein refers to a saturated monocyclic hydrocarbon groups having from three to six carbon atoms in the ring, including, but not limited to, cyclopropyl, cyclobutyl, cyclopentyl, cyclohexyl, cycloheptyl and the like. The cyclic group may be optionally substituted with, for example, alkyl, alkoxy, cyano, hydroxy, halogen, trifluoromethyl, amino, or N-substituted aminoalkyl. The cycloalkyl may be carbon-carbon bonded directly to the parent molecular moiety or linked to the parent molecule via an appended substituent.

The term "aryl" as used herein refers to a mono-, fused bicyclic or fused tricyclic carbocyclic ring system having one or more aromatic rings including, but not limited to, phenyl, naphthyl, tetrahydronaphthyl, phenanthrenyl, biphenylenyl, indanyl, indenyl and the like. The term "bicyclic aryl" as used herein includes naphthyl, tetrahydronaphthyl, indanyl, indenyl and the like. The term "tricyclic aryl" as used herein includes anthracenyl, phenanthrenyl, biphenylenyl, fluorenyl, and the like. Aryl groups (including bicyclic and tricyclic aryl groups) can be unsubstituted or substituted with one, two or three substituents independently selected from lower alkyl, haloalkyl, alkoxy, thioalkoxy, amino, N-substituted aminoalkyl, alkenyloxy, hydroxy, halo, mercapto, nitro, carboxaldehyde, carboxy, alkoxycarbonyl and alkylamido. Substituents also include methylenedioxy and ethylenedioxy. In addition, substituted aryl groups include tetrafluorophenyl and pentafluorophenyl. Aryl and substituted aryl groups may be carbon-carbon bonded directly to the parent molecular moiety or linked to the parent molecule via an appended substituent.

The term "aryloxy" as used herein refers to an aryl group as described above wherein the aryl group is linked to the parent molecular moiety -ia an oxygen atom in an ether linkage.

The terms "heterocyclic ring" or "heterocyclic" or "heterocycle" as used herein refers to any 3- or 4-membered ring containing a heteroatom selected from oxygen, nitrogen and sulfur. or a 5-, 6- or 7-membered ring containing one, two or three nitrogen atoms, one nitrogen and one sulfur atom, or one nitrogen and one oxygen atom. The 5-membered ring has 0–2 double bonds and the 6- and 7-membered ring have 0–3 double bonds. The nitrogen heteroatoms can be optionally quatemized. The term "heterocyclic" also includes bicyclic groups in which any of the above heterocyclic rings is fused to a benzene ring or a cyclohexane ring or another heterocyclic ring (for example, indolyl, quinolyl, isoquinolyl, tetrahydroquinolyl, decahydroquinolyl, benzofuryl or benzothienyl, imidazopyridyl, pyrrolopyridyl and the like). The term "heterocyclic" also includes tricyclic groups in which any of the above heterocyclic rings is fused to two benzene rings or two cyclohexane rings or two other heterocyclic rings (for example, carbazolyl, iminodibenzyl and the like). Heterocyclics include: azetidinyl; benzimidazolyl; 1,4-benzodioxanyl 1 .3-benzodioxolyl; benzoxazolyl; benzothiazolyl; benzothienyl; carbazolyl; dihydropyranyl; dihydrofuranyl; dioxanyl; dioxolanyl; furyl; homopiperidinyl; imidazolyl; imidazolinyl; imidazolidinyl; imidazopyridyl; iminodibenzyl; indolinyl; indolyl; isoquinolinyl; isothiazolidinyl; isothiazolyl; isoxazolidinyl; isoxazolyl; morpholinyl; naphthyridinyl; oxazolidinyl; oxazolyl; piperazinyl; piperidinyl; pyranyl; pyrazinyl; pyrazolidinyl; pyrazolinyl; pyrazolyl; pyridazinyl; pyridyl; pyrimidinyl; pyrrolidinyl; pyrrolindinylpyridyl; pyrrolinyl; pyrrolopyridyl; pyrrolyl; quinolinyl; tetrahydrofuranyl; tetrahydropyranyl; thiazolidinyl; thiazolyl; and thienyl.

Heterocycles can be unsubstituted or monosubstituted or disubstituted with substituents independently selected from hydroxy, halo, oxo (=O), alkylimino (R*N=wherein R* is a loweralkyl group), amino, N-substituted aminoalkyl, alkoxy, alkoxyalkoxy, haloalkyl, cycloalkyl, aryl, arylalkyl, —COOH, —SO$_3$H and loweralkyl. In addition, nitrogen containing heterocycles can be N-protected.

The term "hydroxymethyl" as used herein refers to a lower alkyl of one to ten carbon atoms substituted at one or more carbon atoms with a hydroxy group.

The term "N-acyl" as used herein refers to an N-substituted aminoalkyl group wherein the nitrogen atom is linked to the parent molecular moiety via a carbonyl group. The term "N-substituted aminoalkyl" refers to an amino group substituted with one, two or three lower alkyl groups of one to ten carbons, for example, ethylamino, butylamino, and the like. Amino groups which are substituted with two or three lower alkyl groups as defined above, include for example, diethylamino, methyl propylamino, and the like. The lower alkyl groups are optionally substituted with, for example, alkoxy, aryl, substituted aryl, carbonyl, cycloalkyl, hydroxy, halogen or amino. Exemplary N-acyl groups include, but are not limited to, methylcarbamoyl, 1-cyclopentyl ethylcarbamoyl, and the like.

The term "pharmaceutically acceptable salts" as used herein refers to those carboxylate salts, esters, and prodrugs of the compound of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible. of the compounds of the invention. Pharmaceutically acceptable salts are well known in the art and refer to the relatively non-toxic, inorganic and organic acid addition salts of the compound of the present invention. For example, S. M. Berge, et al. describe pharmaceutically acceptable salts in detail in *J. Pharmaceutical Sciences*, 66: 1–19 (1977) which is incorporated herein by reference. The salts can be prepared in situ during the final isolation and purification of the compounds of the invention, or separately by reacting, the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuiwc acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, palmoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

The term "pharmaceutically acceptable esters" as used herein refers to non-toxic esters of the compounds of this invention. Examples of pharmaceutically acceptable esters include $C_1$ to $C_6$ alkanoyl esters wherein the alkanoyl group is a straight or branched chain. Esters of the compounds of the present invention may be prepared according to conventional methods.

The term "pharmaceutically acceptable prodrugs" as used herein refers to those prodrugs of the compounds of the present invention which are, within the scope of sound medical judgment, suitable for use in contact with the tissues of humans and lower animals without undue toxicity, irritation, allergic response. and the like, commensurate with a reasonable benefit/risk ratio. and effective for their intended use, as well as the zwitterionic forms. where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, *Pro-drugs as Novel Delivery Systems,* Vol. 14 of the A.C.S. Symposium Series. and in Edward B. Roche, ed., *Bioreversible Carriers in Drug Design,* American Pharmaceutical Association and Pergamon Press. 1987, both of which are incorporated herein by reference.

Where appropriate, prodrugs of derivatives of compounds of the present invention may be prepared by any suitable method. For those compounds in which the prodrug moiety is an amino acid or peptide functionality, the condensation of the amino group with amino acids and peptides may be effected in accordance with conventional condensation methods such as the azide method, the mixed acid anhydride method, the DCC (dicyclohexylcarbodiimide) method, the active ester method (p-nitrophenyl ester method, N-hydroxysuccinic acid imide ester method, cyanomethyl ester method and the like), the Woodward reagent K method, the DCC-HOBT (1-hydroxybenzotriazole) method and the like. Classical methods for amino acid condensation reactions are described in M. Bodansky, Y. S. Klausner and M. A. Ondetti, *Peptide Synthesis,* Second Edition, NY, 1976, which is incorporated herein by reference.

Numerous asymmetric centers may exist in the compounds of the present invention. Except where otherwise noted, the present invention contemplate the various stereoisomers and mixtures thereof. Accordingly, whenever a bond is represented by a wavy line, it is intended that a mixture of stereo-orientations or an individual isomer of assigned or unassigned orientation may be present.

Preferred Embodiment

Preferred compounds of the invention are those compounds of formula (I) wherein l is 2, m is 3, n is 3, and p is 1.

Additional preferred compounds of the invention are compounds represented by the formula (I) wherein $R_1$ is selected from the group consisting of alkyl, cycloalkyl, and —$(CH_2)_q$—$R_4$, wherein q is 0 to 10, and $R_4$ is a group of the formula —$NR_6R_7$, wherein $R_6$ and $R_7$ are each independently selected from hydrogen, alkyl, and cycloalkyl.

Preferred compounds of the invention are also include compounds of formula (I) wherein $R_2$ is selected from the group consisting of hydrogen and methyl.

Other preferred compounds of the invention are those compounds represented by the formula (I) wherein X and Y are independently selected from the group consisting of hydrogen and halogen.

Additional preferred compounds of the invention are compounds of formula (I) wherein W and Z are independently selected from the group consisting of hydrogen and methoxy.

The more preferred compounds of the invention are those compounds as represented by formula (I) wherein $R_1$ is selected from the group consisting of methyl, cyclopropyl, cyclobutyl, aminomethyl, aminoethyl, aminopropyl, aminobutyl, N-[cyclopropylmethyl]aminobutyl, and N-[bis-cyclopropylmethyl]-aminobutyl.

Representative compounds within the scope of the invention are selected from the group consisting of:

(R,S) 7-[N-3-(4-fluorophenyl)propionyl]amino-1-[N-(1,2,3,4-tetrahydro-1-methyl-6,7-dimethoxyisoquinolinyl)]-4,4-diphenylheptane hydrochloride;

(R) 7-[N-3-(4-fluorophenyl)propionyl]amino-1-[N-(1,2,3,4-tetrahydro-1-methyl-6,7-dimethoxyisoquinolinyl)]-4,4-diphenylheptane hydrochloride;

(S) 7-[N-3-(4-fluorophenyl)propionyl]amino-1-[N-(1,2,3,4-tetrahydro-1-methyl-6,7-dimethoxyisoquinolinyl)]-4,4-diphenylheptane hydrochloride;

7-[N-3-(4-fluorophenyl)propionyl]amino-1-[N-(1,2,3,4-tetrahydro-1-cyclopropyl-6,7-dimethoxyisoquinolinyl)]-4,4-diphenylheptane hydrochloride;

7-[N-3-(4-fluorophenyl)propionyl]amino-1-[N-(1,2,3,4-tetrahydro-1-ethyl-6,7-dimethoxy-isoquinolinyl)]-4,4-diphenylheptane hydrochloride;

7-[N-3-(4-fluorophenyl)propionyl]amino-1-[N-(1,2,3,4-tetrahydro-1-isopropyl-6,7-dimethoxyisoquinolinyl)]-4,4-diphenylheptane hydrochloride;

7-[N-3-(4-fluorophenyl)propionyl]amino-1-[N-(1,2,3,4-tetrahydro-1-phenyl-6,7-dimethoxy-isoquinolinyl)]-4,4-diphenylheptane hydrochloride;

7-[N-3-(4-fluorophenyl)propionyl]amino-1-[N-(1,2,3,4-tetrahydro-1-cyclopentyl-6,7-dimethoxyisoquinolinyl)]-4,4-diphenylheptane hydrochloride;

7-[N-3-(4-fluorophenyl)propionyl]amino-1-[N-(1,2,3,4-tetrahydro-1-cyclobutyl-6,7-dimethoxyisoquinolinyl)]-4,4-diphenylheptane hydrochloride;

7-[N-3-(4-fluorophenyl)propionyl]amino-1-[N-(1,2,3,4-tetrahydro-1-cyclohexyl-6,7-dimethoxyisoquinolinyl)]-4,4-diphenylheptane hydrochloride;

7-[N-(4-fluorophenyl)propionyl]amino-1-[N-(1,2,3,4-tetrahydro-1-cyanomethyl-6,7-dimethoxyisoquinolinyl)]-4,4-diphenylheptane hydrochloride;

7-[N-(4-fluorophenyl)propionyl]amino-1-[N-(1,2,3,4-tetrahydro-1-methoxymethyl-6,7-dimethoxyisoquinolinyl)]-4.4-diphenylheptane hydrochloride;

7-[N-3-(4-fluorophenyl)propionyl]amino-1-[N-(1,2,3,4-tetrahydro-1-benzyloxymethyl-6,7-dimethoxyisoquinolinyl)]-4.4-diphenylheptane hydrochloride;

7-[N-3-(4-fluorophenyl)propionyl]amino-1-[N-(1,2,3,4-tetrahydro-1-(p-methoxy)phenyl-6,7-dimethoxyisoquinolinyl)]-4,4-diphenylheptane hydrochloride;

7-[N-3-(4-fluorophenyl)propionyl]amino-1-[N-(1,2,3,4-tetrahydro-1-(4-aminophenyl)-6,7-dimethoxyisoquinolinyl)]-4,4-diphenylheptane dihydrochloride;

7-[N-3-(4-fluorophenyl)propionyl]amino-1-[N-(1,2,3,4-tetrahydro-1-[4-(N-isopropyl-amino)phenyl]-6,7-dimethoxyisoquinolinyl)]-4,4-diphenylheptane dihydrochloride;

7-[N-3-(4-fluorophenyl)propionyl]amino-1-[N-(1,2,3,4-tetrahydro-1-benzyl-6,7-dimethoxy-isoquinolinyl)]-4,4-diphenylheptane hydrochloride;

7-[N-3-(4-fluorophenyl)propionyl]amino-1-[N-(1,2,3,4-tetrahydro-1-(4-chlorobenzyl)-6,7-dimethoxyisoquinolinyl)]-4,4-diphenylheptane hydrochloride;

7-[N-3-(4-fluorophenyl)propionyl]amino 1-[N-(1,2,3,4-tetrahydro-1-(4-methoxybenzyl)-6,7-dimethoxyisoquinolinyl)]-4,4-diphenylheptane hydrochloride;

7-[N-3-(4-fluorophenyl)propionyl]amino 1-[N-(1,2,3,4-tetrahydro-1-phenethyl-6,7-di-methoxyisoquinolinyl)]-4,4-diphenylheptane hydrochloride;

7-[N-3-(4-fluorophenyl)propionyl]amino-1-[N-(1,2,3,4-tetrahydro-1-(4-aminobenzyl)-6,7-dimethoxyisoquinolinyl)]-4,4-diphenylheptane dihydrochloride;

7-[N-3-(4-fluorophenyl)propionyl]amino 1-[N-(1,2,3,4-tetrahydro-1-aminomethyl-6,7-di-methoxyisoquinolinyl)]-4,4-diphenylheptane dihydrochloride;

7-[N-3-(4-fluorophenyl)propionyl]amino-1-[N-(1,2,3,4-tetrahydro-1-(N-isopropyl-aminomethyl)-6,7-dimethoxyisoquinolinyl)]-4,4-diphenylheptane dihydrochloride;

7-[N-3-(4-fluorophenyl)propionyl]amino-1-[N-(1,2,3,4-tetrahydro-1-(4-N-phthalimido-butyl)-6,7-dimethoxyisoquinolinyl)]-4,4-diphenylheptane hydrochloride;

7-[N-3-(4-fluorophenyl)propionyl]amino-1-[N-(1,2,3,4-tetrahydro-1-(4-aminobutyl)-6,7-dimethoxyisoquinolinyl)]-4,4-diphenylheptane dihydrochloride;

7-[N-3-(4-fluorophenyl)propionyl]amino-1-[N-(1,2,3,4-tetrahydro-1-[4-(N-isopropyl-amino)butyl]-6,7-dimethoxyisoquinolinyl)]-4,4-diphenylheptane dihydrochloride;

7-[N-3-(4-fluorophenyl)propionyl]amino-1-[N-(1,2,3,4-tetrahydro-1-[4-(N-cyclopropyl-methylamino)butyl]-6,7-dimethoxyisoquinolinyl)]-4,4-diphenylheptane dihydrochloride;

7-[N_3-(4-fluorophenyl)propionyl]amino-1-[N-(1,2,3,4-tetrahydro-1-[4-(N-cyclobutyl-amino)butyl]-6,7-dimethoxyisoquinolinyl)]-4,4-diphenylheptane dihydrochloride;

7-[N-3-(4-fluorophenyl)propionyl]amino-1-[N-(1,2,3,4-tetrahydro-1-[4-(N-isobutyl-amino)butyl]-6,7-dimethoxyisoquinolinyl)]-4,4-diphenylheptane dihydrochloride;

7-[N-3-(4-fluorophenyl)propionyl]amino-1-[N-(1,2,3,4-tetrahydro-1-[4-(N-isopentyl-amino)butyl]-6,7-dimethoxyisoquinolinyl)]-4,4-diphenylheptane dihydrochloride;

7-[N-3-(4-fluorophenyl)propionyl]amino-1-[N-(1,2,3,4-tetrahydro-1-[4-(N-alpha-methyl-benzylamino)butyl]-6,7-dimethoxyisoquinolinyl)]-4,4-diphenylheptane dihydrochloride;

7-[N-3-(4-fluorophenyl)propionyl]amino-1-[N-(1,2,3,4-tetrahydro-1-[4-(N,N-dicyclopropyl-methylamino)butyl]-6,7-dimethoxyisoquinolinyl)]-4,4-diphenylheptane dihydrochloride;

7-[N-3-(4-fluorophenyl)propionyl]amino-1-[N-(1,2,3,4-tetrahydro-1-[4-(N,N-dimethyl-amino)butyl]-6,7-dimethoxyisoquinolinyl)]-4,4-diphenylheptane dihydrochloride;

7-[N-3-(4-fluorophenyl)propionyl]amino 1-[N-(1,2,3,4-tetrahydro-1-[4-(N-acetyl-amino)butyl]-6,7-dimethoxyisoquinolinyl)]-4,4-diphenylheptane hydrochloride;

7-[N-3-(4-fluorophenyl)propionyl]amino 1-[N-(1,2,3,4-tetrahydro-1-[4-(N-nicotinyl-amino)butyl]-6,7-dimethoxyisoquinolinyl]-4,4-diphenylheptane hydrochloride;

7-[N-3-(4-fluorophenyl)propionyl]amino-1-[N-(1,2,3,4-tetrahydro-1-[4-(N-phthalimido-methyl]cyclohexyl-6,7-dimethoxyisoquinolinyl)]-4,4-diphenylheptane hydrochloride;

7-[N-3-(4-fluorophenyl)propionyl]amino-1-[N-(1,2,3,4-tetrahydro-1-(4-aminomethyl-cyclohexyl)-6,7-dimethoxyisoquinolinyl)]-4,4-diphenylheptane dihydrochloride;

7-[N-3-(4-fluorophenyl)propionyl]amino 1-[N-(1,2,3,4-tetrahydro-1-(4-N-isopropylamino-methyl)cyclohexyl-6,7-dimethoxyisoquinolinyl)]-4,4-diphenylheptane dihydrochloride;

7-[N-3-(4-fluorophenyl)propionyl]amino-1-[N-(1,2,3,4-tetrahydro-1-(4-N-phthalimido-methyl)phenyl-6,7-dimethoxyisoquinolinyl)]-4,4-diphenylheptane hydrochloride;

7-[N-3-(4-fluorophenyl)propionyl]amino-1-[N-(1,2,3,4-tetrahydro-1-(4-aminomethyl-phenyl)-6,7-dimethoxyisoquinolinyl)]-4,4-diphenylheptane dihydrochloride;

7-[N-3-(4-fluorophenyl)propionyl]amino-1-[N-(1,2,3,4-tetrahydro-1-(4-N-isopropylamino-methyl)phenyl-6,7-dimethoxyisoquinolinyl)]-4,4-diphenylheptane dihydrochloride;

7-[N-3-(4-fluorophenyl)propionyl]amino-1-[N-(1,2,3,4-tetrahydro-1-(4-N-cyclobutylamino-methyl)phenyl-6,7-dimethoxyisoquinolinyl)]-4,4-diphenylheptane dihydrochloride;

7-[N-3-(4-fluorophenyl)propionyl]amino-1-[N-(1,2,3,4-tetrahydro-1-(4-N-cyclopropyl-methylaminomethyl)phenyl-6,7-dimethoxyisoquinolinyl)]-4,4-diphenylheptane dihydrochloride;

7-[N-3-(4-fluorophenyl)propionyl]amino-1-[N-(1,2,3,4-tetrahydro-1-(4-N-biscyclopropyl-methylaminomethyl)phenyl-6,7-dimethoxyisoquinolinyl)]-4.4-diphenylheptane dihydrochloride;

7-[N-3-(4-fluorophenyl)propionyl]amino-1-[N-(1,2,3,4-tetrahydro-1-(4-N-acetylamino-methyl)phenyl-6,7-dimethoxyisoquinolinyl)]-4,4-diphenylheptane hydrochloride;

7-[N-3-(4-fluorophenyl)propionyl]amino-1-[N-(1,2,3,4-tetrahydro-1-methyl-6,7-dihydroxy-isoquinolinyl)]-4.4-diphenylheptane hydrochloride;

7-[N-3-(4-fluorophenyl)propionyl]amino-1-[N-(1,2,3,4-tetrahydro-1-methylisoquinolinyl)]-4,4-diphenylheptane hydrochloride;

7-[N-3-(4-fluorophenyl)propionyl]amino-1-[N-(1,2,3,4-tetrahydro-1-methyl-6,7-dioxalane-isoquinolinyl)]-4,4-diphenylheptane hydrochloride;

7-[N-3-(4-fluorophenyl)propionyl]amino-1-[N-(1,2,3,4-tetrahydro-1-methyl-6,7-dioxane-isoquinolinyl)]-4,4-diphenylheptane hydrochloride;

7-[N-3-(4-fluorophenyl)propionyl]amino-1-[N-(1,2,3,4-tetrahydro-1-methyl-6-methoxy-isoquinolinyl)]-4,4-diphenylheptane hydrochloride;

7-[N-3-(4-fluorophenyl)propionyl]amino-1-[N-(1,2,3,4-tetrahydro-1-methyl-7-methoxy-isoquinolinyl)]-4,4-diphenylheptane hydrochloride;

7-[N-3-(4-fluorophenyl)propionyl]amino-1-[N-(1,2,3,4-tetrahydro-1-methyl-7-chloro-isoquinolinyl)]-4,4-diphenylheptane hydrochloride;

7-[N-3-(4-fluorophenyl)propionyl]amino-1-[N-(1,2,3,4-tetrahydro-1-methyl-7-fluoro-isoquinolinyl)]-4,4-diphenylheptane hydrochloride;

7-[N-3-(4-fluorophenyl)propionyl]amino-1-[N-(1,2,3,4-tetrahydro-1-methyl-7-nitro-isoquinolinyl)]-4,4-diphenylheptane hydrochloride;

7-[N-3-(4-fluorophenyl)propionyl]amino-1-[N-(1,2,3,4-tetrahydro-1-methyl-7-acetylamino-isoquinolinyl)]-4,4-diphenylheptane hydrochloride;

7-[N-3-(4-fluorophenyl)propionyl]amino-1-[N-(1,2,3,4-tetrahydro-1-methyl-6,7-dichloro-isoquinolinyl)]-4,4-diphenylheptane hydrochloride;

7-[N-3-(4-fluorophenyl)propionyl]amino-1-[N-(1,2,3,4-tetrahydro-1-methyl-6-chloro-7-fluoroisoquinolinyl)]-4,4-diphenylheptane hydrochloride;

7-[N-3-(4-fluorophenyl)propionyl]amino-1-[N-(1,2,3,4-tetrahydro-1-methyl-6,7-diacetoxy-isoquinolinyl)]-4,4-diphenylheptane hydrochloride;

7-[N-3-(4-fluorophenyl)propionyl]amino-1-[N-(1,2,3,4-tetrahydro-1-methyl-6-bromo-7-methoxyisoquinolinyl)]-4,4-diphenylheptane hydrochloride;

7-[N-3-(4-fluorophenyl)propionyl]amino-1-[N-(1.2,3,4-tetrahydro-1-methyl-6-fluoro-7-methoxyisoquinolinyl)]-4.4-diphenylheptane hydrochloride;

7-[N-3-(4-fluorophenyl)propionyl]amino-1-[N-(1,2,3,4-tetrahydro-1-methyl-6-methoxy-7-bromo-isoquinolinyl)]-4,4-diphenylheptane hydrochloride;

7-[N-3-(4-fluorophenyl)propionyl]amino-1-[N-(1,2,3,4-tetrahydro-1,6-dimethyl-7-methoxy-isoquinolinyl)]-4,4-diphenylheptane hydrochloride;

7-[N-3-(4-fluorophenyl)propionyl]amino-1-[N-(1,2,3,4-tetrahydro-1-methyl-6-carbo-methoxy-7-methoxyisoquinolinyl)]-4,4-diphenylheptane hydrochloride;

7-[N-3-(4-fluorophenyl)propionyl]amino-1-[N-(1,2,3,4-tetrahydro-1-cyclobutyl-6-bromo-7-methoxy-isoquinolinyl)]-4,4-diphenylheptane hydrochloride;

7-[N-3-(4-fluorophenyl)propionyl]amino-1-[N-(1,2,3,4-tetrahydro-1,3-dimethyl-6,7-di-methoxyisoquinolinyl)]-4,4-diphenylheptane hydrochloride;

7-[N-3-(4-fluorophenyl)propionyl]amino-1-[N-(1,2,3,4-tetrahydro-3-methyl-6,7-dimethoxy-isoquinolinyl)]-4,4-diphenylheptane hydrochloride;

7-[N-3-(4-fluorophenyl)propionyl]amino-1-[N-(1,2,3,4-tetrahydro-1,1-dimethyl-6,7-di-methoxyisoquinolinyl)]-4,4-diphenylheptane hydrochloride;

7-[N-3-(4-fluorophenyl)propionyl]amino-1-[N-(1,2,3,4-tetrahydro-1,3-dimethyl-7-methoxy-10 isoquinolinyl)]-4,4-diphenylheptane hydrochloride;

7-[N-3-(4-fluorophenyl)propionyl]-1-[N-(2,3,4,5-tetrahydro-1-methyl-7,8-dimethoxy-1H-2-benzazepinyl)]-4,4-diphenylheptane hydrochloride;

6-[N-3-(4-fluorophenyl)propionyl]amino-1-[N-(1,2,3,4-tetrahydro-1-methyl-6,7-methoxy-isoquinolinyl)]-3,3-diphenylhexane hydrochloride;

8-[N-3-(4-fluorophenyl)propionyl]amino 1-[N-(1,2,3,4-tetrahydro-1-methyl-6,7-di-methoxy-isoquinolinyl)]-5,5-diphenyloctane hydrochloride;

8-[N-3-(4-fluorophenyl)acetyl]amino-1-[N-(1,2,3,4-tetrahydro-1-methyl-6,7-dimethoxy-isoquinolinyl)]-5,5-diphenyloctane hydrochloride;

7-[N-3-(4-fluorophenyl)propionyl]amino-1-[N-(1,2,3,4-tetrahydro-1-methyl-7-methoxy-3-methoxycarbonylisoquinolinyl)]-4,4-diphenylheptane hydrochloride;

7-[N-3-(4-fluorophenyl)propionyl]amino 1-[N-(1,2,3,4-tetrahydro-3-(2-hydroxyethyl-aminocarbonyl)-1-methyl-7-methoxyisoquinolinyl)]-4,4-diphenylheptane hydrochloride;

7-[N-3-(4-fluorophenyl)propionyl]amino-1-[N-(1,2,3,4-tetrahydro-(3-hydroxypropyl-aminocarbonyl)-1-methyl-7-methoxyisoquinolinyl)]-4,4-diphenylheptane hydrochloride;

7-[N-3-(4-fluorophenyl)propionyl]amino-1-[N-(1,2,3,4-tetrahydro-3-(4-hydroxybutyl-aminocarbonyl)-1-methyl-7-methoxyisoquinolinyl)]-4,4-diphenylheptane hydrochloride;

7-[N-3-(4-fluorophenyl)propionyl]amino-1-[N-(1,2,3,4-tetrahydro-1-methyl-7-methoxy-3-(2-(N-pyrrolidinyl)ethylaminocarbonyl)isoquinolinyl)]-4,4-diphenylheptane hydrochloride;

7-[N-3-(4-fluorophenyl)propionyl]amino-1-[N-(1,2,3,4-tetrahydro-1-methyl-3-hydroxy-methyl-7-methoxyisoquinolinyl)]-4,4-diphenylheptane hydrochloride;

7-[N-3-(phenyl)propionyl]amino-1-[N-(1,2,3,4-tetrahydro-1-methyl-6,7-dimethoxy-isoquinolinyl)]-4,4-diphenylheptane hydrochloride;

7-[N-3-(3,4-dichlorophenyl)propionyl]amino-1-[N-(1,2,3,4-tetrahydro-1-methyl-6,7-dimethoxyisoquinolinyl)]-4,4-diphenylheptane hydrochloride;

7-[N-3-(3,4-difluorophenyl)propionyl]amino-1-[N-(1,2,3,4-tetrahydro-1-methyl-6,7-dimethoxyisoquinolinyl)]-4,4-diphenylheptane hydrochloride;

7-[N-3-(3-fluoro-4-chloro-phenyl)propionyl]amino-1-[N-(1,2,3,4-tetrahydro-1-methyl-6,7-dimethoxy-isoquinolinyl)]-4,4-diphenylheptane hydrochloride;

7-[N-3-(4-fluoro-3-chloro-phenyl)propionyl]amino-1-[N-(1,2,3,4-tetrahydro-1-methyl-6,7-dimethoxy-isoquinolinyl)]-4,4-diphenylheptane hydrochloride;

7-[N-3-(3,4-dimethoxyphenyl)propionyl]amino-1-[N-(1,2,3,4-tetrahydro-1-methyl-6,7-dimethoxyisoquinolinyl)]-4,4-diphenylheptane hydrochloride;

7-[N-3-(4-methoxyphenyl)propionyl]amino-1-[N-(1,2,3,4-tetrahydro-1-methyl-6,7-dimethoxyisoquinolinyl)]-4,4-diphenylheptane hydrochloride;

7-[N-3-(4-chlorophenyl)propionyl]amino-1-[N-(1,2,3,4-tetrahydro-1-methyl-6,7-dimethoxy-isoquinolinyl)]-4,4-diphenylheptane hydrochloride;

7-[N-3-(4-fluorophenyl)acetyl]amino-1-[N-(1,2,3,4-tetrahydro-1-methyl-6,7-dimethoxy-isoquinolinyl)]-4,4-diphenylheptane hydrochloride;

7-[N-3-(4-fluorophenyl)propionyl]amino-1-[N-(1,2,3,4-tetrahydro-1-(3-N-phthalimido-propyl)-6,7-dimethoxyisoquinolinyl)]-4,4-diphenylheptane hydrochloride;

7-[N-3-(4-fluorophenyl)propionyl]amino-1-[N-(1,2,3,4-tetrahydro-1-(3-aminopropyl)-6,7-dimethoxyisoquinolinyl)]-4,4-diphenylheptane hydrochloride;

7-[N-3-(4-fluorophenyl)propionyl]amino-1-[N-(1,2,3,4-tetrahydro-1-[3-N-(biscyclobutyl-amino)propyl]-6,7-dimethoxyisoquinolinyl)]-4,4-diphenylheptane dihydrochloride;

7-[N-3-(4-fluorophenyl)propionyl]amino-1-[N-(1,2,3,4-tetrahydro-1-[3-N-(biscyclopropyl-methylamino)propyl]-6.7-dimethoxyisoquinolinyl)]-4,4-diphenylheptane dihydrochloride;

7-[N-3-(4-fluorophenyl)propionyl]amino-1-[N-(1,2,3,4-tetrahydro-1-[3-N-(dimethylamino)-propyl]-6,7-dimethoxyisoquinolinyl)]-4,4-diphenylheptane dihydrochloride;

7-[N-3-(4-fluorophenyl)propionyl]amino-1-[N-(1,2,3,4-tetrahydro-1-[3-N-(isopropyl)propyl]-6,7-dimethoxyisoquinolinyl)]-4,4-diphenylheptane dihydrochloride;

7-[N-3-(4-fluorophenyl)propionyl]amino-1-[N-(1,2,3,4-tetrahydro-1-(5-N-phthalimido-pentyl)-6,7-dimethoxyisoquinolinyt)]-4,4-diphenylheptane hydrochloride;

7-[N-3-(4-fluorophenyl)propionyl]amino-1-[N-(1,2,3,4-tetrahydro-1-(5-aminopentyl)-6,7-dimethoxyisoquinolinyl)]-4,4-diphenylheptane dihydrochloride;

7-[N-3-(4-fluorophenyl)propionyl]amino-1-[N-(1,2,3,4-tetrahydro-1-[5-N-(biscyclobutyl-amino)pentyl]-6,7-dimethoxyisoquinolinyl)]-4.4-diphenylheptane dihydrochloride;

7-[N-3-(4-fluorophenyl)propionyl]amino-1-[N-(1,2,3,4-tetrahydro-1-[5-N-(biscyclopropyl-methylamino)pentyl]-6,7-dimethoxyisoquinolinyl)]-4,4-diphenylheptane dihydrochloride;

7-[N-3-(4-fluorophenyl)propionyl]amino-1-[N-(1,2,3,4-tetrahydro-1-[5-N-(dimethylamino)-pentyl]-6,7-dimethoxyisoquinolinyl)]-4,4-diphenylheptane dihydrochloride;

7-[N-3-(4-fluorophenyl)propionyl]amino-1-[N-(1,2,3,4-tetrahydro-1-[5-N-(isopropylamino)-pentyl]-6,7-dimethoxyisoquinolinyl)]-4,4-diphenylheptane dihydrochloride;

7-[N-3-(4-fluorophenyl)propionyl]amino-1-[N-(1,2,3,4-tetrahydro-1-cyclobutyl-6-fluoro-7-methoxyisoquinolinyl)]-4,4-diphenylheptane hydrochloride;

7-[N-3-(4-fluorophenyl)propionyl]amino-1-[N-(1,2,3,4-tetrahydro-1-(4-N-phthalimidobutyl)-6-methyl-7-methoxyisoquinolinyl)]-4,4-diphenylheptane hydrochloride;

7-[N-3-(4-fluorophenyl)propionyl]amino-1-[N-(1,2,3,4-tetrahydro-1-(4-aminobutyl)-6-methyl-7-methoxyisoquinolinyl)]-4,4-diphenylheptane dihydrochloride;

7-[N-3-(4-fluorophenyl)propionyl]amino-1-[N-(1,2,3,4-tetrahydro-1-(4-N-isopropylamino-butyl)-6-methyl-7-methoxyisoquinolinyl)]-4,4-diphenylheptane dihydrochloride; and 7-[N-3-(4-fluorophenyl)propionyl]amino-1-[N-(1,2,3,4-tetrahydro-1-cyclobutyl-6-methyl-7-methoxyisoquinolinyl)]-4,4-diphenylheptane hydrochloride.

Effects and Utilities of LHRH Antagonists

In practicing the method of the invention, a therapeutically effective amount of a compound of the invention or a pharmaceutical composition containing the same is administered to the human or animal in need of, or desiring, such treatment. The compound may be employed in pure form or, where such forms exist, in pharmaceutically acceptable salt, ester or prodrug form. By a "therapeutically effective amount" of the compound of the invention is meant a sufficient amount of the compound to treat the targeted disorder, at a reasonable benefit/risk ratio applicable to any medical treatment, which is administered in such quantities and over such a period of time as is necessary to obtain the desired therapeutic effect. It will be understood, however, that the total daily usage of the compounds and compositions of the present invention will be decided by the attending physician within the scope of sound medical judgment.

The specific therapeutically effective dose level for any particular patient will depend upon a variety of factors including the disorder being treated and the severity of the disorder; activity of the specific compound employed, the specific composition employed; the age. body weight, general health, sex and diet of the patient: the time of administration, route of administration and rate of excretion of the specific compound employed; the duration of the treatment; drugs used in combination or coincidental with the specific compound employed; and like factors well known in the medical arts. For example. it is well within the skill of the art to start doses of the compound at levels lower than required to achieve the desired therapeutic effect and to gradually increase the dosage until the desired effect is achieved.

The total daily dose of the compound of this invention administered to a human or lower animal may range from about 0.1 to about 100 mg/kg/day or for topical administration from about 0.1 to about 10% in cream, ointment or other topical formulation or for rectal or vaginal administration from about 10 to about 500 mg per dose in a suitable vehicle. For purposes of oral administration. doses may be in the range of from about 1 to about 100 mg/kg/day or, more preferably, of from about 10 to about 20 mg/kg/day. If desired, the effective daily dose may be divided into multiple doses for purposes of administration; consequently, single dose compositions may contain such amounts or submultiples thereof as make up the daily dose.

Compounds and pharmaceutical compositions of the invention may be administered by a variety of routes depending on the specific end use. Exemplary methods of administration include, but are not limited to, orally, rectally, parenterally, intracistemally, intravaginally, intraperitoneally, topically (as by powders, ointments, or drops), bucally, or as an oral or nasal spray. The term "parenteral" as used herein refers to modes of administration which include intravenous, intramuscular, intraperitoneal, intracisternal, subcutaneous and intraarticular injection and infusion.

The pharmaceutical compositions of the present invention comprise a compound of the invention in combination with a pharmaceutically acceptable carrier or excipient. The term "pharmaceutically acceptable carrier" refers to a non-toxic solid, semi-solid or liquid filler, diluent. encapsulating material or formulation auxiliary of any type.

Pharmaceutical compositions of this invention for parenteral injection include pharmaceutically acceptable sterile nonaqueous solutions or aqueous dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol. propylene glycol, polyethylene glycol. and the like), carboxymethylcellulose and suitable mixtures thereof. vegetable oils (such as olive oil), and injectable organic esters such as ethyl oleate. Proper fluidity can be maintained. for example, by the use of coating materials such as lecithin, by the maintenance of the required particle size in the case of dispersions, and by the use of surfactants.

These compositions may also contain adjuvants such as preservative, wetting agents, emulsifying agents. and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert. pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates. gelatin, polyvinylpyrrolidone, sucrose and acacia. c) humectants such as glycerol, d) disintegrating agents such as agar-agar, calcium carbonate. potato or tapioca starch, alginic acid, certain silicates and sodium carbonate, e) solution retarding agents such as paraffin, f) absorption accelerators such as quaternary ammonium compounds, g) wetting agents such as, for example. cetyl alcohol and glycerol monostearate. h) absorbents such as kaolin and bentonite clay, and i) lubricants such as talc, calcium stearate, magnesium stearate, solid polyethylene glycols and sodium lauryl sulfate, and mixtures thereof. In the case of capsules, tablets and pills, the dosage form may also comprise buffering agents.

Solid compositions of a similar type may also be employed as fillers in soft and hard- filled gelatin capsules using such excipients as lactose or milk sugar as well as high molecular weight polyethylene glycols and the like.

The active compounds can also be in micro-encapsulated form with one or more excipients as noted above. The solid dosage forms of tablets, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate. with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1.3-butylene glycol, dimethyl formamide. oils (in particular, cottonseed, groundnut corn, olive, castor and sesame oils). glycerol, tetrahydrofuryl alcohol. polyethylene glycols and fatty acid esters of sorbitan, and mixtures thereof.

Besides inert diluents, the oral compositions can also include adjuvants such as wetting agents, emulsifying and suspending agents, and sweetening, flavoring and perfuming agents.

Suspensions, in addition to the active compounds. may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Topical administration includes administration to the skin or mucosa, including surfaces of the lung and eye. Compositions for topical administration, including those for inhalation, may be prepared as a dry powder which may be pressurized or non-pressurized. In non-pressurized powder compositions, the active ingredient in finely divided form may be used in admixture with a larger-sized pharmaceutically acceptable inert carrier comprising particles having a size, for example, of up to 100 micrometers in diameter. Suitable inert carriers include sugars such as lactose. Desirably, at least 95% by weight of the particles of the active ingredient have an effective particle size in the range of 0.01 to 10 micrometers.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

Alternatively, the composition may be pressurized and contain a compressed gas, such as nitrogen or a liquified gas propellant. The liquified propellant medium and indeed the total composition is preferably such that the active ingredient does not dissolve therein to any substantial extent. The pressurized composition may also contain a surface active agent. The surface active agent may be a liquid or solid non-ionic surface active agent or may be a solid anionic surface active agent. It is preferred to use the solid anionic surface active agent in the form of a sodium salt.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

The therapeutically effective amount of the compound can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic. Methods to form liposomes are known in the art. See, for example, Prescott, Ed., *Methods in Cell Biology,* Volume XIV, Academic Press, New York, N.Y., 1976, p.33 et seq.

Synthetic Methods

The process of preparing compounds of the invention may be better understood in connection with the following Schemes 1–5. In describing the processes and the Examples which are following, certain abbreviations are used in describing reagents and methods commonly used in the process. Where used herein the abbreviations substitute for the following: DBU for 1,8-diazabicyclo[5.4.0]undec-7-ene; DMAP for 4-dimethylaminopyridine; DMF for -dimethylforrnamide; EDCI for 1-(3-dimethylaminopropyl)-3-ethylcarbodiimide; HOBt for 1-hydroxybenzotriazole hydrate; LAH for lithium aluminum hydride; OMe for methoxy; PCC for pyridinium chlorochromate; and THF for tetrahydrofuran.

As summarized below and fuirther described herein in accordance with the Examples, Schemes 1–5 illustrate processes within the scope of the invention. Scheme 1 describes the general method for preparing tetrahydroisoquinoline derivatives of the general formula (I), which is followed by more preferred syntheses carried out in accordance with Schemes 2–5. The tetrahydroisoquinoline derivatives are prepared from a substituted aminoalkanol, wherein a single carbon of the alkyl chain is disubstituted with an aryl moiety, preferably a phenyl group. Procedures for obtaining the aminoalkanol are readily ascertained by those of skill in the art from methods previously described, for example EP 0712845 for the preparation of 6-amino-4,4- diphenylhexanol. Exemplary synthesis of the diphenyl-substituted aminoalkanol is more particularly illustrated and further detailed in Schemes 2–5 and in the Examples.

As illustrated by Scheme 1, Step (i) represents the N-substitution of the amino moiety by acylating the nitrogen of the amino group or by coupling with an activated carboxylic acid. PCC or Swern oxidation of the alcohol to the aldehyde is shown in Step (ii). Alkylation of an isoquinoline ring as represented by Step (iii) affords the tetrahydroisoquinoline derivative. Alternatively, a reactive leaving group $R_9$ is prepared from the alcohol, Step (ii-a), which is alkylated with the isoquinoline ring or the hydroiodide salt of the isoquinoline moiety represented in Step (iii-a). $R_9$ is selected from the group consisting of halide and mesylate.

The variables l, m, n,p, W, X, Y, Z, $R_1$, and $R_2$ described in Scheme 1 are as defined in claim 1. $R_3$ is selected from hydroxy, halo, or an aryl ring substituted with an electron withdrawing group to obtain an activated ester as illustrated by Scheme 1 below.

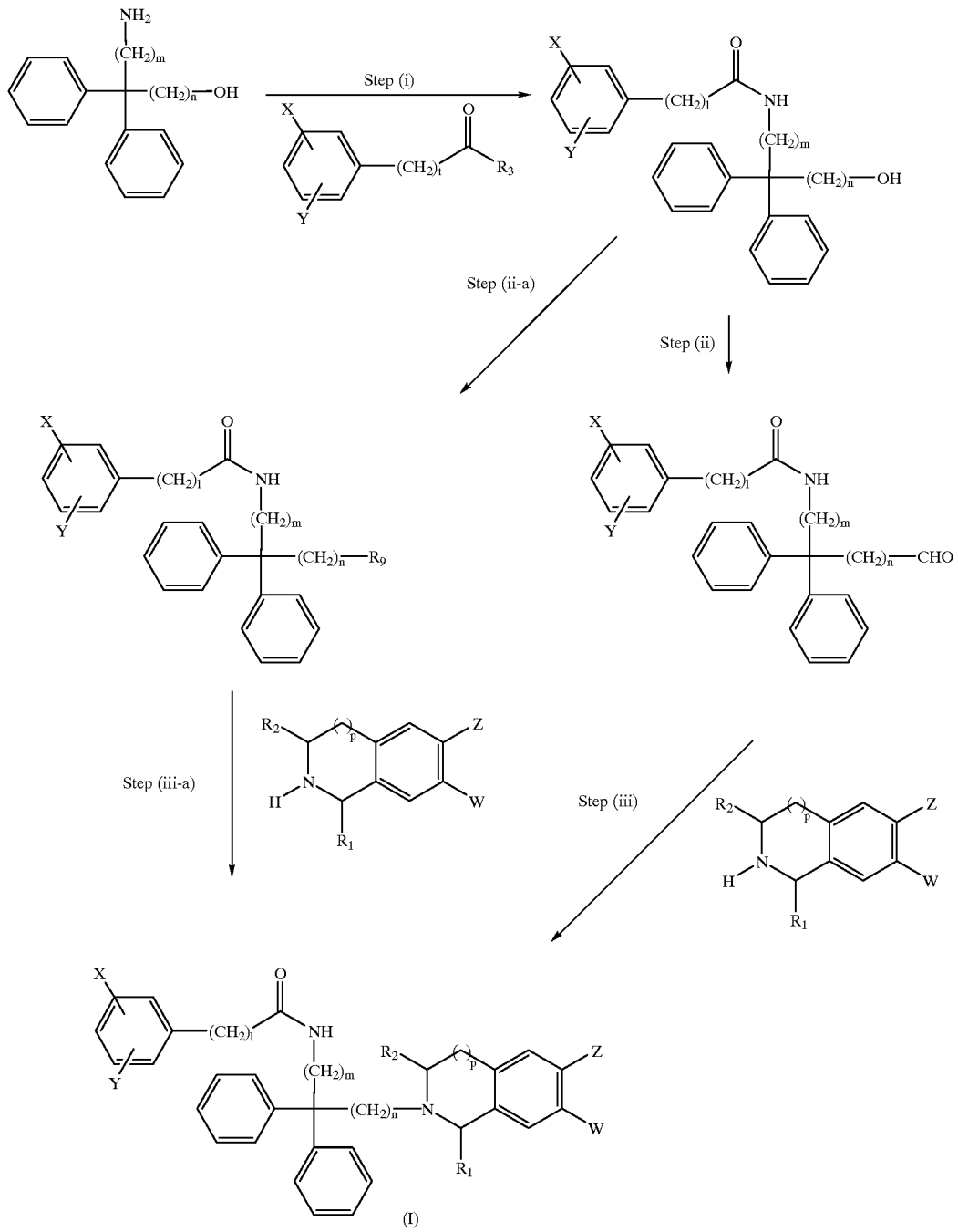

Scheme 1

The following Schemes 2–5 further describe methods of preparing compounds within the scope of the general formula (I). In particular, Scheme 2 represents a process for preparing a compound of formula (II) starting with the condensation of diphenylacetaldehyde and acrylonitrile and followed by additional chemical transformations well known in the art. Scheme 3 involves a coupling reaction of an aryl-substituted (aryl)alkylamine with a carboxylic acid, followed by cyclization to form a tetraisoquinoline moiety which is an intermediate suitable for alkylating compound 7, 8, or 9 of Scheme 2. A compound of the formula (III) is prepared from 4,4-diphenyl-forrnylbutyronitrile as illustrated in Scheme 4. Scheme 5 represents a process for preparing a compound of general formula (IV) via a Wittig reaction of 4,4-diphenyl-5-formyl-pentanonitrile followed by conventional chemical steps. The variables $R_1$, $R_2$, W, X, Y, and Z described in the schemes are the groups defined in claim 1. The group $R_3$ is selected from hydroxy, halo, or an aryl ring substituted with an electron withdrawing group to obtain an activated ester.

Scheme 2

Condensation of diphenylacetaldehyde and acrylonitrile is carried out in the presence of base to afford a 4,4-diphenyl-formylbutyronitrile 1. The aldehyde is converted to a 6-cyano-4,4,-diphenyl-α,β-unsaturated ester 2 via Wittig reaction. Hydrogenation of 2 in the presence of 10% Pd/C affords compound 3. Treating the ester 3 with lithium aluminum hydride reduces the ester as well as the cyano moiety to form a 4,4-diphenyl-substituted aminoalkanol 4. N-acylation of compound 4 with an acid or acid halide of formula 5 affords an N-acyl-4,4-diphenyl-amino-alkanol 6. Swern oxidation of compound 6 oxidizes the alcohol moiety to an aldehyde of compound 7. Reductive alkylation of a tetrahydroisoquinoline with compound 7 in the presence of sodium cyanoborane affords the tetrahydroisoquinoline derivative of formula (II).

Alternatively, displacement of the alcohol moiety with a halide in compound 8 is obtained by Mitsunobu reaction of compound 6. Treatment of compound 6 with methanesulfonyl chloride results in hydroxy displacement with a mesylate moiety to form compound 9. Direct alkylation of the tetrahydroisoquinoline moiety with compound 8 or compound 9 affords the tetrahydroisoquinoline derivative (II).

Scheme 3

Condensation of aryl-substituted (aryl)alkylamine 10 with an activated carboxylic acid 11 forms an amide of formula 12. Treatment of compound 12 with oxalyl chloride affords compound 13. Treatment of compound 13 with acid and FeCl$_3$ forms compound 14. Compound 14 is decarboxylated to provide compound 15. Reduction of 15 with sodium cyanoborohydride affords an isoquinoline intermediate of formula (A).

Another known method to form isoquinoline ring (A) is by the cyclization of compound 12 with POCl$_3$ to afford compound 15. Reacting compound 15 with sodium cyanoborane yields the isoquinoline derivative (A).

Optionally treating the isoquinoline ring with hydriodic acid affords a hydroiodide salt of the isoquinoline ring.

Scheme 4

Wittig reaction of 4,4-diphenyl-formylbutyronitrile followed by acid hydrolysis of 16. with HCl affords aldehyde 17. Treatment of 17 with lithium aluminum hydride reduces the cyano and the aldehyde moieties to the amine and hydroxy moieties, respectively, affording compound 18. N-substitution of 18 with an activated carboxylic acid of formula 5 from Scheme 1 affords a compound of formula 19. N-mesylation of compound 19 in the presence of methanesulfonyl chloride yields 20. Direct alkylation of 20 results in a compound of formula (III).

Scheme 5

Wittig reaction of 17 affords an α,β-unsaturated ester 21. Hydrogenation of the α,β-unsaturated double bond forms 22. Compound 22 is reduced to compound 23 with lithium aluminum hydride to the amino alcohol, which is N-substituted with an acyl group to form a compound of formula 24. Direct alkylation of a tetraisoquinoline hydroiodide salt with mesylate 25 affords a compound of formula (IV).

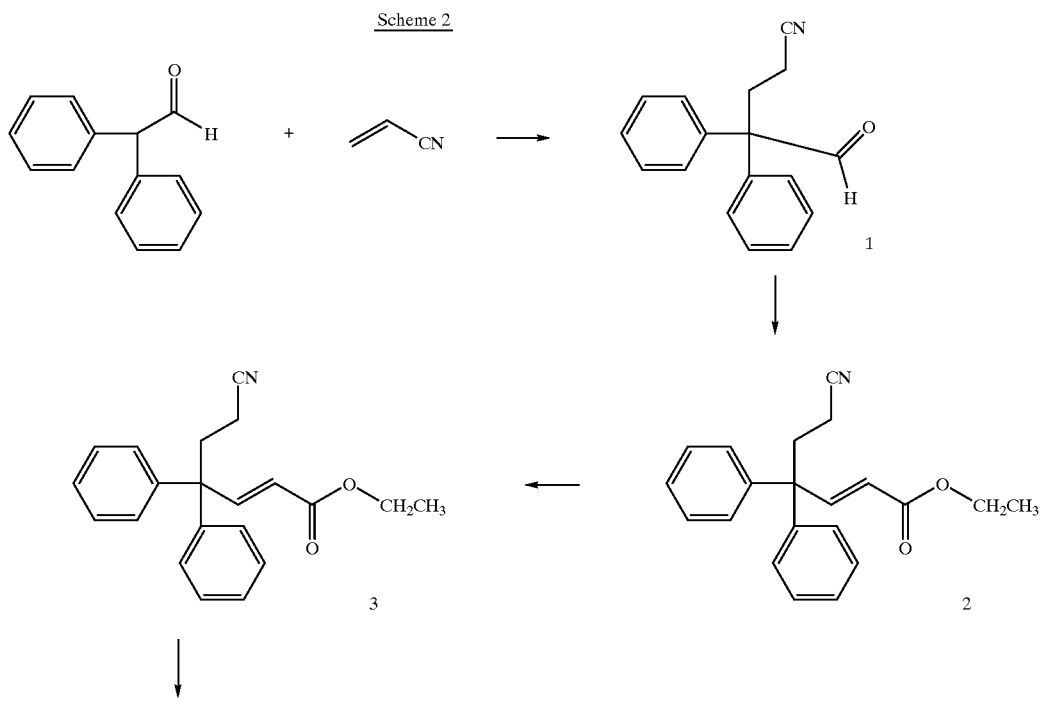

Scheme 2

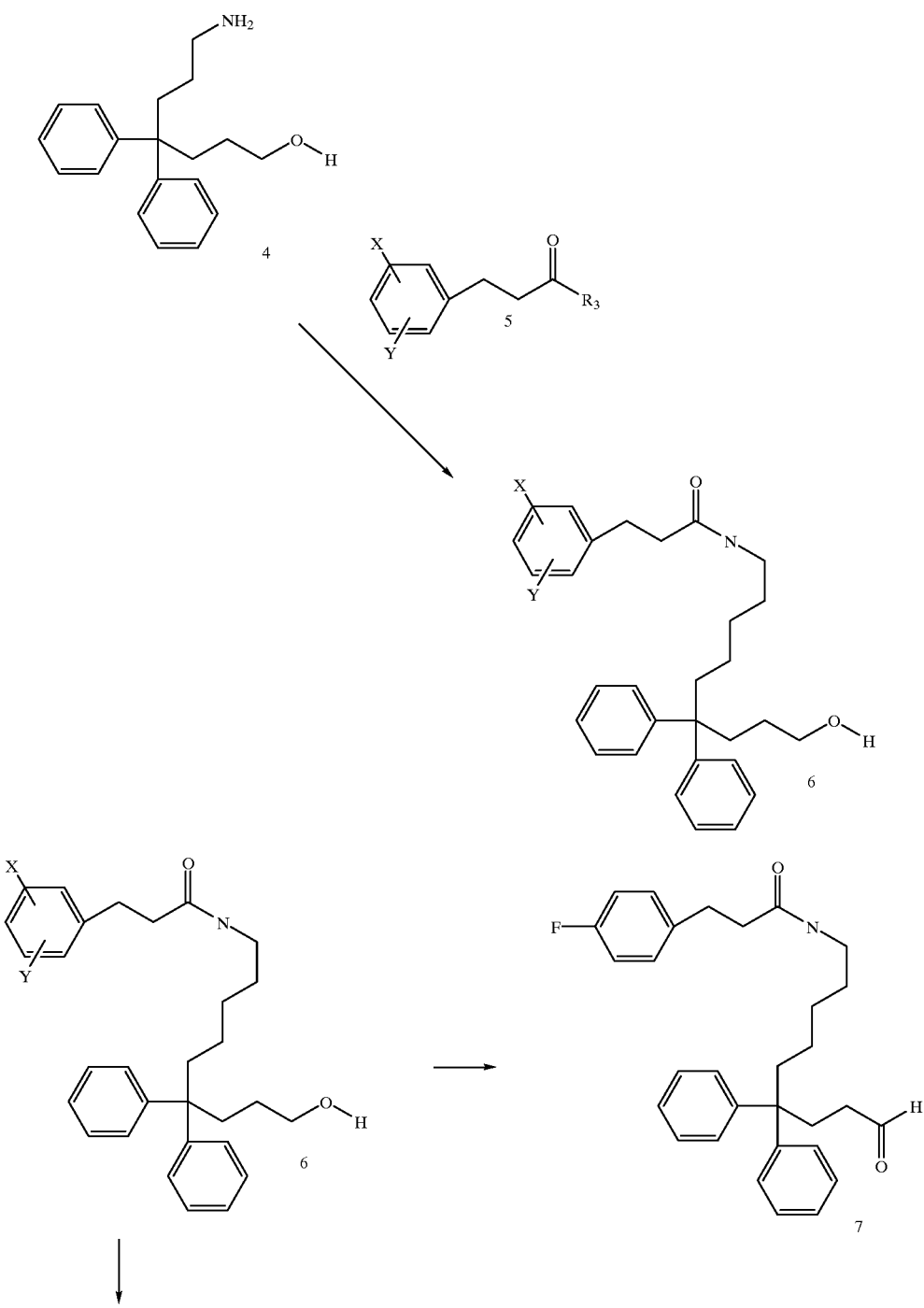

-continued
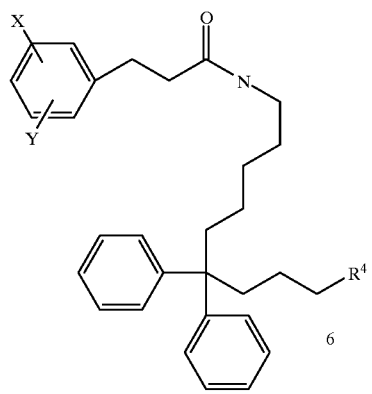
8  R₄ = I
9  R₄ = OMs
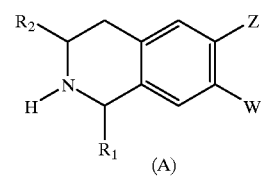
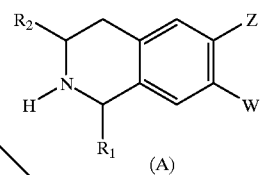
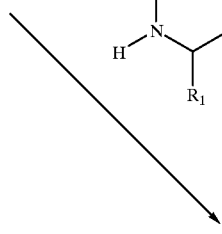
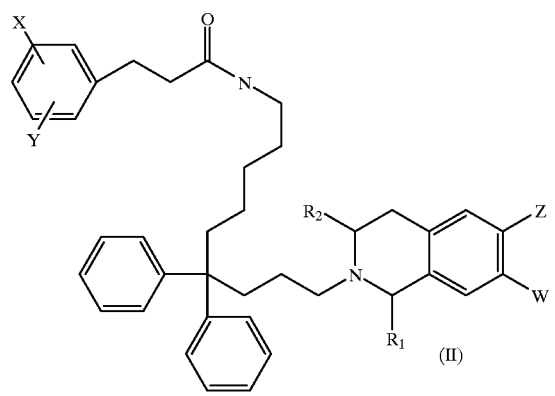

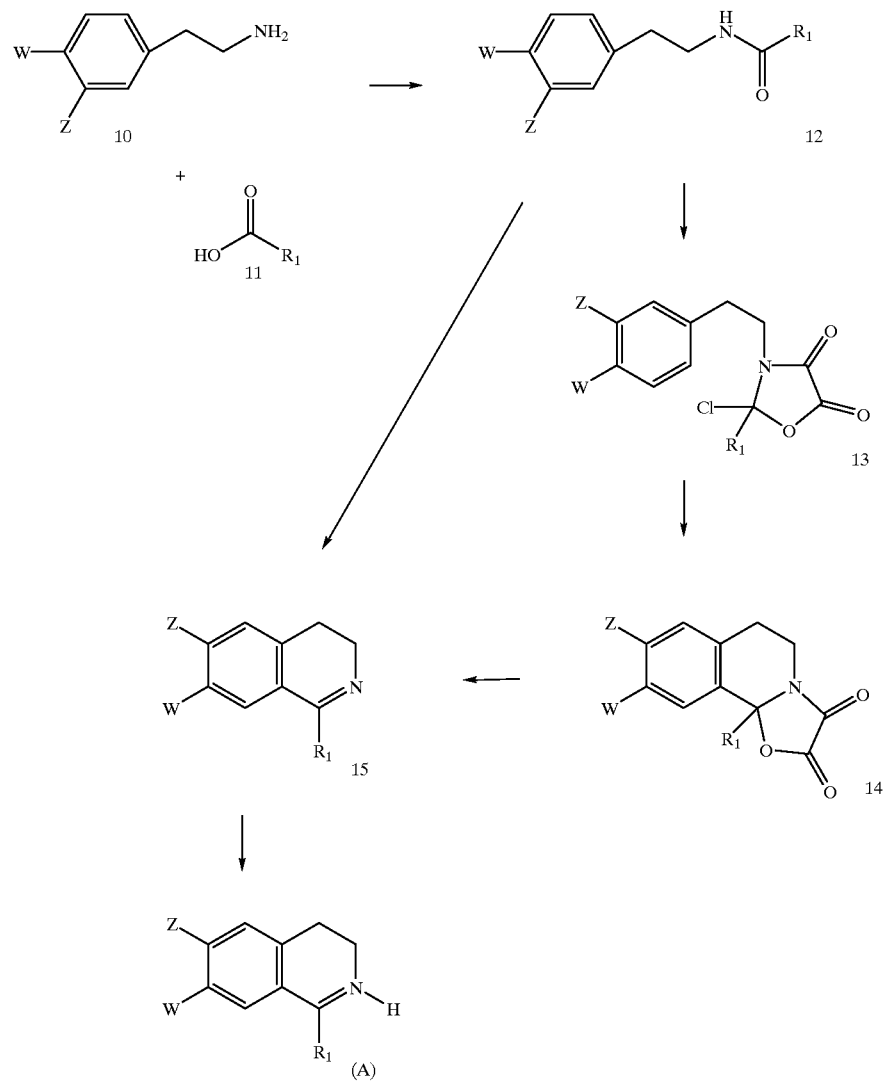

Scheme 4
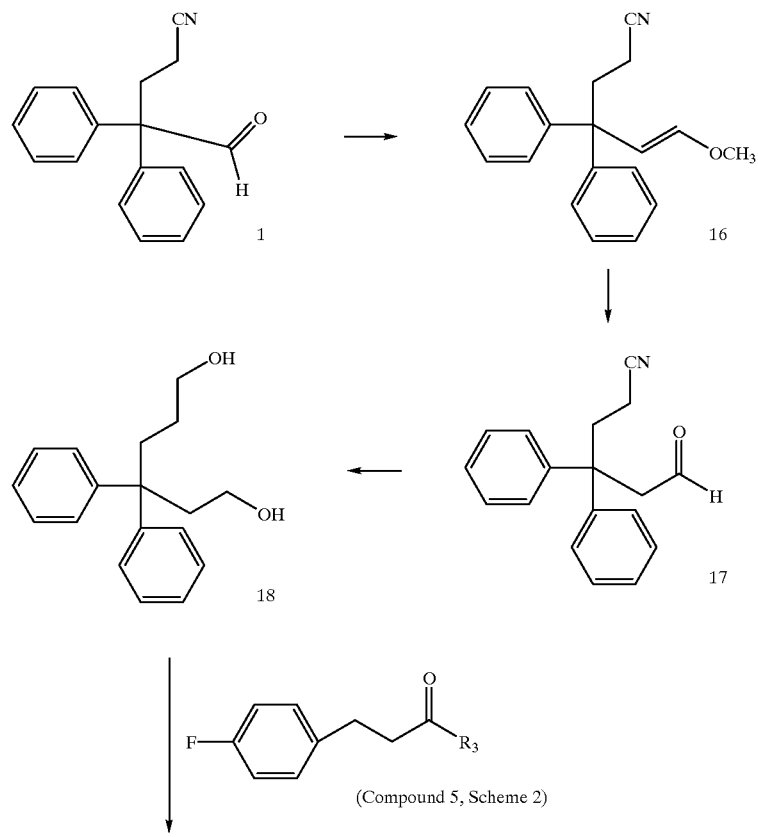

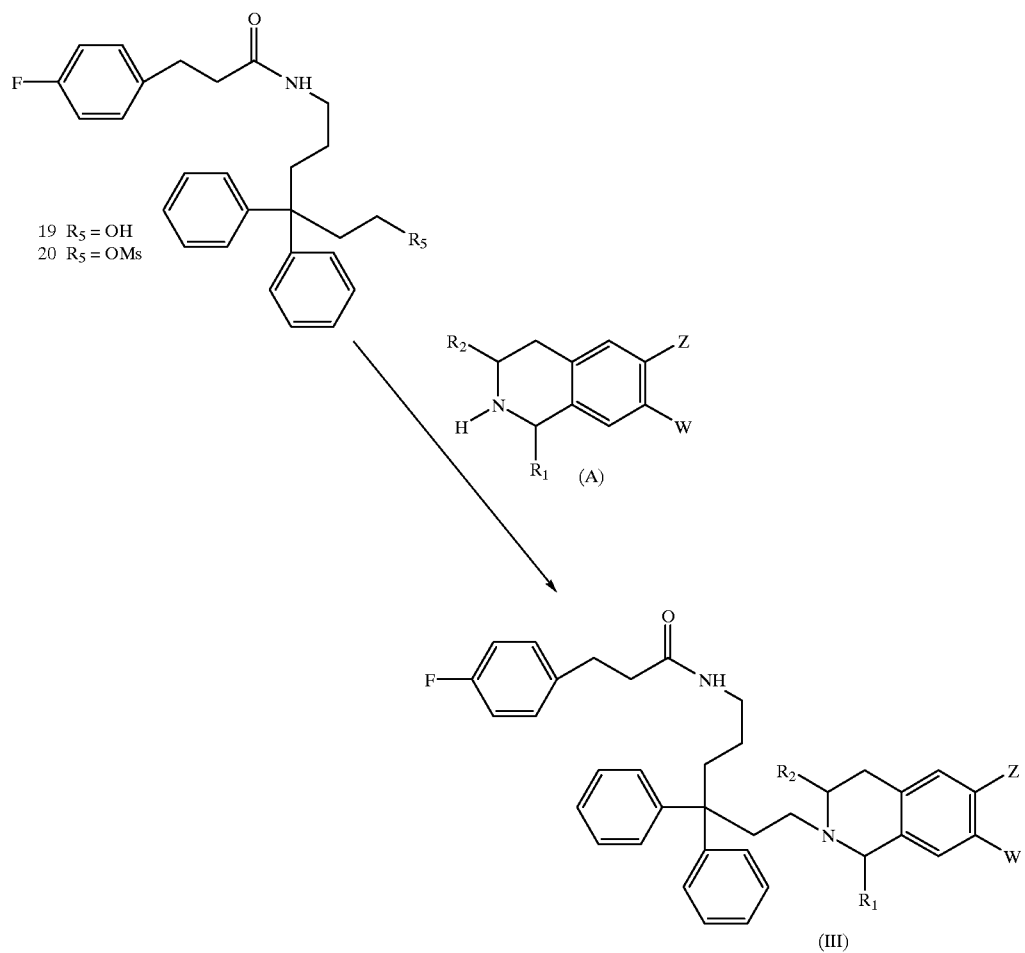
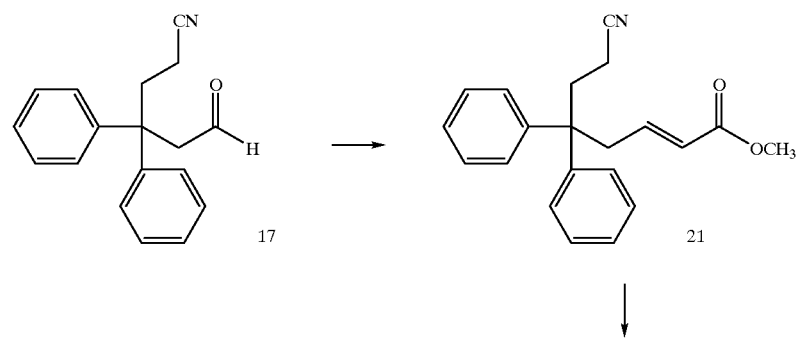

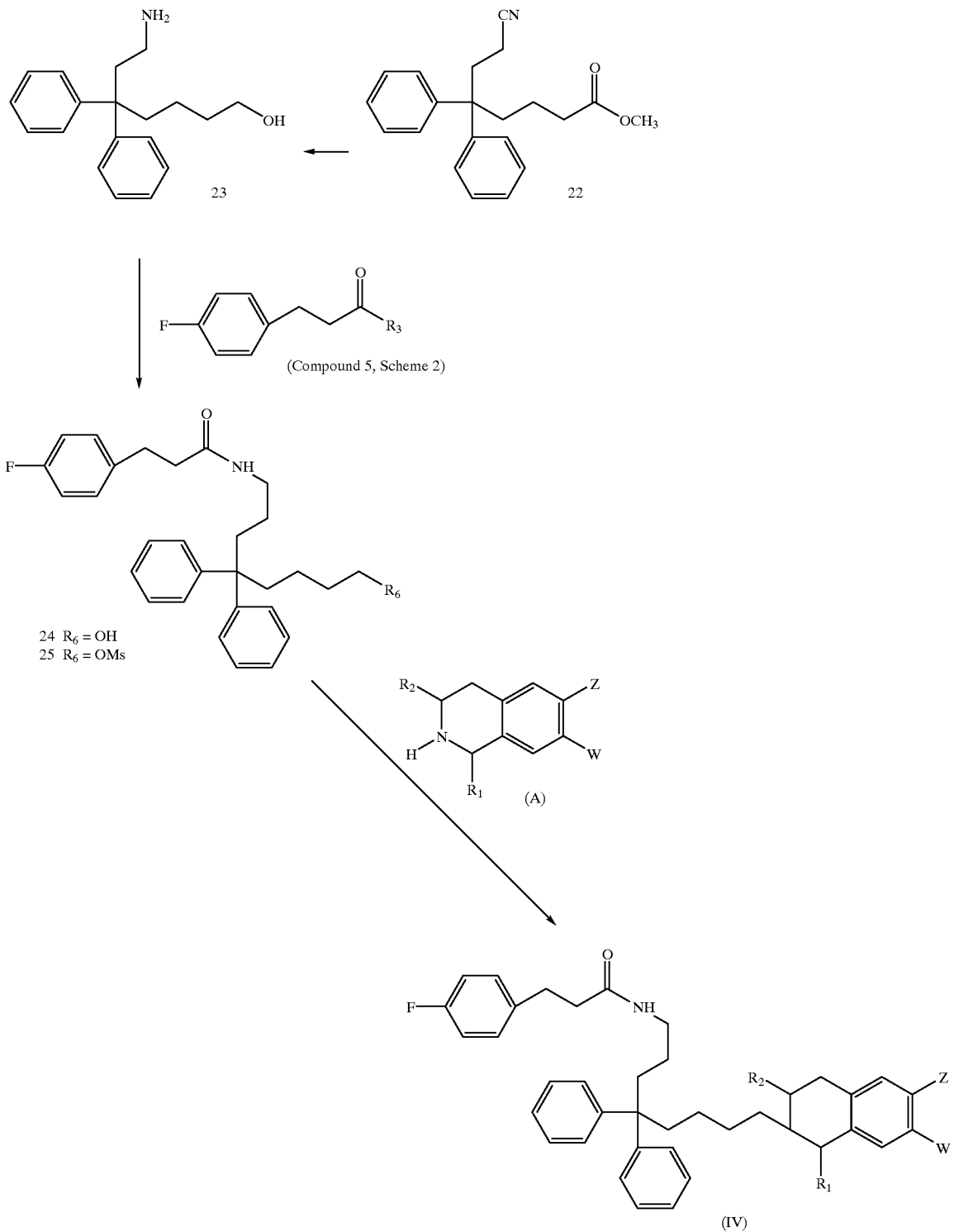

The foregoing Schemes 1–5 will be better understood in connection with the Examples, which are intended as an illustration of and not a limitation upon the scope of the invention. The following Examples further describe compounds prepared in accordance with the invention. Modification of the disclosed embodiments to achieve additional compounds having LHRH antagonist activity will be apparent to those skilled in the art. Such substitution, modification, and change are within the purview of the scope and limitations of the present invention and do not depart from the spirit of the invention thereof.

EXAMPLES

Example 1

(R,S) 7-[N-3-(4-Fluorophenyl)propionyl]amino-1-[N-(1,2,3,4-tetrahydro-1-methyl-6,7-dimethoxyisoquinolinyl]1–4,4-diphenylheptane hydrochloride Step 1: 4.4-Diphenyl-4-formylbutyronitrile (Compound I. Scheme 2)

To a stirred solution of diphenylacetaldehyde (11.0 mL) and acrylonitrile (4.5 mL) in dioxane (125 mL) was added 1,8-diazabicyclo[5.4.0]undec-7-ene (DBU) (10.5 mL). The solution was heated under reflux overnight and then concentrated in vacuo. The residue was purified by a silica gel column eluting with (95:5) hexane/ethyl acetate. The desired product (8.115 g) was obtained a colorless crystals, mp 80–82° C.: MS showed $(M+NH_4)^+$ @ 267; $^1$H-NMR $(CDCl_3, \delta)$: 2.05–2.15 (m, 2H), 2.65–2.75 (m, 2H). 7.11–7.45 (m, 10 H), 9.80 (s, 1H); Anal. Calcd for $C_{17}H_{15}NO$: C, 81.90; H, 6.60; N, 5.61. Found: C, 81.83; H, 6.64; N, 5.65.

Step 2: Ethyl 6-cyano-4.4-diphenyl-hex-2-enoate (Compound 2. Scheme 2)

A mixture of 4,4-diphenyl-4-formylbutyronitrile (8.04 g) and (carbethoxymethylene)-triphenylphosphorane (20.85 g) in toluene (200 mL) was heated under reflux for 3 days. The reaction mixture was concentrated in vacuo and the residue was purified by a silica gel column chromatography to give the desired product as a yellow-orange oil (12.10 g): MS showed $(M+NH_4)^+$ @ 337; $^1$H-NMR $(CDCl_3, \delta)$: 1.25–1.32 (t. 3H), 2.10–2.18 (m, 2H), 2.65–2.75 (m, 2H), 4.15–4.23 (q, 2H), 5.60–5.66 (d. 1H), 7.05–7.75 (m. l 1H).

Step 3: Ethyl 6-cyano-4.4-diphenyl-hexanoate (Compound 3. Scheme 2)

A solution of ethyl 6-cyano-4,4-diphenyl-hex-2-enoate (22.06 g) in ethanol (500 mL) was hydrogenated in the presence of 10% Pd/C (2.2 g) under 4 atmospheric pressure for 17 hr. The catalyst was filtered and the filtrate was concentrated in vacuo. The residue was purified by a silica gel column chromatography eluting with (95:5) hexane/ ethyl acetate. The desired product (19.49 g) was obtained as colorless oil: MS showed $(M+NH_4)^+$ @ 339; $^1$H-NMR $(CDCl_3, \delta)$: 1.20–1.25 (t, 3H), 1.95–2.06 (m, 4H), 2.38–2.52 (m, 4H), 4.03–4.12 (m, 2H), 7.10–7.36 (m, 1OH).

Step 4: 7-Amino-4.4-diphenylheptan-1-ol (Compound 4. Scheme 2)

To a solution of ethyl 6-cyano-4,4-diphenyl-hexanoate (5.476 g) in anhydrous THF (195 mL) was added portionwise lithium aluminum hydride (LAH) (1.686 g). A large evolution of gas was observed. The mixture was stirred at rt for 1.5 hr. The reaction mixture was quenched by a careful addition of water (4.5 mL), followed by IN NaOH (4.5 mL) and additional water (15 niL). The mixture was stirred at rt for 10 min and then filtered and the solid was washed three times with THF. The organic filtrates were combined, dried $(Na_2SO_4)$ and concentrated to give the desired product as a solid foam (4.56 g): MS showed $(M+H)^+$ @ 284; $^1$H-NMR $(CDCl_3, \delta)$: 1.05–1.3 (m, 4H), 2.0–2.20 (m, 4H), 2.30–2.42 (t, 2H), 2.82–3.0 (t, 2H), 3.0–3.25 (m, 2H), 3.50–3.65 (t, 2H), 5.10–5.20 (broad m, 1H), 6.86–7.36 (m, 14H).

Step 5: 7-[N-3-(4-Fluorophenyl)propionyl]amino-4.4-diphenylhe tan-1-ol (Compound 6. Scheme 2)

To an ice-cold and stirred solution of 7-amino-4,4-diphenylheptan-1-ol (4.14 g) in (9.5:0.5) methylene chloride/DMF solution (42 mL) was added 4-fluorophenylpropionic acid (2.70 g) (Compound 5 Scheme 2) followed by 1-hydroxybenzotriazole hydrate (HOBt) (2.38 g), triethylamine (5.0 mL), and 1-(3-dimethylaminopropyl)-3-ethylcarbodiimide (EDCI) (3.36 g). The reaction mixture was stirred at rt overnight and then diluted with methylene chloride (150 mL). The solution was washed first with water and then with brine. The organic phase was dried $(Na2SO_4)$ and concentrated in vacuo. The residue was purified by a silica gel column using (1:1) ethyl acetate/hexane. It yielded the desired compound as an amorphous solid (2.10 g): MS showed $(M+H)^+$ @ 434; $^1$H-NMR $(CDCl_3\delta)$: 1.05–1.28 (m, 4H), 1.7–1.8 (m, 1H), 2.0–2.2 (m. 4H), 2.3–2.4 (t, 2H), 2.85–2.92 (m. 2H) 3.08–3.2 (q, 2H), 3.5–3.6 (q, 2H). 5.3–5.35 (m. 1H), 6.85–7.30 (m, 14H).

Step2 6: 7-[N-3-(4-Fluorophenyl)propionyl]amino4,4-diphenylheptan-1-al (Compound 7. Scheme 2)

To a stirred slurry of silica gel (2.03 g) and celite (2.02 g) in methylene chloride (80 mL) was added pyridinium chlorochromate (PCC) (2.06 g) followed by a dropwise addition of a solution of 7-[N-3-(4-fluorophenyl)propionyl]amino-4,4-diphenylheptan-1-ol (2.085 g) in methylene chloride (30 mL). The reaction mixture was stirred at rt for 3.5 hr and then diluted with anhydrous ether (50 mL) and stirred for 10 min. The mixture was filtered through a celite pad and the filtrate was concentrated in vacuo. The brown residue was dissolved in ethyl acetate and the solution was washed with sodium bicarbonate, water and brine solutions. The organic extracts were dried $(Na_2SO_4)$ and concentrated in vacuo. The desired product was obtained as a heavy oil (1.7 g): MS showed $(M+H)^+$ (432 and $(M+NH_4)^+$ (449; $^1$H-NMR $(CDCl_3, \delta)$: 1.05–1.18 (m, 2H), 1.95–2.08 (m, 2H), 2.1–2.2 (t, 2H), 2.3–2.5 (m, 4H), 2.8–3.0 (t, 2H), 3.08–3.20 .(q, 2H), 5.08–5.20 (m, 1H), 6.87–7.35 (m, 14H), 9.6 (s, 1H).

Step 7: (R,S)7-[N-3-(4-Fluorophenyl)propionyl]amino-1-[N-(1,2,3,4-tetrahydro-1-methyl–6.7-dimethoxyisoguinolinyl)]-4,4-diphenylheptane hydrochloride (Compound II. Scheme 2)

To a solution of 7-[N-3-(4-fluorophenyl)propionyl] amino-4,4-diphenylheptan-1-al (0.796 g) in methanol (30 mL) was added (R,S) 1,2,3,4-tetrahydro-1-methyl-6,7-dimethoxyisoquinoline (0.658 g) followed by sodium cyanoborohydride (0.235 g) and three drops of acetic acid. The mixture was stirred at rt overnight and then concentrated in vacuo. The residue was treated with ethyl acetate and washed with sodium bicarbonate and brine solutions. The organic phase was dried $(Na_2SO_4)$ and concentrated in vacuo. The residue was purified by a silica gel column chromatography eluting with a gradient of hexane/ethyl acetate. The desired product was obtained as a viscous oil (0.30 g): MS showed $(M+H)^+$ @ 623; $^1$H-NMR $(CDCl_3, \delta)$: 1.06–1.3 (m, 7H), 2.0–2.18 (m, 4H), 2.30–2.40 (t, 2H), 2.40–2.85 (m, 6H), 2.85–2.98 (t, 2H), 3.10–3.20 (q, 2H). 3.6–3.7(m. 1H), 3.8–3.88 (two s, 6H), 6.45 (s, 1H). 6.55 (s. 1H). 6.88–6.97 (m, 2H), 7.08- 7.32 (m. 12H). This compound was treated with methanolic HCl. the solution was concentrated in vacuo and the residue was dissolved in (1:1) acetonitrile/water and lvophilized to give (R,S) 7-[N-3-(4-fluorophenyl)propionyl]amino-1-[N-(1,2,3.4-tetrahydro-1-methyl-6,7-di-methoxy-isoquinolinyl)]-4,4-diphenylheptane hydrochloride: mp 113–115° C.; IR (KBr) u 3400. 3300, 2950, 1750 cm$^{-1}$; Anal. Calcd for $C_{40}H_{47}N_2,O_3FHCl1H_2O$: C. 70.93; H, 7.44; N, 4.13; Found: C, 71.04; H, 7.32; N, 3.91.

Example 2

(R) 7-[N-3-(4-Fluorophenyl)propionyl]-1-N-(1,2,3,4)-tetrahydro-1-methyl-6,7-dimethoxyisoguinolinyl)1–4,4-diohenylheptane hydrochloride Step 1: 7-[N-3-(4-Fluorophenyl)propionyl]amino-4.4-diphenylheptyl iodide (Compound 8. Scheme 2)

To a solution of 7-[N-3-(4-fluorophenyl)propionyl] amino-4,4-diphenylheptan-1-ol (0.78 g) in toluene (40 mL) was added methyltriphenoxyphosphonium iodide (0.93 g) and the mixture was stirred at rt for 2 hr. The reaction mixture was washed with sodium bicarbonate and brine solutions. The organic phase was dried ($Na_2SO_4$) and concentrated in vacuo. The residue was purified by a silica gel column chromatography yielding the desired compound (0.912 g) as a semisolid compound: $^1$H-NMR ($CDCl_3$, δ): 1.05–1.2 (m, 2H), 1.32–1.5 (m, 2H), 1.96–2.05 (m, 2H), 2.1–2.2 (m, 2H), 2.32–2.4 (t, 2H), 2.85–2.95 (t, 2H), 3.05–3.20 (m, 4H), 5.02–5.12 (m, 1H), 6.88–7.35 (m, 14H).

Step 2: (R) 7-[N-3-(4-Fluorophenol)Propionyl]amino-1-[N-(1,2,3,4-tetrahydro-1-methyl-6.7-di-methoxyisoquinolinyl] 1–4.4-diphenylheptane hydrochloride (Compound II. Scheme 2) To a solution of 7-[N-3-(4-fluorophenyl) propionyl]amino-4,4-diphenylheptyl iodide (0.912 g) in dioxane (3OmL) was added (R) 1,2,3,4-tetrahydro-1-methyl-6,7-dimethoxy- isoquinoline (0.33 g) followed by a solution of potassium carbonate (0.230 g) in water (2 mL). The mixture was heated at 70° C. for 34 hr and then cooled to rt and diluted with ethyl acetate. The organic phase was washed twice with brine, dried ($Na_2SO_4$) and concentrated in vacuo. The residue was purified using a silica gel column chromatography eluting with (95:5) ethyl acetate/methanol. The desired product (R) 7-[N-3-(4-fluorophenyl)propionyl] amino-1- [N-(1,2,3,4-tetrahydro-1-methyl-6,7-dimethoxyisoquinolinyl)]-4,4-diphenylheptane (0.693 g) was obtained as a dry foam: [a:]$^{25}$D =-11.0° C.=1. EtOH): MS showed (M+H)$^+$ @ 623; $^1$H- NMR ($CDCl_3$, δ): 1.06–1.32 (m, 7H). 2.03–2.18 (m. 4H), 2.32–3.0 (m, 10 H) 3.10–3.20 (q, 2H), 3.60–3.72 (m, 1H), 3.82–3.88 (two s, 6H), 6.48 (s, 1H), 6.53 (s, 1H), 6.87–6.97 (t, 2H), 7.08–7.30 (m, 12H). This compound was treated with methanol/HCl solution and the solvent was. removed in vacuo. The residue was dissolved in (1:1) acetonitrile/water and lyophilized to give the hydrochloride salt of the desired product: mp 113–115° C.; IR (KBr) u 3400, 3300, 2950, 1750 cm$^{-1}$; Anal. Calcd for $C_{40}H_{47}N_2O_3F$·HCl: C, 72.87; H, 7.33; N, 4.24; Found: C, 72.61; H, 7.33; N, 4.13.

Example 3

(S) 7-[N-3-(4-Fluorophenyl)propionyl]amino-1-[N-(1,2,3,4-tetrahydro-1-methyl-6.7-dimethoxyisoquinolinyl]]1–4.4-diphenylheptane hydrochloride The procedure described in example 2 was used but substituting (S) 1,2,3,4-tetrahydro-1- methyl-4,5-dimethoxyisoquinoline for (R) 1,2,3,4-tetrahydro-1-methyl-4,5-dimethoxy- isoquinoline. After chromatography purification the desired product (S) 7-[N-3-(4-fluorophenyl-propionyl)]-1-[N-(1,2,3,4-tetrahydro-1-methyl-6,7-dimethoxyisoquinolinyl)]4,4-diphenyl-heptane was obtained as a dry foam; [cc] =+12.80 (c =1, EtOH): MS showed (M+H)$^+$ (623; $^1$H-NMR ($CDCl_3$, δ): 1.1 (m, 2H) 1.22–1.32 (m, 5H), 2.05–2.18 (m, 4H), 2.38–2.45 (t, 2H), 2.50–2.82 (m, 5H), 2.90–2.95 (t, 2H), 2.95–3.08 (m, 1H), 3.10–3.22 (q, 2H), 3.72–3.82(m, 1H) 3.82–3.90 (s, 6H), 5.5–5.65 (broad m, 1H), 6.50 (s, 1H), 6.58 (s, 1H), 6.88–6.97 (t, 2H), 7.08–7.32 12H). This compound was treated with methanol/HCl solution and the solvent was removed in vacuo. The residue was dissolved in (1:1) acetonitrile/water and lyophilized to give the hydrochloride salt of the desired product: mp 113–115° C.; IR (KBr) v 3400, 3300, 2950, 1750 cm$^{-1}$; Anal. Calcd for $C_{40}H_{47}N_2O_3F$,HCl: C, 72.87; H, 7.33; N, 4.24; Found: C. 72.24; H, 7.18; N, 4.18.

Example 4

7-[N-3-(4-Fluorolphenyl)Propionyl]1-[N-(1,2,3,4-tetrahydro-1-cyclopropyl-6.7-dimethoxyisoquinolinyl)]-4,4-diphenylheptane hydrochloride Step 1: [N-2-(3,4-Dimethoxyphenyl)ethyl] cyclopropylcarboxyl amide (Compound 12. Scheme 3)

To a solution of 3,4-dimethoxyphenethylamine (5.0 g) in methylene chloride (lOOmL), cooled to 0° C., was slowly added cyclopropylcarbonyl chloride (2.5 mL) followed by triethylamine (7 mL) and 4-dimethylaminopyridine (DMAP) (0.173 g). The reaction mixture was stirred at rt for 2 hr and then washed with sodium bicarbonate, 0.5 M citric acid and brine solutions. The organic phase was dried ($Na_2SO_4$) and concentrated in vacuo. The residue was crystallized from ethyl acetate to yield the desired product (4.98 g) as yellow powder: MS showed (M+H)$^+$ (250; $^1$H-NMR ($CDCl_3$, δ): 0.68–0.78 (m, 2H), 0.93–1.0 (m, 2H), 1.22–1.35 (m, 1H), 2.73–2.82 (t, 2H), 3.48–3.57 (q, 2H), 3.88 (two s, 6H), 5.68 (broad s, I H), 6.72–6.87 (m, 3H).

Step 2: 3.4-Dihydro-1-cyclopropyl-6.7-dimethoxyisoguinoline (Compound 15. Scheme 3)

To a solution of [2-(3,4-dimethoxyphenyl)ethyl] cyclopropylcarboxyl amide (4.9713 g) in toluene (200 mL) was added $POCl_3$ (10 mL). The mixture was heated under reflux with stirring under nitrogen for 2 hr, cooled to rt, poured over ice, basified to pH 10 with 1 M NaOH and extracted three times with ethyl acetate. The organic phase was washed with brine, dried ($Na_2SO_4$) and concentrated in vacuo to give the desired product as a colored hard foam: MS showed (M+H)$^+$ @ 232; $^1$H-NMR ($CDCl_3$, δ): 1.48–1.59 (m, 2H), 1.95–2.05 (m, 2H), 2.30–2.41 (m, 1H), 2.96–3.07 (t, 2H), 3.82–3.92 (m, 2H), 3.98 (s, 3H), 4.03 (s, 3H), 6.85 (s, 1H), 7.45 (s, 1H).

Step 3: 1.2.3,4-Tetrahydro-1-cyclopropyl-6.7-dimethoxyisoguinoline (Compound A. Scheme 3)

To a stirred solution of 3,4-dihydro-1-cyclopropyl-6.7-dimethoxyisoquinoline (3.9318 g) in methanol (100 mL) was added under nitrogen $NaCNBH_3$ (1.28 g) in the presence of three drops of acetic acid. The mixture was stirred at rt for 2 hr and then concentrated in vacuo and the residue was taken in ethyl acetate and washed with sodium bicarbonate and brine solutions. The organic phase was dried and concentrated in vacuo to give the desired product as a tan solid: MS showed (M+H)$^+$ @ 234; $^1$H-NMR ($CDCl_3$, δ): 0.3–0.41 (m. 1H), 0.5–0.65 (m, 2H), 0.77–0.9 (m, 1H), 1.02–1.16 (m, 1H), 2.25 (broad s, 1H), 2.6–2.75 (in, 1H). 2.85–3.08 (m, 2H), 3.28–3.36 (m, 1H), 3.88 (two s, 6H), 6.60 (s, 1H), 7.08 (s, 1H).

Step 4: 1,2,3,4-Tetrahydro-1-cyclopropyl-6.7-dimethoxyisoquinoline hydroiodide

To a solution of 1,2.3,4-tetrahydro-1-cyclopropyl-6,7-dimethoxyisoquinoline (0.802 g) in ethanol (10 mL) cooled to 0° C. was added dropwise a solution of 57% HI solution (0.5 mL). The ice bath was removed and the solution was stirred at rt for 20 min in the dark. To the bright orange solution was added ether (250 mL) and the mixture was stirred for 10 min. The light yellow precipitate was filtered and dried in vacuo under $P_2O_5$ to give the desired salt (0.958 g).

Step2 5: 7-[N-3-(4-Fluorophenyl)propionyl]-amino-1-[N-(1,2.3.4-tetrahydro-1-cyclopropyl-6.7-dimethoxyisoguinolinyl)1–4,4-diphenylheptane (Compound II. Scheme 2)

To a solution of 7-amino-4,4-diphenylheptan-1-ol (1.016 g) (Compound 6, Scheme 2) in methylene chloride (10 mL) was added at 0° C. methanesulfonyl chloride (0.22 mL)

followed by triethylamine (0.5 mL). The solution was stirred at 0° C. for 30 min. The reaction mixture was washed with 0.5 N citric acid, water and brine. The organic phase was dried and concentrated in vacuo to give the desired product as an oil (1.1015 g). This was used in the next step without further purification.

To a solution of 7-[N-3-(4-fluorophenyl)propionyl]amino-4,4-diphenylheptyl mesylate (1.35 g) (Compound 9, Scheme 2) in acetonitrile (25 mL) was added in the dark 1,2,3,4-tetrahydro-1-cyclopropyl-6,7-dimethoxy-isoquinoline hydroiodide (0.958 g) and triethylamine (2 n-lL). The mixture was kept in the dark and heated under reflux overnight. The reaction mixture was cooled to rt and concentrated in vacuo. The residue was dissolved in ethyl acetate and the solution was washed with water and brine, dried ($Na_2SO_4$) and concentrated in vacuo. The foamy residue was purified by a silica gel column chromatography eluting with (98:2) methylene chloride/methanol. This yielded 7-[N-3-(4-fluorophenyl)propionyl]amino-1-[N-(1,2,3,4-tetrahydro-1-cyclopropyl-6,7-dimethoxy-isoquinolinyl)]-4,4-diphenylheptane (0.47 g): MS showed $(M+H)^+$ @ 649; $^1$H-NMR ($CDCl_3$, δ): 0.22–0.3 (m, 1H), 0.5–0.6 (m, 1H,), 0.92–1.25 (m. 3H), 1.98–2.07 (m, 4H), 2.3–2.42 (m, 2H), 2.42–2.95 (m, 12H), 3.08–3.3 (m, 3H), 3.83 (s, 6H). 6.53 (s, 1H), 6.6 (s, 1H), 6.86–6.98 (m, 2H), 7.07–7.3 (m. 12H). This compound was dissolved in methanol/HCl, the solution was concentrated in vacuo and the residue was dissolved in (1:1) acetonitrile/water to give 7-[N-3-(4-fluorophenyl-propionyl)]amino-1-[N-(1,2,3,4-tetrahydro-1-cyclopropyl-6,7-dimethoxy-isoquinolinyl)]-4,4-diphenylheptane hydrochloride (0.470 g): mp 122–129° C.; IR ($CHCl_3$) v 3300, 2942, 1646 $cm^{-1}$; Anal. Calcd for $C_{42}H_{49}N_2O_3F$·HCl: C. 73.61: H. 7.35; N, 4.09; Found: C, 73.73; H, 7.21; N. 3.86.

Example 5

7-[N-3-(4-Fluorophenyl)Propionyl]amino-1-[N-(1,2,3,4-tetrahydro-1-ethyl-6.7-dimethoxyisoquinolinyl)]1–4.4-diphenylheptane hydrochloride 1,2,3,4-Tetrahydro-1-ethyl-6,7-dimethoxyisoquinoline was prepared by a procedure analogous to that described in example 4 for 1,2,3,4-tetrahydro-1-cyclopropyl-6,7-dimethoxyisoquinoline but substituting in the first step propionyl chloride for cyclopropyl-carbonyl chloride.

1,2,3,4-tetrahydro-1-ethyl-6,7-dimethoxyisoquinoline (0.195 g) was reacted with 7-[N-3-(4-fluorophenyl)propionyl]amino-4,4-diphenylheptan-1-al (0.4182 g) in the presence of sodium cyanoborohydride as described in example 1 to give the desired product 7-[N-3-(4-fluorophenyl)propionyl] 1-[N-(1,2,3,4-tetrahydro-1-ethyl-6,7-dimetoxyisoquinolinyl)]-4,4-diphenylheptane as a glassy residue (0.0685 g): MS showed (M+H) +(637; $^1$H-NMR ($CDCl_3$, δ): 0.85–0.93 (t, 3H), 1.05–1.08 (m, 4H), 1.55–1.75 (m, 4H), 2.0–2.17 (m, 4H), 2.3–2.40 (t, 2H), 2.40–2.55 (m, 4H), 2.87–2.93 (t, 2H), 2.97–3.31 (m, 3H), 3.93 (s, 6H), 6.47 (s, 1H), 6.53 (s, 1H), 6.86–6.98 (t, 2H), 7.08–7.30 (m, 12H). The hydrochloride salt of the desired product was prepared as described in example 1 to give 7-[N-3-(4-fluorophenylpropionyl]amino-1-[N-(1,2,3,4-tetrahydro-1-ethyl-6,7-dimethoxyisoquinolinyl)]-4,4-diphenylheptane hydrochloride: mp 98–105° C.; IR ($CHCl_3$) U 3300, 2942, 1646 $cm^{-1}$; Anal. Calcd for $C_{41}H_{49}N_2O_3F$·HCl: C, 73.13; H, 7.48; N, 4.16; Found: C, 77.21; H, 7.79; N, 4.35.

Example 6

7-[N-3-(4-Fluorophenylpropionyl]amino-1-[N-(1,2,3,4-tetrahydro-1-isopropyl-6.7-dimethoxyisoquinolinyl)]1–4.4-diphenylheptane hydrochloride 1,2,3,4-Tetrahydro-1-isopropyl-6,7-dimethoxyisoquinoline was prepared by a procedure analogous to that described in example 4 for 1.2,3,4-tetrahydro-1-cyclopropyl-6,7-dimethoxy- isoquinoline but substituting in the first step isobutyryl chloride for cyclopropylcarbonyl chloride.

The 1,2,3,4-tetrahydro-1-isopropyl-6,7-dimethoxyisoquinoline was reacted with 7-[N-3-(4-fluorophenyl)propionyl]amino-4,4-diphenylheptan-1-al in the presence of sodium cyanoborohydride as described in example 1 to give the desired product as glassy residue (0.135 g): MS showed $(M+H)^+$ @ 651; $^1$H-NMR ($CDCl_3$, δ): 0.8–0.88 (d, 3H). 0.92–1.02 (d. 3H). 1.02–1.20 (m. 3H). 1.52–1.70 (mn, 2H), 1.7–1.9 (m. 1H) 1.97–2.2 (m. 4H), 2.3–2.50 (m. 4H). 2.50–2.72 (m, 2H), 2.85–2.96 (m, 3H), 3.02–3.20 (m, 3H), 3.8–3.9 (two s, 6H), 5.08 (broad s, 1H), 6.43 (s. 1H). 6.53 (s, 1H), 6.9–6.97 (m, 2H), 7.05–7.32 (m, 12H). The hydrochloride salt was prepared as in example I to give 7-[N-3-(4-fluorophenyl)propionyl]amino-1-[N-(1,2,3,4-tetra- hydro-1-isopropyl-6,7-dimethoxyisoquinolinyl)]-4,4-diphenylheptane hydrochloride: mp 96–103 ° C.; IR ($CHCl_3$) U 3350, 2950, 1650, 1510 $cm^{-1}$.

Example 7

7-[N-3-(4-Fluorophenyl)propionyl]amino-1-[N-(1,2,3,4-tetrahydro-1-phenyl-6,7-dimethoxyisoquinolinyl)]1–4.4-diphenylheptane hydrochloride 1,2,3,4-Tetrahydro-1-phenyl-6,7-dimethoxyisoquinoline was prepared by a procedure analogous to that described in example 4 for 1,2,3,4-tetrahydro-1-cyclopropyl-6,7-dimethoxy- isoquinoline but substituting in the first step benzoyl chloride for cyclopropylcarbonyl chloride. The 1,2,3,4-tetrahydro-1-phenyl-6,7-dimethoxyisoquinolinyl was reacted with 7-[N-3-(4-fluorophenyl)propionyl]amino-4,4-diphenylheptan-1-al in the presence of sodium cyanoborohydride as described in example 1 to give the desired product as glassy residue: MS showed $(M+H)^+$ @ 685; $^1$H-NMR ($CDCl_3$, δ): 1.0–1.2 (m, 4H), 1.65–1.75 (m, 1H), 1.95–2.05 (m, 2H), 2.06–2.15 ((m, 1H), 2.15–2.25 (m, 1H), 2.32–2.36 (t, 2H), 2.36–2.45 (m, 2H), 2.62–2.70 (m, 1H), 2.85–2.95 (m, 4H), 3.08–3.17 (q, 2H), 3.58 (s, 3H), 3.83 (s, 3H), 4.36 (s, 1H), 5.01 (broad t, 1H), 6.13 (s, 1H), 6.58 (s, 1H), 6.88–6.94 (m, 2H), 7.06–7.33 (m, 17H); IR ($CHCl_3$) u 3300, 2950, 1645, 1505 $cm^{-1}$. The hydrochloride salt was prepared as in example 1 to give 7-[N-3-(4-fluorophenylpropionyl]amino-1-[N-(1,2,3,4-tetrahydro-1-phenyl-6,7-dimethoxy- isoquinolinyl)]-4,4-diphenylheptane hydrochloride: mp 117–120° C.; Anal. Calcd for $C_{45}H_{49}N_2O_3F$·HCl 0.5$H_2O$: C, 74.0; H. 7.30; N. 3.83; Found: C. 73.14; H, 6.74; N, 3.71.

Example 8

7-[N-3-(4-Fluorophenyl)propionyl]amino-1-[N-(1,2,3,4-tetrahydro-1-cyclopentyl-6.7-dimethoxyisoguinolinyl)]-4,4-diphenylheptane hydrochloride 1,2,3,4-Tetrahydro-1-cyclopentyl-6,7-dimethoxyisoquinoline was prepared by a procedure analogous to that described in example 4 for 1,2,3,4-tetrahydro-1-cyclopropyl-6,7- dimethoxyisoquinoline but substituting in the first step cyclopentylcarbonyl chloride for cyclopropylcarbonyl chloride.

The 1,2,3,4-tetrahydro-1-cyclopenty,l-6,7-dimethoxyisoquinoline was reacted with 7-[N-3-(4-fluorophenyl)propionyl]amino-4,4-diphenylheptan-1-al in the presence of sodium cyanoborohydride as described in example 1 to give the desired product as a solid foam: MS showed (M+H)⁺ @ 677; ¹H-NMR (CDCl₃, δ): 1.05–1.72 (m, 12H). 1.75–2.17 (m, 6H.), 2.28–256 (broad m, 5H), 2.65–2.85 (m, 2H), 2.85–2.96 (t. 2H1), 3.10–3.35 (m, 3H), 3.78–3.88 (two s, 6H), 6.42 (s, 1H), 6.52 (s, 1H), 6.88–6.98 (m, 2H), 7.05–7.30 (m, 12H); IR (KBr) u 3450, 2950, 1650, 1510 cm⁻¹. The hydrochloride salt was prepared as in example 1 to give 7-[N-3-(4-fluoro- phenyl)propionyl]-1-[N-(1,2,3,4-tetrahydro-1-cyclopentyl-6,7-dimethoxyisoquinolinyl)]-4,4- diphenylheptane hydrochloride: mp 92° C. (dec.); Anal. Calcd for $C_{44}H_{53}N_2O_3F^1HCl\cdot0.5H_2O$: C, 73.15; H, 7.67; N, 3.87; Found: C, 73.45; H, 7.78; N, 3.87.

Example 9

7-[N-3-(4-Fluorophenyl)propionyl]amino-1-[N-(1,2,3,4-tetrahydro-1-cyclobutyl-6,7-dimethoxnisoguinolinyl)]1–4,4-diphenalhentane hydrochloride 1,2,3,4-Tetrahydro-1-cyclobutyl-6,7-dimethoxyisoquinoline was prepared by a procedure analogous to that described in example 4 for 1,2,3,4-tetrahydro-1-cyclopropyl-6,7-dimethoxy- isoquinoline but substituting in the first step cyclobutylcarbonyl chloride for cyclopropylcarbonyl chloride.

The 1,2,3,4-tetrahydro-1-cyclobutyl-6,7-dimethoxyisoquinoline was reacted with 7-[N-3-(4-fluorophenyl)propionyl]amino-4,4-diphenylheptan-1-al in the presence of sodium cyanoborohydride as described in example 1 to give the desired product as a solid foam: MS showed (M+H)⁺ @ 663; ¹H-NMR (CDCl₃, δ): 1.05–1.28 (m, 4H), 1.62–2.18 (m, lOH), 2.30–2.62 (m, 6H), 2.65–2.82 (m, 2H), 2.83–2.95 (t, 2H), 3.02–3.25 (m, 4H), 3.80–3.88 (two s, 6H), 6.45 (s, 1H), 6.53 (s, 1H), 6.88–6.98 (m, 2H), 7.08–7.32 (m, 12H); IR (KBr) u 3415, 2937, 1646, 1510 cm⁻¹c The hydrochloride salt was prepared as in example I to give 7-[N-3-(4-fluorophenyl- propionyl]-1-[N-(1,2,3,4-tetrahydro-1-cyclobutyl-6,7-dimethoxyisoquinolinyl)]-4,4-diphenyl- heptane hydrochloride: mp 112–121° C. (dec.); Anal. Calcd for $C_{43}H_5IN_2O_3F^1HCl2H_2O$: C, 72.88; H, 6.99; N, 3.46; Found: C, 72.56; H, 7.38; N, 3.83.

Example 10

7-[N-3-(4-Fluorophenyl)propionyl]amino-1-[N-(1,2,3,4-tetrahydro-1-cyclohexyl- 6,7-dimethoxyisoguinolinyl)1–4.4-diphenylheptane hydrochloride 1,2,3,4-Tetrahydro-1-hexyl-6,7-dimethoxyisoquinoline was prepared by a procedure analogous to that described in example 4 for 1,2,3,4-tetrahydro-1-cyclopropyl-6,7-dimethoxyisoquinoline but substituting in the first step 2-methoxyacetyl chloride for cyclopropylcarbonyl chloride.

The 1,2,3,4-tetrahydro-1-cyclohexyl-6,7-dimethoxyisoquinoline was reacted with 7-[N-3-(4-fluorophenyl)propionyl] amino-4,4-diphenylheptan-1-al in the presence of sodium cyanoborohydride as described in example 1 to give the desired product as a solid foam: MS showed (M+H)⁺ @ 691; ¹H-NMR (CDCl₃, δ): 0.8–1.3 (m, 8H), 1.3–1.8 (m, 7H), 1.85–2.2 (m, 5H), 2.3–2.45 (m, 5H), 2.5–2.75 (m, 2H), 2.84–3.0 (m, 3H), 3.03–3.2 (q, 2H), 3.83 (two s, 6H), 5.06 (broad s, 1H), 6.39 (s, 1H), 6.53 (s, 1H), 6.87–6.98 (m, 2H), 7.08–7.32 (m, 12H); IR (KBr) u 3415, 2937, 1646, 1510 cm⁻¹. The hydrochloride salt was prepared as in example 1 to give 7-[N-3-(4-fluorophenyl)propionyl] amino-1-[N-(1,2,3,4-tetrahydro-1-cyclohexyl-6,7-dimethoxy- isoquinolinyl)]-4,4-diphenylheptane hydrochloride: mp 104° C.; Anal. Calcd for $C_{45}H_{55}N_2O_3F^1HCl$: C, 74.30; H, 7.75; N, 3.85; Found: C, 73.86; H, 7.83; N.3.63.

Example 11

7-[N-3-(4-Fluorophenyl)propionyl]amino-1-[N-(1,2,3,4-tetrahydro-1-cyanomethyl- 6,7-dimethoxyisoguinolinyl)1–4.4-diphenylheptane hydrochloride 1,2,3,4-Tetrahydro-1-cyanomethylene-6,7-dimethoxyisoquinoline was reacted with 7-[N-3-(4-fluorophenyl)propionyl]amino-4,4-diphenylheptan-1-al in the presence of sodium cyanoborohydride as described in example 1 to give the desired product as a clear film: MS showed (M+H)⁺ @ 648; ¹H-NMR (CDCl₃, δ): 1.08–1.3 (m,4H), 2.02–2.12 (m, 2H), 2.12–2.25 (m, 2H), 2.32–2.40 (t, 2H), 2.45–2.80 (m, 7H), 2.85–3.0 (m, 3H), 3.06–3.2 (m, 2H), 3.75–3.85 (m, 7H), 5.38 (broad m, 1H), 6.75 (d, 2H), 6.88–6.95 (m, 2H), 7.10–7.30 (m, 12H); IR (CHCl₃) ν 3400, 2939, 2240, 1650, 1510 cm⁻¹. The hydrochloride salt was prepared as in example 1 to give 7-A[N-3-(4-fluorophenyl)propionyl]amino-1-[N-(1,2,3 .4-tetrahydro-1-cyanomethyl-6,7-di-methoxyisoquinolinyl)]-4,4-diphenylheptane hydrochloride: mp 106–114° C.; Anal. Calcd for $C_{41}H_{46}N_3O_3F\cdot HCl$: C, 71.97; H. 6.92; N, 6.14; Found: C, 71.82; H. 6.86; N. 5.95.

Example 12

7-[N-3-(4-Fluorophenyl)propionyl]amino-1-[N-(1,2,3,4-tetrahydro-1-methoxymethyl- 6,7-dimethoxyisoguinolinyl)]-4,4-diphenylhelptane hydrochloride 1,2,3,4-Tetrahydro-1-methoxymethyl-6,7-dimethoxyisoquinoline was prepared by a procedure analogous to that described in example 4 for 1,2,3,4-tetrahydro-1-cyclopropyl- 6,7-dimethoxy-isoquinoline but substituting in the first step 2-methoxyacetyl chloride for cyclopropylcarbonyl chloride.

The 1,2,3,4-tetrahydro-1-methoxymethyl-6,7-dimethoxyisoquinoline was reacted with 7-[N-3-(4-fluorophenyl)propionyl]amino-4,4-diphenylheptan-1-al in the presence of sodium cyanoborohydride as described in example 1 to give the desired product as a clear film: MS showed (M+H)⁺ @ 653; ¹H-NMR (CDCl₃, δ): 1.1–1.3 (m, 2H), 1.4–1.7 (broad m, 3H), 2.0–2.22 (m, 4H), 2.45–2.57 (t, 2H), 2.75–3.0 (m, 5H), 3.15 –3.28 (m, 4H), 3.37 (broad s, 3H), 3.5–3.65 (m, 2H), 3.65–3.8 (broad m, 1H), 3.8–3.88 (two s, 6H), 3.98–4.10 (broad m, 1H), 6.45 (s, 1H), 6.59 (s, 1H), 6.88–6.97 (t, 2H), 7.10–7.30 (m, 12H); IR (KBr) u 3331, 2937, 2240, 1646, 1510 cm⁻¹. The hydrochloride salt was prepared as in example 1 to give 7-[N-3-(4-fluorophenyl)propionyl]- amino-1-[N-(1,2,3,4-tetrahydro-1-methoxymethyl-6,7-dimethoxyisoquinolinyl)]-4,4-diphenyl- heptane hydrochloride: mp 102–110° C. (dec.); Anal. Calcd for $C_{41}H_{50}N_2O_4F2HCl$: C, 67.75; H, 7.21; N, 3.85; Found: C, 67.39; H, 6.78; N, 4.22.

Example 13

7-[N-3-(4-Fluorophenyl)propionyl]amino-1-[N-(1,2,3,4-tetrahydro-1-benzyloxymethyl- 6,7-dimethoxyisoguinolinyl)1–4.4-diphenylhelptane hydrochloride 1,2,3,4-Tetrahydro-1-benzyloxymethyl-6,7-dimethoxyisoquinoline hydroiodide was prepared by a procedure analogous to that described in step 4 of example 4 but substituting 1,2,3,4-tetra- hydro-1-benzyloxymethyl-6,7-dimethoxyisoquino line for 1,2,3,4-tetrahydro-1-cyclopropyl- 6,7-dimethoxyisoquinoline.

The 1,2,3,4-tetrahydro-1-benzyloxymethyl-6,7-dimethoxyisoquinoline hydroiodide was reacted with 7-[N-3-(4-fluorophenyl)propionyl]amino-4,4-diphenylheptyl mesylate as described in step 5 of example 4 to give the desired product as a clear film: MS showed (M+H)$^+$ @ 730; $^1$H-NMR (CDCl$_3$, δ): 1.05–1.33 (rn, 4H), 1.98–2.20 (m. 4H), 2.3–2.38 (t, 2H), 2.38–2.8 (m, 5H), 3.0–3.2 (m, 3H). 3.48–3.60 (m, 1H), 3.72 (m, 2H). 3.75 (s, 3H), 3.83 (s. 3H), 4.43–4.55 (q, 2H), 5.28 (broad s, 1H). 6.53 (s. 1H), 6.58 (s, 1H), 6.85–6.95 (m, 2H), 7.05–7.34 (m, 17H). The hydrochloride salt was prepared as in example 4 to give 7-[N-3-(4-fluorophenyl-propionyl)]- amino-1-[N-( I ,2,3,4-tetrahydro-1-benzyloxymethyl-6,7-dimethoxyisoquinolinyl)]-4,4-diphenyl- heptane hydrochloride: mp 118–133° C. (dec.); IR (MIC) u 3330, 2950, 1650, 1510 cm$^{-1}$; Anal. Calcd for C$_{47}$H$_{53}$N$_2$O$_4$F HCl. 1.25 H$_2$O: C, 71.64; H, 7.22; N, 3.55; Found: C, 71.85; H, 7.09; N, 3.69.

Example 14

7-[N-3-(4-Fluorophenyl)propionyl]amino-1-[N-(1,2, 3,4-tetrahydro-1-(4-methoxyphenyl)- 6,7-dimethoxyisoguinolinyl)1–4.4-diihenylhentane hydrochloride 1,2,3,4-Tetrahydro-1-(4-methoxyphenyl)-6,7-dimethoxyisoquinoline was prepared by a procedure analogous to that described in example 7 for 1,2,3,4-tetrahydro-1-phenyl-6,7-di- methoxyisoquinoline, but substituting in the first step 4-methoxybenzoic acid for benzoic acid. The 1,2,3,4-tetrahydro-1-(4-methoxyphenyl)-6,7-dimethoxyisoquinoline was reacted with 7-[N-3-(4-fluorophenyl)propionyl]amino-4,4-diphenylheptanal in the presence of sodium cyanoborohydride as described in example 1 to give the desired product as a clear film: MS showed (M+H)$^+$ (715; $^1$H-NMR (CDCl$_3$, δ): 1.0–1.2 (m, 3H), 1.65–1.78 (m, 2H), 1.93–2.26 (m, 4H), 2.3–2,48 (m, 4H), 2.6–2.75 (m, 1H), 2.82–2.97 (m, 4H), 3.06–3.18 (q, 2H), 3.6 (s, 3H), 3.83 (s, 3H), 4.33 (broad s, 1H), 5.07 (broad m, 1H), 6.12 (s, 1H), 6.57 (s, 1H), 6.78–6.98 (m, 4H), 7.05–7.32 (m, 14H); IR (film) u 3300,2950, 1650, 1510cmi. The hydrochloride salt was prepared as in example 4 to give 7-[N-3-(4-fluorophenyl)propionyl]amino-1-[N-(1,2,3,4-tetra- hydro-1-(4-methoxyphenyl)-6,7-dimethoxyisoquinolinyl)]-4,4-diphenylheptane hydrochloride: mp 114–120° C.; Anal. Calcd for C$_{46}$H$_5$,N$_2$O$_4$F HC1. 0.5 H$_2$O: C, 72.66; H, 7.20; N, 3.68; Found: C, 72.33; H, 6.82; N, 3.50.

Example 15

7-[N-3-(4-Fluorophenyl)propionyl]amino-1-[N-(1.2.3 .4-tetrahydro-1-(4-aminophenyl)- 6,7-dimethoxyisoguinolinyl)1–4.4-diphenylheptane dihydrochloride 1,2,3,4-Tetrahydro-1-(4-nitrophenyl)-6,7-dimethoxyisoquinoline was prepared by a procedure analogous to that described in example 7 for 1,2,3,4-tetrahydro-1-phenyl-6,7-di- methoxyisoquinoline, but substituting in the first step 4-nitrobenzoic acid for benzoic acid.

The 1,2,3,4-tetrahydro-1-(4-nitrophenyl)-6,7-dimethoxyisoquinoline was reacted %Path 7-[N-3-(4-fluorophenyl)propionyl]amino-4,4-diphenylheptanal in the presence of sodium cyanoborohydride as described in example 1 to give 7-[N-3-(4-fluoropheny)lpropionyl]-1-[N-(1,2,3,4-tetrahydro-1-(4-nitrophenyl)-6,7-dimethoxyisoquinolinyl)]-4,4-diphenylheptane as a solid: MS showed (M+H)$^+$ @ 730; $^1$H-NMR (CDCl$_3$, δ): 0.97–1.2 (mn, 4H), 1.6–1.77 (m, 1H), 1.93–2.12 (m, 2H), 2.18–2.48 (m, 6H), 2.6–2.75 (m, 1H), 2.8–3.0 (m, 4H), 3.03–3.16 (q. 2H), 3.59 (s, 3H), 3.85 (s, 3H), 4.48 (s, 1H), 5.0–5.08 (m, 1H), 6.04 (s, 1H), 6.6 (s, 1H), 6.87–6.96 (m, 2H), 7.03–7.3 (m, 12H), 7.33–7.38 (d, 2H). This compound was dissolved in methanol and hydrogenated in the presence of 1 0% Pd/C under 4 atm pressure of hydrogen gas for 21 hr. The crude product was purified by preparative HPLC to give 7-[N-3-(4-fluorophenyl)propionyl]- amino-1-[N-(1,2,3,4-tetrahydro-1-(4-aminophenyl)-6,7-dimethoxyisoquinolinyl)]-4,4-di- phenylheptane was obtained as a yellow solid: MS showed (M+H)$^+$ @ 700. $^1$H-NMR (CDCl$_3$, δ): 0.96–1.18 (m, 4H), 1.63–1.8 (m, 1H), 1.93–2.26 (m, 4H), 2.26–2.50 (m, 4H), 2.6–2.74 (m, 1H), 2.82–2.95 (m, 4H), 3.03–3.18 (m, 2H), 3.62 (s, 3H), 3.83 (s, 1H) 4.26 (brs, 1H), 5.05–5.15 (m, 1H), 6.18 (s, 1H), 6.55 (s, 1H), 6.56–6.64 (d, 2H), 6.87–7.0 (m, 4H), 7.06–7.30 (m, 12H). The dihydrochloride salt was prepared as in example 4 to give 7-[N-3-(4-fluorophenyl-propionyl)]- amino-1-[N-(1,2,3,4-tetrahydro-1-(4-amino)phenyl-6,7-dimethoxyisoquinolinyl)]-4,4-diphenyl- heptane hydrochloride: mp 168–175° C.; IR (KBr) u 3269, 2934, 2578, 1635, 1612, 1510 cm$^{-1}$.

Example 16

7-[N-3-(4-Fluorophenyl)propionyl]amino-1-[N-(1,2, 3,4-tetrahydro-1-r4-(N-isonropylamino)- phenol-6,7-dimethoxyisoguinolinyl)1–4.4-diphenylheptane dihydrochloride To a solution of 7-[N-3-(4-fluorophenyl)propionyl] amino-1-[N-(1,2,3,4-tetrahydro- 1-(4-aminophenyl)-6,7-dimethoxyisoquinolinyl)]-4,4-diphenylheptane (0.168 g) in methanol (10 mL) was added acetone (0.2 mL) followed by sodium cyanoborohydride (0.031 g) and three drops of acetic acid. The mixture was stirred under nitrogen overnight and then concentrated in vacuo. The residue was taken in ethyl acetate and washed with sodium bicarbonate and brine solutions. The organic phase was dried (Na$_2$SO$_4$) and concentrated in vacuo. The crude product was purified by preparative HPLC to give 7-[N-3-(4-fluorophenyl) propionyl]amino-1- [N-(1,2,3,4-tetrahydro-1-[4-(N-isopropylamino)phenyl-6,7-dimethoxyisoquinolinyl]-4,4-diphenylheptane: MS showed (M+H)$^+$ @ 742; $^1$H-NMR (CDCl$_3$, δ): 0.98–1.16 (broad m, 4H), 1.16–1.24 (d, 6H). 1.26 (m, 1H), 1.65–1.83 (broad m. 1H). 1.93–2.26 (m, 5H), 2.26–2.50 (m, 4H), 2.6–2.75 (m, 1H). 2.8–2.97 (m, 4H), 3.04–3.18 (m. 2H), 3.61 (s. 31H), 3.83 (s, 31H). 4.28 (broad s, 1H), 5.0–5.10 (broad m 11H), 6.19 (s, 1H), 6.44–6.53 (d, 2H), 6.56 (s, 1H), 6.85–6.97 (t, 4H), 7.03- 7.30 (m, 12H). The dihydrochloride salt was prepared as in example 4 to give 7-[N-3-(4-fluoro- phenyl-propionyl]amino-1-[N-(1,2,3, 4-tetrahydro-1-[4-(N-isopropylamino)phenyl-6,7-di- methoxyisoquinolinyl]-4,4-diphenylheptane dihydrochloride: mp 153–161° C.; IR (KBr) u 3275, 2934, 2588, 2459, 1653, 1510 cm$^{-1.}$ Example 17

7-[N-3-(4-Fluorophenyl)propionyl]amino-1-[N-(1,2, 3,4-tetrahydro-1-benzyl- 6,7-dimethoxyisoguinolinyl)1–4.4-diphenylheptane hydrochloride 1,2, 3,4-Tetrahydro-1-benzyl-6,7-dimethoxyisoquinoline was prepared by a procedure analogous to that described in example 7 for 1,2,3,4-tetrahydro-1-phenyl-6,7-dimethoxy-isoquinoline but substituting in the first step phenylacetyl chloride for benzoyl chloride. The 1,2,3,4-tetrahydro-1-benzyl-6,7-dimethoxyisoquinol ine was reacted with 7-[N-3-(4-fluorophenyl)propionyl]amino-4,4-diphenylheptanal in the presence of sodium cyanoborohydride as described in example 1 to give 7-[N-3-(4-fluorophenyl)propionyl]amino 1-[N-(1,2,3,4-tetrahydro-1-benzyl-6,7-dimethoxyisoquinolinyl)]-4,4-diphenylheptane as a film: MS showed (M+H)⁺ @ 699; ¹H-NMR (CDCl₃, δ):1.0–1.22 (m, 4H), 1.62–1.92 (broad m, 1H), 1.92–2.15 (m, 4H), 2.3–2.4 (t, 2H), 2.4–2.84 (m, 5H), 2.84–2.95 (t, 2H), 3.0–3.2 (mn, 4H), 3.5 (s, 3H), 3.6–3.7 (broad t, 1H), 3.82 (s, 3H), 5.08 (broad s, 1H), 5.83 (s, 1H), 6.53 (s, 1H), 6.87–7.03 (m, 4H), 7.08–7.33 (m, 15H). The hydrochloride salt was prepared as in example 4 to give 7-[N-3-(4-fluorophenyl)propionyl]amino-1-[N-(1,2,3,4-tetrahydro-1-benzyl-6,7-dimethoxy- isoquinolinyl)]-4,4-diphenylheptane hydrochloride: mp 94–98° C.; Anal. Calcd for $C_{46}H_5lN_2O_3F^1HCl0.75\ H_2O$: C, 73.67; H, 7.32; N, 3.73; Found: C, 73.71; H, 6.96; N, 3.57.

Example 18

7-[N-3-(4-Fluorophenyl)propionyl]amino-1-[N-(1,2,3,4-tetrahydro-1-(4-chlorobenzyl)-6,7-dimethoxyisoguinolinyl)1–4.4-diphenylheptane hydrochloride 1,2,3,4-Tetrahydro-1-(4-chloro)benzyl-6,7-dimethoxyisoquinoline was prepared by a procedure analogous to that described in example 17 for 1,2,3 .4-tetrahydro-1-benzyl-6,7- dimethoxyisoquinoline, but substituting in the first step (4-chlorophenyl)acetyl chloride for phenylacetyl chloride.

The 1,2,3,4-tetrahydro-1-(4-chlorobenzyl)-6,7-dimethoxyisoquinoline was reacted with 7-[N-3-(4-fluorophenyl)propionyl]amino-4,4-diphenylheptan- al in the presence of sodium cyanoborohydride as described in example 1 to give 7-[N-3-(4-fluorophenyl)propionyl]amino-I -[N-(1,2,3,4-tetrahydro-1-(4-chlorobenzyl)-6,7-dimethoxyisoquinolinyl)]-4,4-diphenylheptane as a film: MS showed (M+H)⁺ @ 733; ¹H-NMR (CDCl₃, δ): 1.02–1.28 (broad m, 3H), 1.52- 1.74 (broad m, 5H), 1.89–2.12 (broad m, 3H), 2.3–2.85 (broad m, 7H), 2.85–2.95 (t, 2H), 3.04- 3.22 (m, 2H), 3.72–3.88 (m, 1H), 3.76 (s, 3H), 3.93 (s, 3H), 5.95 (broad s, 1H), 6.54 (s, 1H), 6.87–7.0 (m, 4H), 7.05–7.32 (m, 14H). The hydrochloride salt was prepared as in example 4 to give 7-[N-3-(4-fluorophenyl)propionyl]amino-1-[N-(1,2,3,4-tetrahydro-1-(4-chlorobenzyl)- 6,7-dimethoxyisoquinolinyl)]-4,4-diphenylheptane hydrochloride: mp 88–96° C.

Example 19

7-[N-3-(4-Fluorophenyl)propionyl]amino-1-[N-(1,2,3,4-tetrahydro-1-(4-methoxybenzyl)-6,7-dimethoxyisoguinolinyl)1–4.4-diphenylheptane hydrochloride 1,2,3,4-Tetrahydro-1-(4-methoxybenzyl)-6,7-dimethoxyisoquinoline was prepared by a procedure analogous to that described in example 17 for 1,2,3,4-tetrahydro-1-benzyl-6,7-di-methoxyisoquinoline but substituting in the first step (4-methoxyphenyl)acetyl chloride for phenacetyl chloride.

The 1,2,3,4-tetrahydro-1-(4-methoxybenzyl)-6,7-dimethoxyisoquinoline was reacted with 7-[N-3-(4-fluorophenyl)propionyl]amino-4,4-diphenylheptanal in the presence of sodium cyanoborohydride as described in example 1 to give 7-[N-3-(4-fluorophenyl)propionyl]amino-I1-N-[ 1,2,3,4-tetrahydro-1-(4-methoxybenzyl)] -6,7-dimethoxyisoquinolinyl]-4,4-diphenylheptane as a film: MS showed (M+H)⁺ @ 729; ¹H-NMR (CDCl₃, δ): 1.0–1.22 (m, 4H), 1.91–2.10 (m, 4H), 2.3–2.4 (m, 2H), 2.4–2.85 (m, 6H), 2.85–2.94 (t, 2H), 2.94–3.2 (m, 4H). 3.51–3.67 (m, 1H), 3.55 (s, 31H). 3.76 (s, 3H), 3.82 (s, 3H), 1H. (broad s, 5.13), 5.92 (s, 1H), 6.52 (s, 1H), 6.75–6.97 (m, 6H), 7.07–7.30 (m, 12H); IR (MIC) u 3300, 2950. 1650, 1510 cm⁻¹. The hydrochloride salt was prepared as in example 4 to give 7-[N-3-(4-fluorophenyl)propionyl]-1-[N-(1.2,3,4-tetrahydro-1-(4-methoxybenzyl)-6,7-dimethoxyisoquinolinyl)]-4,4-diphenylheptane hydrochloride: mp 100–108° C.

Example 20

7-[N-3-(4-Fluorophenyl)propionyl]amino-1-[N-(1,2,3,4-tetrahydro-1-phenethyl-6,7-dimethoxy -isoguinolinyl)]-4,4-diphenylheptane hydrochloride 1,2,3,4-Tetrahydro-1-phenethyl-6,7-dimethoxy-isoquinoline was prepared by a procedure analogous to that described in example 17 for 1,2,3,4-tetrahydro-1-phenethyl-6,7-dimethoxy- isoquinoline.

The 1,2,3,4-tetrahydro-1-phenethyl-6,7-dimethoxyisoquinoline was reacted with 7-[N-3-(4-fluorophenyl)propionyl]amino-4,4-diphenylheptanal in the presence of sodium cyanoboro- hydride as described in example 1to give 7-[N-3-(4-fluorophenyl)propionyl] amino-1- [N-(1,2,3,4-tetrahydro-1-phenethyl-6,7-dimethoxyisoquinolinyl)]-4,4-diphenylheptane as a film: MS showed (M+H)⁺ @ 713; ¹H-NMR (CDCl₃, δ): 1.06–1.3 (broad in, 4H), 1.8–2.25 (m, 4H), 2.25–2.53 (m, 4H), 2.53–2.78 (in, 4H), 2.83–2.93 (t, 2H) 2.98–3.19 (m, 3H), 3.34–3.43 (broad m, 1H), 3.64–3.72 (t, 1H), 3.79 (s, 3H), 3.84 (s, 3H), 3.87 (s. 1H), 3.94 (s, 1H), 4.99 (broad s, I H), 6.43 (s, 1H), 6.53 (s, 1H), 7.87–7.98 (q, 2H), 7.04–7.35 (m, 17H). The hydrochloride salt was prepared as in example 4 to give 7-[N-3-(4-fluorophenyl)propionyl]amino-1-[N-(1,2,3,4- tetrahydro-1-phenethyl-6,7-dimethoxyisoquinolinyl)]-4,4-diphenylheptane hydrochloride: mp 97–102° C.

Example 21

7-[N-3-(4-Fluorophenol)propionyl]amino-1-F(N-[1,2,3,4-tetrahydro-1-(4-aminobenzyl)- 6,7-dimethoxyisoguinolinyl)1–4.4-diphenylheptane dihydrochloride 1,2,3,4-Tetrahydro-1-(4-nitrobenzyl)-6,7-dimethoxyisoquinoline was prepared by a procedure analogous to that described in example 17 for 1,2,3,4-tetrahydro-1-benzyl-6,7- dimethoxyisoquinoline but substituting in the first step (4-nitrophenyl)acetyl chloride for phenacetyl chloride.

1,2,3,4-Tetrahydro-1-(4-nitrobenzyl)-6,7-dimethoxyisoquinoline was reacted with 7-[N-3-(4-fluorophenyl)propionyl]amino-4,4-diphenylheptanal in the presence of sodium cyanoborohydride as described in example 1 to give 7-[N-3-(4-fluorophenyl)propionyl]-1- [N-(1,2,3,4-tetrahydro-1-(4-nitrobenzyl)-6,7-dimethoxyisoquinolinyl)]-4,4-diphenylheptane as a film: MS showed (M+H)⁺ @ 744.

A solution of 7-[N-(4-fluorophenyl)propionyl]amino-1-[N-(1,2,3,4-tetrahydro- -(p-nitro)- benzyl-6,7-dimethoxyisoquinolinyl)]-4,4-diphenylheptane in methanol was hydrogenated in the presence of 10% Pd/C under 4 atm hydrogen gas pressure. The product was purified by preparative HPLC to give 7-[N-3-(4-fluorophenyl)propionyl]-1-[,V-(1,2,3,4-tetrahydro- 1-(4-aminobenzyl)-6,7-dimethoxyisoquinolinyl)]-4,4-diphenylheptane as a film: MS showed (M+H)+ @ 714. The hydrochloride salt was prepared as in example 4 to give 7-[N-3-(4-fluoro- phenyl)propionyl]-1-[N-(1,2,3,4-tetrahydro-1-(4-aminobenzyl)-6, 7-dimethoxyisoquinolinyl)]- 4,4-diphenylheptane dihydrochloride: mp 138–149° C.

Example 22

7-[N-3-(4-Fluorophenyl)propionyl]amino-1-[N-(1, 2.3,4-tetrahydro-1-aininomethyl- 6,7-dimethoxyisoguinolinyl)1–4.4-diphenylheptane dihydrochloride Step 1: 1,2,3,4-Tetrahydro-1-N-(phthalimidomethyl)-6,7-dimethoxyisoquinoline To a mixture of 3,4-dimethoxyphenethylamine (5g) and phthalimidoglycine (5.5 g) in methylene chloride (500 mL) and DMF (30 mL) was added HOBt (4.8 g) followed by triethylarnine (11 mL) and EDCI (6.82 g). The reaction mixture was stirred at rt under nitrogen overnight and then concentrated in vacuo. Ethyl acetate was added to the residue and the mixture was washed with sodium bicarbonate solution. The precipitate was filtered and dried to give [N-2-(3,4-dimethoxyphenyl)ethyl]-N-(phthalimido)acetyl amide (8.8 g): MS showed (M+H)+ @ 369.

Step 2: 3,4-dihydro-1-N-(phthalimidomethyl)-6,7-dimethoxyisoquinoline

To a stirred suspension of [N-2-(3,4-dimethoxyphenyl)ethyl]-N-(phthalimido)acetyl amide (7.35 g) in toluene was added POCl$_3$ (29.6 g). The mixture was heated under reflux overnight, then cooled to 0° C. and basified with 4N NaOH to pH 10. The organic phase was separated. The aqueous phase was extracted three times with ethyl acetate. The toluene and ethyl acetate extracts were combined, washed with brine. dried (Na$_2$SO$_4$ ) and concentrated in vacuo. The solid residue was purified by a silica gel column eluting with (98:2) methylene chloride/methanol to give as a yellow foamr 3,4-dihydro-1-N-(phthalimidomethyl)-6,7-di- methoxyisoquinoline (5.176 g): MS showed (M+H)+ @ 351; $^1$H-NMR (CDCl$_3$, δ): 2.58–2.68 (t, 2H), 3.57–3.67 (t, 2H), 3.92 (two s. 6H), 4.92 (s, 2H), 6.7 (s, 1H), 7.07 (s, 1H), 7.68–7.76 (q, 2H), 7.83–7.92 (q, 2H).

Step 3: 1.2.3 .4-tetrahydro-1-N-(phthalimidomethyl )-6,7-dimethoxyisoguinoline

To a solution of 3.4-dihydro-1–1-(phthalimidomethyl)-6, 7-dimethoxyisoquinoline (4.8 g) in methanol (250 mL) was added sodium cyanoborohydride (1.033 g). The pH of the solution was adjusted to 5 by the addition of a few drops of acetic acid. The mixture was stirred under nitrogen at rt for 2 hr and then concentrated in vacuo. The residue was taken in ethyl acetate, washed with sodium bicarbonate and brine solutions. dried and again concentrated in vacuo. The residue was purified by a silica gel column eluting with (95:5) methylene chloride/methanol to give 1,2,3,4-tetrahydro-1-N-(phthalimidomethyl)-6,7-dimethoxyisoquinoline (2.26 g): MS showed (M+H)+ @ 353; $^1$H-NMR (CDCl$_3$, δ): 1.92 (broad s, 1H), 2.64–2.75 (m, 2H), 2.92–3.01 (m, 1H), 3.25–3.38 (m, 1H), 3.81–3.92 (m, 1H), 3.85 (s, 3H), 3.89 (m, 3H), 4.02–4.12 (m, 1H), 4.24–4.32 (two d, 1H), 6.6 (s, 1H), 6.76 (s, 1H), 7.62–7.76 (q, 2H), 7.82–7.9 (q, 2H).

Step 4: 7-[N-3-(4-fluorophenyl)propionyl]amino-1-[N-(1,2, 3,4-tetrahydro-1-N-(phthalimido-methyl)-6,7- dimethoxyisoquinolinvy)1–4.4-diphenylheptane hydrochloride 1,2,3,4-Tetrahydro-1-N-(phthalimidomethyl)-6,7-dimethoxyisoquinoline was reductively alkylated with 7-[N-3-(4-fluorophenyl)propionyl]amino-4,4-diphenylheptan-1-al in the presence of sodium cyanoborohydride using the procedure described in example 1. After workup and chromatographic purification 7-[N-3-(4-fluorophenyl)propionyl] amino-1-[N-(1,2,3,4-tetrahydro-1-N-(phthalimidomethyl)-6,7-dimethoxyisoquinolinyl)]-4,4-diphenylheptane was obtained: MS showed (M+H)+ @ 768; $^1$H-NMR (CDCl$_3$, δ): 0.71–1.13 (m, 3H), 1.56–2.04 (m, SH), 2.1–2.55 (m, SH), 2.61–2.85 (m, 2H), 2.85–2.98 (t, 2H), 2.98–3.42 (m, 3H), 3.62–3.75 (dd, 1H), 3.85–3.95 (dd, 1H), 3,82 (s, 3H), 3.86 (s, 3H), 3.95–4.12 (q, 1H), 5.73–5.82 (broad m, 1H), 6.57 (s, 1H), 6.63 (s, 1H), 6.78–6.98 (m, 6H), 7.04–7.13 (m, 8H). The hydrochloride salt was prepared as in example 4 to give 7-[N-3-(4-fluorophenyl)propionyl]-1-[N-(1,2.3,4-tetrahydro-1-N-(phthalimido-methyl)-6,7-dimethoxyisoquinolinyl)]-4,4-diphenylheptane hydrochloride: mp 114–121° C. (dec); IR (MIC) u 3250, 2943, 1771, 1712, 1671, 1510 cm$^{-1}$; Anal. Calcd for C$_{48}$HiON$_3$O$_5$F,HCl: C, 71.67; H, 6.41; N, 5.22; Found: C, 71.42 H, 6.21; N, 5.38.

Step 5: 7-[N-3-(4-fluorophenyl)propionyl]amino-1-N-(1,2, 3,4-tetrahydro-1-aminomethyl-6,7-dimethoxyisoquinolinyl) 1–4.4-diphenylheptane dihydrochloride To a stirred solution of 7-[N-3-(4-fluorophenyl) propionyl]-1-[N-(1,2,3,4-tetrahydro-1-N-(phthalimidomethyl)-6,7-dimethoxyisoquinolinyl)]-4,4-diphenylheptane (0.33 g) in ethanol (3 mL) was added hydrazine hydrate (2.5 mL) and the mixture *vas heated under reflux for 90 min. The solvent and excess of reagent were removed in acuo and to the residue was added 2N HCl (2.5 mL). The mixture was stirred at rt for 2 hr and then concentrated in vacuo. The residue was purified by preparative HPLC to give 7-[N-3-(4-fluorophenyl)propionyl] amino-1-[N-(1,2,3,4-tetrahydro-1-aminomethyl-6,7-dimethoxyisoquinolinyl)]-4,4-diphenylheptane (0.150 g) as a white foam: MS showed (M+H)+ @ 768; $^1$H-NMR (CDCl$_3$, δ): 1.0–1.3 (m. 4H), 1.94–2.24 (m, 7H). 2.32–2.79 (m, 6H), 2.79–2.97 (m, 4H). 2.97–3.28 (m. 3H), 3.35–3.43 (t. 1H), 3.8 (s, 3H), 3.84 (s, 3H), 5.68–5.78 (broad t, 1H), 6.49 (s, 1H), 6.54 (s, 1H), 6.86–6.97 (t, 2H). 7.08–7.32 (m, 12H). The hydrochloride salt was prepared as in example 4 to give 7-[N-3-(4-fluorophenyl- propionyl)]amino-1-[N-(1, 2,3,4-tetrahydro-1-aminomethyl-6,7-dimethoxyisoquinolinyl)]-4,4- diphenylheptane dihydrochloride: mp 110–116° C.; Anal. Calcd for C$_{40}$H4gN$_3$O$_3$F-2HCl: C, 67.60; H, 7.09; N, 5.91; Found: C, 65.20; H, 7.12; N, 5.53.

Example 23

7-[N-3-(4-Fluorophenyl)propionyll-1-[N-(1,2,3,4-tetrahydro-1-(N-isopropylaminomethyl)-6,7-dimethoxyisoguinolinyl)]-4,4-diphenylheptane dihydrochloride To a solution of 7-[N-3-(4-fluorophenyl)propionyl]-1-[N-(1,2,3,4-tetrahydro-1-aminomethyl-6,7-dimethoxyisoquinolinyl))]-4,4-diphenylheptane (0.030 g) in methanol (2 mL) was added acetone (0.3 mL), sodium cyanoborohydride (0.004 g) and three drops of acetic acid. The mixture was stirred at rt under nitrogen for 2 hr and then concentrated in vacuo. The residue was dissolved in ethyl acetate, washed with sodium bicarbonate and brine solutions, dried (Na$_2$SO$_4$) and again concentrated in vacuo. The residue was purified by preparative HPLC to give 7-[N-3-(4-fluorophenyl)propionyl]-1-[N-(1,2,3,4-tetrahydro-1-(N-isopropylaminomethyl)-6,7- dimethoxyisoquinolinyl)]-4,4-diphenylheptane: MS showed (M+H)+ @ 680; $^1$H-NMR (CDCl$_3$, δ): 1.0–1.32 (m, 10H), 1.97–2.32 (m, 6H), 1.98–2.54 (m, 4H). 2.6–3.18 (m, 9H), 3.2–3.35 (m, 1H), 3.55–3.68 (m, 1H), 3.77 (s, 3H), 3.83 (s, 3H), 6.49 (s, 1H), 6.52 (s, 1H), 6.86–6.97 (t, 2H), 7.08–7.32 (m, 12H); IR (CHCl$_3$) u 3280, 2946, 1647, 1510 cm$^1$. The hydrochloride salt was prepared as in example 4 to give 7-[N-3-(4-fluorophenyl)propionyl]-1-[N-(1,2,3,4-tetrahydro-1-(N-iso-propylaminomethyl)-6,7-dimethoxyisoquinolinyl)]-4,4-diphenylheptane dihydrochloride: mp 114–192° C.; Anal. Calcd for C$_{43}$H$_{54}$N$_3$O$_3$F2HCl: C, 68.60; H. 7.50; N, 5.58; Found: C, 65.69; H, 7.30; N, 5.16.

Example 24

7-[N-3-(4-Fluorophenyl)propionyl]amino-1-[N-F 1, 2,3,4-tetrahydro-1-(4-N-phthalimidobutyl)-6,7-dimethoxyisoquinolinyl)]-4,4-diphenylheptane hydrochloride The synthetic procedure described in example 22 for 1,2,3,4-tetrahydro-1-N-(phthalimido- methyl)-6,7-dimethoxyisoquinolinyl)]-4,4-diphenylheptane was used but substituting 5-N-phthalimidopentanoic acid for N-phthalimidoglycine. After a silica gel column chromatography the desired product 7-[N-3-(4-fluorophenyl) propionyl]-1-[N-(1,2,3,4-tetra-hydro-1-(4-phthalimidobutyl)-6,7-dimethoxyisoquinolinyl)]-4,4-diphenylheptane was obtained: MS showed (M+H)+ @ 810; $^1$H-NMR (CDCl$_3$, δ): 1.05–1.23 (m, 4H), 1.32–1.49 (q, 2H), 1.50- 1.76 (m, 4H), 1.96–2.2 (m, 4H), 2.28–2.50 (m, 5H), 2.52–2.76 (m, 2H), 2.84–2.94 (t, 2H), 2.94–3.07 (m, 1H), 3.07–3.23 (m, 2H), 3.23–3.33 (m, 1H), 3.6–3.7 (t, 2H), 3.80 (s, 3H), 3.83 (s, 3H), 5.30–5.43 (broad t, 1H), 6.46 (s, 1H), 6.50 (s, 1H), 6.84–6.95 (m, 2H), 7.04–7.27 (m, 12H), 7.64–7.83 (m, 4H); IR (MIC) v 3280, 2939, 1770, 1712, 1670, 1653, 1510 cm$^{-1}$. The hydrochloride salt was prepared as in example 4 to give 7-[N-3-(4-fluorophenyl)propionyl]-1-[N-(1,2,3,4-tetra- hydro-1-(4-N-phthalimidobutyl)-6,7-dimethoxyisoquinolinyl)]-4,4-diphenylheptane dihydrochloride: mp 112–128° C.; Anal. Calcd for C$_5$$_1$H$_{56}$N$_3$O$_5$F$^1$HCl: C, 72.37; H, 6.79; N, 4.96; Found: C, 72.81; H, 7.01; N, 4.67.

Example 25

7-[N-3-(4-Fluorophenyl)propional]-1-[N-(1,2,3,4-tetrahydro-1-(4-aminobutyl)-6,7-dimethoxyisoquinolinyl)]-4,4-diphenylhentane dihydrochloride The synthetic procedure described in example 22 for the cleavage of the phthalimido group was adopted. After workup and preparative HPLC purification the desired product, 7-[N-(3-(4-fluorophenyl)propionyl]-1-[N-(1,2,3,4-tetrahydro-1-(4-aminobutyl)-6,7-dimethoxyisoquinolinyl)]-4,4-diphenylheptane was obtained: MS showed (M+H)+ @ 680; $^1$H-NMR (CDCl$_3$, δ): 1.04–1.29 (m, 4H), 1.31–1.76 (m, 7H), 1.94–2.20 (m, 4H), 2.30–2.42 (t, 2H), 2.42- 2.53 (q, 2H). 2.58–2.81 (m, 6H), 2.82–2.94 (t, 2H), 2.98–3.18 (m, 3H), 3.34–3.43 (m, 1H), 3.83 (s, 6H), 5.54–5.64 (m, 1H), 6.47 (s, 1H), 6.52 (s, 1H), 6.87–6.96 (m, 2H), 7.07–7.30 (m, 12H). The hydrochloride salt was prepared as in example 4 to give 7-[N-3-(4-fluorophenyl) propionyl- 1-[N-[1,2,3 .4-tetrahydro-1-(4-aminobutyl) -6,7-dimethoxyisoquinolinyl)]-4,4-diphenyl heptane dihydrochloride: mp 112–118° C.; IR (KBr) u 3410, 2936, 2835, 1646, 1510 cm$^{-1}$; Anal. Calcd for C$_{43}$Hi$_4$N$_3$O$_3$F-2HCl1.5H$_2$O: C, 66.22; H, 7.62; N, 5.38; Found: C, 65.89; H. 7.46: N. 5.21.

Example 26

7-[N-3-(4-Fluorophenyl)propionyl]-1-[N-(1,2,3,4-tetrahydro-1-(4(N-isopropylaminobutyl)-6,7-dimethoxyisoguinolinyl)1–4.4-diohenylheptane dihydrochloride To a solution of 7-[N-3-(4-fluorophenyl)propionyl]-1-[YV-(1, 2,3,4-tetrahydro-1-(4-amino- butyl)-6,7-dimethoxyisoquinolinyl)]-4,4-diphenylheptane (0.0586 g) in methanol (2 mL) was added acetone (0.3 mL), sodium cyanoborohydride (0.007 g) and one drop of acetic acid. The mixture was stirred at rt under nitrogen for 2 hr and then concentrated in vacuo. The residue was dissolved in ethyl acetate, washed with sodium bicarbonate and brine solutions, dried (Na$_2$SO$_4$) and again concentrated in vacuo. The residue was purified by preparative HPLC to give 7-[N-3-(4-fluorophenyl)propionyl]amino-1-[N-(1,2,3,4-tetrahydro-1-(4-AV-isopropyl- aminobutyl)-6,7-dimethoxyisoquinolinyl)]-4,4-diphenylheptane: MS showed (M+H)+ (722; $^1$H-NMR (CDCl$_3$, δ): 1.05 (s, 3H), 1.07 (s, 3H), 1.07–1.22 (m, 4H), 1.3–1.76 (m, 6H), 1.95–2.22 (m, 5H), 2.3–2.50 (m, 5H), 2.52–2.86 (m. 5H), 2.86–2.95 (t, 2H), 2.95–3.08 (m, 1H), 3.08–3.18 (q, 2H), 3.28–3.37 (m, 1H), 3.83 (s, 6H), 5.32–5.42 (s, 1H), 6.48 (s, 1H), 6.52 (s, 1H), 6.82–6.97 (m, 2H), 7.04–7.29 (m, 12H); IR (CHCl$_3$) u 3299, 2934, 2832, 1669, 1648, 1510 cm$^{-1}$. The hydrochloride salt was prepared as in example 4 to give 7-[N-3-(4-fluorophenyl)propionyl]- amino-1-[N-(1,2,3,4-tetrahydro-1-(4-N-isopropylaminobuty)1–6,7-dimethoxyisoquinolinyl)]-4,4-diphenylheptane: mp 118–128° C.

Example 27

7-[N-3-(4-Fluorophenyl)Propionyl]amino-1-[N-(1,2, 3,4-tetrahydro-1-[4-N-(cyclopropylmethylamino) butyII-6,7-dimethoxyisoquinolinyl)1–4.4-diphenylheptane dihydrochloride The procedure described in example 26 was used but substituting cyclopropane- carboxaldehyde in place of acetone. After purification using a silica gel columnn chromatography 7-[N-3-(4-fluorophenyl)propionyl] 1-[N-(12,3,4-tetrahydro-1-[4-N-(cyclopropylmethylamino)- butyl-6,7-dimethoxyisoquinolinyl)]-4,4-diphenylheptane was obtained: MS showed (M+H)- @ 734; $^1$H-NMR (CDCl$_3$, δ): 0.1–0.2 (m, 2H), 0.43–0.60 (m. 2H), 0.86–1.05 (m, 1H), 1.05–1.3 (m, 4H), 1.3–1.78 (m, 6H), 1.93–2.22 (m, 4H). 2.33–2.80 (m. 10H), 2.84–2.95 (t. 2H), 2.95–3.21 (m. 3H). 3.23–3.52 (m, 3H), 3.82–3.87 (two s. 6H). 5.7–5.80 (broad t, 1H). 3.48 (s. 2H), 3.51 (s. 1H). 6.87–6.98 (t. 2H), 7.08–7.32 (m. 12H). The hydrochloride salt was prepared as in example 4 to give 7-[N-3-(4-fluorophenyl)propionyl]-1-[N-( .2.3 .4-tetrahydro-1-[4-.-(cyclopropyl- methylamino) butyl]-6,7-dimethoxyisoquinolinyl)]-4,4-diphenylheptane dihydrochloride: mp 112–120° C.; IR (KBr) v 3422, 2939. 2590. 1655. 1510 cm$^{-1}$; Anal. Calcd for C$_{47}$H$_{60}$N$_3$O$_3$F-2HCl: C, 69.96; H, 7.74; N. 5.21; Found: C, 68.41; H. 7.92; N. 5.18.

Example 28

7-[N-3-(4-Fluorophenyl)propionyl]-1-[N-(1,2,3,4-tetrahydro-1-(4-N-(cyclobutylamino)butyl)-6,7-dimethoxyisoquinolinyl)1–4.4-diphenylheptane dihydrochloride The procedure described in example 26 was used but substituting cyclobutanone for acetone. After purification of the product using silica gel column chromatography 7-[N-3-(4-fluoro- phenylpropionyl)]amino-1-[N-[1,2,3,4-tetrahydro-1-[4-N-(cyclobutylamino)butyl]- 6,7-dimethoxyisoquinolinyl]-4,4-diphenylheptane was obtained: MS showed (M+H)$^+$ @ 734; $^1$H-NMR (CDCl$_3$, δ): 1.05–1.54 (m, 6H), 1.54–1.96 (m, 7H), 1.96–2.31 (m, 8H), 2.32–2.83 (m, 10H), 2.85–2.97 (t, 2H), 3.03–3.25 (3.3–3.51 (m, 1H), 3.58–3.68 (m, 1H), 3.83 (s, 3H), 3.86 (s, 3H), 4.35 (broad m, 1H), 6.0 (t, 1H), 6.51 (s, 1H), 6.54 (s, 1H), 7.07–7.32 (m, 12H); IR (KBr) u 3421, 2942, 2742, 1641, 1510 cm$^{-1}$. The hydrochloride salt was prepared as in example 4 to give 7-[N-3-(4-fluorophenyl)propionyl]-1-[N-(1,2,3,4-tetrahydro-1-[4-(N-cyclobutylamino)butyl- 6,7-dimethoxyisoquinolinyl)]-4,4- diphenylheptane: mp 121–128° C.; Anal. Calcd for C$_{47}$H$_{60}$N$_3$O$_3$F·2HCl: C, 69.96; H, 7.74; N, 5.21; Found: C, 68.76; H, 7.97; N, 5.1 1.

Example 29

7-[N-3-(4-Fluorophenyl)propionyl]-1-[N-(1,2,3,4-tetrahydro-1-[4-(N-isobutylamino)butyll-6,7-dimethoxyisoguinolinyl)1–4.4-diphenylheptane dihydrochloride The procedure described in example 26 was used but substituting isobutyraldehyde for acetone. After workup and purification by a silica gel column chromatography 7-[N-3-(4-fluoro- phenyl)propionyl]-1-[N-(1,2,3,4-tetrahydro-1-[4-(N-isobutylamino)butyl-6,7-dimethoxy- isoquinolinyl)]-4,4-diphenylheptane: MS showed (M+H)$^+$ @ 736; $^1$H-NMR (CDCl$_3$, δ): 0.82- 1.0 (m, 1H), 1.0–1.1 (dd. 6H), 1.1–1.53 (m, 4H). 1.73–1.9 (m. 4H), 1.9–2.38 (m, 8H), 2.45–2.62 (m, 2H), 2.62–2.87 (m. 4H), 2.87–3.55 (m. I OH), 3.84 (s, 31H). 3.86 (s, 3H). 4.1 (broad s. 1H). 6.51 (s. 1H), 6.55 (s. 1H). 6.84–6.98 (m. 2H). 7.03–7.29 (m. 12H); IR (KBr) U 3421. 2950, 1650. 1510 cm$^{-1}$. The hydrochloride salt was prepared as in example 4 to give 7-[N-3-(4-fluoro- phenyl)propionyl]-1-[N-1,2,3,4-tetrahydro-1-[4-(N-isobutylamino)butyl-6,7-dimethoxy- isoquinolinyl)]-4,4-diphenylheptane dichlorohydrochloride: mp 114–128° C.; Anal. Calcd for C$_{47}$H$_{62}$N$_3$O$_3$F·2HCl: C. 69.78; H, 7.97; N. 5.19; Found: C, 68.25; H, 8.06; N, 5.06.

Example 30

7-[N-3-(4-Fluorophenyl)propionyl]amino-1-[N-(1,2,3,4-tetrahydro-1-(4-N-isopentylamino)butyll-6,7-dimethoxyisoquinolinyl)1–4.4-diphenylheptane dihydrochloride The procedure described in example 26 was used but substituting isovaleryladehyde for acetone. Afterworkup and purification by a silica gel column chromatography 7-[N-3-(4-fluoro- phenyl)propionyl]amino-1-[N-([1,2,3,4-tetrahydro-1-[4-(N-isopentylamino)buty]1–6,7-dimethoxyisoquinolinyl]-4,4-diphenylheptane: MS showed (M+H)$^+$ (750; $^1$H-NMR (CDCl$_3$, δ): 0.86–0.94 (d, 6H), 0.93–0.98 (m, 1H), 1.05–1.33 (m, 4H), 1.33–1.95 (m, 8H), 1.95–2.25 (broad m, 6H)., 2.45–2.58 (m, 2H), 2.58–3.4 (broad m, I 1H), 3.38–3.53 (m, 1H), 3.67–3.8 (m, 1H), 3.84 (s, 3H), 3.86 (s, 3H), 4.02–4.12 (m, 1H), 6.54 (s, 2H), 6.7–6.78 (broad t, 1H), 6.84–6.96 (m, 2H,), 7.0–7.29 (m, 12H); IR (KBr) u 3421, 2950, 1650, 1510 cm$^{-1}$. The hydrochloride salt was prepared as in example 4 to give 7-[N-3-(4-fluorophenyl)propionyl]-1-N-(1,2,3,4-tetrahydro-1-[4-(N-isopentylaminobutyl)-6,7-dimethoxyisoquinolinyl)]-4,4-diphenylheptane dihydrochloride: mp 118–132° C.; Anal. Calcd for C$_{48}$H$_{69}$N$_3$O$_3$F·2HCl: C, 70.05; H, 8.08; N, 5.1 1; Found: C, 68.53; H, 8.46; N, 5.02.

Example 31

7-[N-3-(4-Fluorophenyl)prol)ionyl]amino-1-[N-(1,2,3,4-tetrahydro-1-(4-(N-alpha-methylbenzylamino) butyl-6,7-dimethoxyisoguinolinyl)]-4,4-diphenylheptane dihydrochloride The procedure described in example 26 was used but substituting acetophenone for acetone. After workup and purification by a silica gel column chromatography 7-[N-3-(4-fiuorophenyl)- propionyl]-1-[N-(1,23 .4-tetrahydro-1-(4-(N-alpha-methyl-benzyl)aminobutyl-6,7-dimethoxy-isoquinolinyl)]-4,4-diphenylheptane: MS showed (M+H) @ 784: $^1$H-NMR (CDCl$_3$, δ): 1.02- 1.29 (broad m, 4H). 1.29–1.78 (m. 8H). 1.94–1.77 (m. 15H). 2.93–2.97 (t, 2H). 2.97–3.23 (m, 3H). 3.40 (broad m, 1H), 3.72–3.85 (m, 1H), 3.83 (s, 6H), 6.44 (d, 1H), 6.51 (s, 1H), 6.87–6.98 (t, 2H), 7.08–7.42 (m, 19H); IR (KBr) u 3430. 2938, 2594. 1654, 1510 cm$^{-1}$. The dihydrochloride salt was prepared as in example 4 to give 7-[N-3-(4-fluorophenyl)propionyl]-amino-1-[N-(1,2,3,4- tetrahydro-1-(4-[N-alpha-methyl-benzylaminobutyl)]-6,7-dimethoxy-isoquinolny)]-4,4-diphenylheptane: mp 120–132° C.; Anal. Calcd for Cs1H$_{62}$N$_3$O$_3$F·2HCl: C, 71.48; H, 7.53; N, 4.90; Found: C, 70.11; H, 7.69; N, 4.85.

Example 32

7-[N-3-(4-Fluorophenyl)pronionyl]amino-1-N-(1,2,3,4-tetrahydro-1-(4-N. N-dicycloprovylmethylamino)butyl-6,7-dimethoxyisoguinolinyl)1–4,4-diphenylheptane dihydrochloride The procedure described in example 26 was used but substituting a large excess of cyclopropyl aldehyde acetone. After workup and silica gel column chromatography 7-[N-3-(4-fluorophenyl)-propionyl]-1-[N-(1,2,3,4-tetrahydro-1-(4-(N,N-dicyclopropo- methylamino)butyl-6,7-dimethoxyisoquinolinyl)]-4,4-diphenylheptane was obtained: MS showed (M+H)$^+$ @ 788; $^1$H-NMR (CDCl$_3$, δ): 0.03–0.17 (q, 4H), 0.45–0.55 (m, 4H), 0.8–0.95 (m, 4H), 1.05–1.22 (m, 4H), 1.22–1.75 (m, 6H), 1.95–2.2 (m, 4H), 2.3–2.5 (m, 9H), 2.53–2.77 (m, 4H), 2.83–2.99 (t, 2H), 2.93–3.02 (m, 1H), 3.02–3.19 (q, 2H), 3.26–3.36 (m, 1H), 3.83 (s, 6H), 5.23 (broad s, 1H), 6.47 (s, 1H), 6.51 (s, 1H), 6.87–6.97 (m, 2H), 7.05–7.29 (m, 12H,). 3.72–3.85 (m, 1H,), 3.83 (s, 6H), 6.44 (d, 1H), 6.51 (s, 1H), 6.87–6.98 (t, 2H), 7.08–7.42 (m, 19H); IR (KBr) u 3423, 2938, 2595, 1657, 1510 cm$^{-1}$. The hydrochloride salt was prepared as in example 4 to give 7-[N-3-(4-fluorophenyl)propionyl]amino-1-[N-(1,23,4-tetrahydro-1-(4-N,N-dicyclopropylmethylamino)-butyl-6,7-dimethoxyisoquinolinyl)]-4,4-diphenylheptane dihydrochloride: mp 118–130° C.; Anal. Calcd for C$_5$iH$_{66}$N$_3$O$_3$F·2HCl: C, 71.14; H, 7.96; N, 4.88; Found: C, 70.68; H, 8.14; N, 4.73.

Example 33

7-[N-3-(4-Fluorophenyl)propionylamino-1-[N-(1,2,3,4-tetrahydro-1-(4-N. N-dimethylamino)butyl-6,7-dimethoxyisoguinolinyl)]-4,4-diphenylheptane dihydrochloride The procedure described in example 26 was used but substituting a large excess of 37% formaldehyde for acetone. After workup and purification by a silica gel column chromatography 7-[N-3-(4-fluorophenyl)propionyl]-1-[N-(1,2,3,4-tetrahydro-1-(4-j,VN-dimethylamino)butyl-6,7- dimethoxyisoquinolinyl)]-4,4-diphenylheptane was obtained: MS showed (M+H)+ @ 708; $^1$H- NMR (CDCl$_3$, δ): 1.05–1.28 (m, 4H), 1.3–1.77 (m, 6H), 1.96–2.18 (m, 5H), 2.23 (s, 6H), 2.25 2.50 (m, 5H), 2.53–2.77 (m, 3H), 2.84–2.95 (t, 2H), 2.84–2.95 (t, 2H), 2.95–3.08 (m, 1H), 3.08- 3.19 (q, 2H), 3.28–3.39 (m, 1H), 3.83 (two s ,6H), 5.30 (broad s, 1H), 6.47 (s, 1H), 6.51 (s, 1H), 6.87–6.97 (m, 2H), 7.05–7.30 (m, 12H); IR (MIC) v 3598, 2938, 2583, 2423, 1654, 1518 cm-i. The hydrochloride salt was prepared as in example 4 to give 7-[N-3-(4-fluorophenyl)propionyl]- 1-[N-(1,2,3,4-tetrahydro-1-(4-N, N-dimethylamino)butyl-6,7-dimethoxyisoquinolinyl))-4,4- diphenylheptane dihydrochloride: mp 116–134° C.; Anal. Calcd for C$_{45}$H$_{58}$N$_3$O$_3$F2HCl: C, 69.22; H, 7.74; N, 5.38; Found: C, 68.82; H, 7.93; N, 5.27.

Example 34

7-[N-3-(4-FluoroTphenyl)propionyll-1-[N-(1,2,3,4-tetrahydro-1-(4-N-acetylamino)butyl)-6,7-dimethoxyisoguinolinyl)1–4,4-diphenylheptane hydrochloride To a solution of 7-[N-3-(4-fluorophenyl)propionyl]-1-[N-(1,2,3,4-tetrahydro-1-(4-amino- butyl)-6,7-dimethoxyisoquinolinyl)]-4,4-diphenylheptane (0.157 g) in methylene chloride (10 mL) was added acetic anhydride (lmL) and N,N-diisopropylethylamine (1 mL). The solution was stirred at rt overnight and then poured into a separatory fimnel and washed with brine. The organic phase was dried (Na$_2$SO$_4$) and concentrated in vacuo. The residue was purified by a silica gel column chromatography to give the desired product 7-[N-3-(4-fluoro- phenyl)propionyl]amino-1-[N-(1,2,3,4-tetrahydro-1-(4-N-acetylamino)butyl)-6,7-dimethoxy- isoquinolinyl)]-4,4-diphenylheptane (0.084 g): MS showed (M+H)+ (722; $^1$H-NMR (CDCl$_3$, δ): 1.02–1.33 (broad m, 4H), 1.33–1.79 (6H, m), 1.97 (3H, s), 1.96–2.2 (SH, broad m), 2.43–2.58 (2H, m), 2.63–3.0 (SH, m). 3.0–3.37 (m, 6H), 3.84 (s, 6H), 5.3 (s, 2H), 6.43 (s, 1H), 6.56 (s, IN), 6.84–6.98 (m, 2H), 7.04–7.28 (m, 12H). The hydrochloride salt was prepared as in example 4 to give 7-[N-3-(4-fluorophenyl)propionyl]amino-1-[N-(1,2,3,4-tetrahydro-1-(4-N-acetylamino)- butyl-6,7-dimethoxyisoquinolinyl)]-4,4-diphenylheptane hydrochloride: mp 115–128° C.; Anal. Calcd for C$_{45}$Hi$_6$N$_3$O$_4$F$^1$HCl: C, 71.27; H, 7.58; N, 5.54; Found: C, 69.53, H, 7.68; N. 5.41.

Example 35

7-[N-3-(4-Fluorophenyl)propionyl]amino-1-[N-(1,2,3,4-tetrahydro-1-(4-N-nicotinylamino)-butyl-6,7-dimethoxyisoguinolinyll-4,4-diphenylheptane hydrochloride To a solution of 7-[N-3-(4-fluorophenyl)propionyl]amino-1-[N-(1,2,3,4-tetrahydro- 1-(4-amino)butyl-6,7-dimethoxyisoquinolinyl)]-4,4-diphenylheptane (0.206 g) in methylene chloride (10 mL) was added nicotinic acid (0.402 g) followed by HOBt (0.4775 g), triethylamine (0.8 mL) and EDCI (0.069 g). The mixture was stirred at rt under nitrogen for two days and then was washed with sodium bicarbonate and brine solutions. The organic phase was dried (Na$_2$SO$_4$) and concentrated in vacuo to give a brown dry foam. This residue was purified by a silica gel column to yield 7-[N-3-(4-fluorophenyl)propionyl]amino-1-[N-(1, 2,3,4-tetrahydro- 1-(4-N-nicotinylamino)butyl-6,7-dimethoxyisoquinolinyl)]-4,4-diphenylheptane (0.2 g): MS showed (M+H)+ (785; $^1$H-NMR (CDCl$_3$, δ): 1.05–1.24 (broad m , 2H), 1.5–1.84 (broad m, 6H). 1.97–2.18 (m, 5H), 2.34–2.8 (broad m, 6H), 2.80–2.98 (m, 3H), 3.0–3.64 (broad m, 7H), 3.83 (s, 3H), 3.89 (s, 3H,), 5.29 (s, 2H), 6.43 (s, 1H), 6.54 (s, 1H), 6.83–7.0 (m, 2H), 7.0–7.28 (m, 12H), 7.30–7.37 (m, 1H). 8.5 (broad m, 1H), 8.66 (broad d. 1H), 9.18 (broad s, 1H); IR (MIC) u 3370, 2959, 2934, 2908, 2837, 1600, 1585, 1521 cm$^{-1}$. The hydrochloride salt was prepared as in example 4 to give 7-[N-3-(4-fluorophenyl)propionyl]amino-1-[N-(1,2,3,4-tetrahydro-1-(4-,-nicotinylamino)butyl-6,7-dimethoxyisoquinolinyl]-4,4-diphenylheptane dihydrochloride: mp 124–133° C.

Example 36

7-[N-3-(4-Fluorophenyl)propionyl]-1-[N-(1,2,3,4-tetrahydro-1-(4-N-phthalimidomethyl)cyclohexyl-6,7-dimethoxyisoguinolinyl)1–4.4-diphenylheptane hydrochloride Step 1: -[N-(3.4-Dimethoxy)phenylethyll-4-(3[N-phthalimidomethyl)cyclohexylcarbonyl amide To a stirred solution of 3,4-dimethoxyphenethylamine (3.6224 g) in methylene chloride (100 mL) was added trans-4-(N-phthalimidomethyl)cyclohexanecarboxylic acid (6.3224 g) followed by HOBt (2.9731 g), triethylamine (4.1 mL) and EDCI (4.2175 g). The reaction mixture was stirred at rt overnight and then washed with sodium bicarbonate and brine solutions. The organic phase was dried over Na$_2$SO$_4$ and concentrated in vacuo. The obtained residue was crystallized from ethyl acetate to give N-[(3,4-dimethoxy)phenylethyl]-(4-N-phthalimido- methyl)cyclohexylcarbonyl amide (5.5 g): MS showed (M+H)+ @ 451; $^1$H-NMR (d$_6$DMSO, 6): 0.85–1.06 (broad q, 2H), 1.08–1.38 (broad q, 2H), 1.54–1.76 (broad d, SH), 1.94–2.09 (m, 1H), 2.55–2.66 (t, 2H), 3.14–3.24 (q, 2H), 3.37–3.50 (d, 2H), 3.70 (s, 3H), 3 .72 (s, 3H), 6.63–6.70 (dd, 1H), 6.77 (d, 1 H), 6.8–6.88 (d, I H), 7.66–7.74 (t, I H), 7.80–7.93 (m, 3H).

Step 2: 3.4-Dihydro-1-r 4-(N-nhthalimidomethylcyclohexyl)1-6.7-dimethoxyisoguinoline To a stirred solution of N-[(3,4-dimethoxy)phenylethyl]-4-(N-phthalimidomethyl)-cyclo- hexylcarbonyl amide (4.3178 g) in benzene (200 mL) was added POCl$_3$ (10 mL) and the mixture was heated under reflux for 4 hr and then concentrated in vacuo. The residue was taken in ethyl acetate and washed with sodium bicarbonate and brine solutions. The organic phase was dried (Na$_2$SO$_4$) and concentrated in vacuo. The residue was purified by a silica gel column chromatography eluting (9:1) methylene chloride/methanol to give 3,4-dihydro-1- [(4-phthalimidomethyl)cyclohexyl]-6,7-dimethoxyisoquinoline (2.05 g): MS showed (M+H) @ 433; $^1$H-NMR (CDCl$_3$, δ): 1.13–1.32 (broad q, 2H), 1.47–1.68 (broad q. 2H), 1.82–2.05 (broad t. SH), 2.6–2.7 (t, 2H), 2.77–2.93 (broad t, 1H), 3.57–3.72 (m, 4H), 3.94 (s, 3H), 3.96 (s, 3H), 6.71 (s, 1fH), 7.03 (s, 1H), 7.67–7.77 (m, 2H), 7.8–7.92 (m, 2H).

Step 3: 1.2.3 .4-Tetrahydro-1-[4-(N-phthalimidomethyl)cyclohexyll-6,7-dimethoxyisoquinoline To a stirred solution of 3,4-dihydro-1-[(4-N-phthalimidomethyl)cyclohexyl]-6,7-dimethoxy- isoquinoline (2.05 g) in methanol (50 mL) was added sodium cyanoborohydride (0.3276 g) followed by three drops of acetic acid. The mixture was stirred at rt for 4 hr and then concentrated in vacuo. The residue was taken in ethyl acetate and washed with sodium bicarbonate and brine solutions. The organic phase was dried (Na$_2$SO$_4$) and concentrated in vacuo. The residue was purified by a silica gel column chromatographv eluting with (98:2) methylene chloride/methanol to give 1,2,3,4-tetrahydro-1-[4-(N-phthalimidomethyl)- cyclohexyl]-6,7- dimethoxyisoquinoline: MS showed (N+M) @ 435: ¹H-NMR (CDCl₃, δ): 0.91–1.24 (m. 3H). 1.32–1.52 (m, 2H), 1.52–1.92 (broad m .7H). 2.52–1.63 (td, 1H), 2.67–2.82 (m. 1H), 2.84–2.97 (m, 1H), 3.19–3.30 (m, I H), 3.50–3.58 (d. 2H), 3.87 (s. 6H), 6.56 (s, IfH), 6.61 (s. 30 1 H), 7.68–7.76 (m. 2H), 7.8–7.88 (m. 2H).

Step 4: 7-[N-3-(4-Fluorophenyl)Propionyl]amino-1-[N-(1,2,3,4-tetrahydro-1-(4-N-phthalimidomethyl)-cyclohexyl-6,7-dimethoxyisoquinolinyl)1–4.4-diphenylheptane hydrochloride To a solution of 7-[N-3-(4-fluorophenyl)propionyl] amino-4,4-diphenylheptan-1-al (0.5051 g) in methanol (50 mL) was added 1,2,3,4-tetrahydro-1-[4-(N-phthalimidomethyl)cyclohexyl]- 6,7-dimethoxyisoquinoline (0.5077 g) followed by sodium cyanoborohydride (0–0811 g) and three drops of acetic acid. The mixture was stirred under nitrogen at rt for 2 hr. The mixture was concentrated in vacuo and the residue was taken in ethyl acetate and washed with sodium bicarbonate and brine solutions. The organic phase was dried and concentrated (Na₂SO₄) in vacuo. The residue was purified by a silica gel column chromatography to give 7-[N-3-(4-fluorophenyl)propionyl] amino-1-[N-(1,2,3,4-tetrahydro-1-[4-(N-phthalimidomethyl)- cyclohexyl]-6,7-dimethoxyisoquinolinyl)]-4,4-diphenylheptane: MS showed (M+H)⁺ @ 850; ¹H-NMR (CDCl₃, δ): 0.8–1.23 (broad m, 6H), 1.32–1.83 (broad m, 6H), 1.91–2.2 (m, 6H), 2.25- 2.72 (m, 7H), 2.82–2.97 (t, 2H), 2.97–3.23 (m, 3H), 3.79 (s, 3H), 3.83 (s, 3H), 3 83–3 89 (m, 1H), 5.07 (broad t, 1H), 6.86–6.99 (m, 2H), 7.03–7.32 (m, 12H), 7.65–7.75 (m, 2H), 7.79–7.89 (m, 2H); IR (KBr) u 3397, 2929, 2852, 1772, 1714, 1653, 1509 cm⁻¹. The hydrochloride salt was prepared as in example 4 to give 7-[N-3-(4-fluorophenyl)propionyl] amino-1-[N-(1,2,3,4- tetrahydro-1-(4-N-phthalimidomethyl)cyclohexyl-6,7-dimethoxyisoquinolinyl)]-4,4-diphenyl- heptane hydrochloride: mp 108–121° C.; Anal. Calcd for C₅₄H₆₀N₃O₅F-HCl: C, 73.16; H, 6.94; N, 4.74; Found: C, 66.33; H. 6.39; N, 5.86.

Example 37

7-[N-3-(4-Fluorophenyl)propionyl]-1-[N-(1,2,3,4-tetrahydro-1-(4-aminomethylcyclohexyl)-6,7-dimethoxyisoquinolinyl)1–4.4-diphenylheptane dihydrochloride To a solution of 7-[N-3-(4-fluorophenyl)propionyl]-1-[N-(1.2.3 .4-tetrahydro-1-(4-N- phthalimidomethylcyclohexyl]-6,7-dimethoxyisoquinolinyl)]-4,4-diphenylheptane (0.795 g) in ethanol (10 mL) was added hydrazine hydrate (2 mL) and the mixture as heated under reflux for 2 hr. Methanolic HCl (5 mL) was added. the mixture was stirred at rt for 10 min and the precipitate was filtered. The filtrate was concentrated in vacuo and the residue was purified by preparative HPLC to give 7-[N-3-(4-fluorophenyl)propionyl]-1-[N-(1,2,3,4-tetrahydro- 1-(4-aminomethyl)cyclohexyl-6,7-dimethoxyisoquinolinyl)]-4,4-diphenytheptane: MS showed (M+H)⁺ @ 720. The hydrochloride salt was prepared as in example 4 to give 7-[N-3-(4-fluorophenyl)propionyl]-1-[N-(1,2,3,4-tetrahydro-1-(4-aminomethyl)cyclohexyl- 6,7-dimethoxyisoquinolinyl)]-4,4-diphenylheptane dihydrochloride.

Example 38

7-[N-3-(4-Fluorophenyl)propionyl]-1-[N-(1,2,3,4-tetrahydro-1-(4-N-(isopropylaminomethyl)cyclohexyl-6,7-dimethoxyisoquinolinyl)1–4.4-diphenylheptane dihydrochloride To a stirred solution of 7-[N-3-(4-fluorophenyl)propionyl]-1-[N-(1,2,3,4-tetrahydro- 1-(4-aminomethyl) cyclohexyl-6,7-dimethoxyisoquinolinyl)]-4,4-diphenylheptane (0.80 g) in methanol (10 mL) was added acetone (1 mL), sodium cyanoborohydride (0.0157 g) and three drops of acetic acid. The mixture was stirred under nitrogen at rt for 2 hr and concentrated in vacuo to give 7-[N-3-(4-fluorophenyl)propionyl] -1-[N-(1,2,3,4-tetrahydro-1-(4-N-isopropyl- aminomethyl)cyclohexyl-6,7-dimethoxyisoquinolinyl)]-4,4-diphenylheptane (0.125 g): MS showed (M+H)⁺ @ 762; ¹H-NMR (CDCl₃, δ): 0.77–1.31 (m, 6H), 1.26 (d, 6H), 1.31–1.73 (broad m, 4H), 1.73–1.90 (broad t, 2H), 1.9–2.22 (m, 6H), 2.3–2.8 (m, 10H), 2.8–2.92(t, 2H), 2.92–3.23 (m, 4H), 3.82 (s, 3H), 3.83 (s, 3H), 5.29 (broad t, 1H), 6.4 (s, 1H), 6.54 (s, 1H), 6.87–6.98 (t, 2H), 7.03–7.30 (m, 12H); IR (KBr) i 3400, 2950, 1740, 1510 cm⁻¹. The hydrochloride salt was prepared as in example 4 to give 7-[N-3-(4-fluorophenyl)propionyl] amino-1-[N-(1,2,3,4- tetrahydro-1-(4-(N-isopropylaminomethyl)cyclohexyl-6,7-dimethoxyisoquinolinyl)]- 4,4-diphenylheptane dihydrochloride (0.115 g): mp 114–122° C.; Anal. Calcd for C₄₉H₆₄N₃O₃F-2HCl: C. 70.49; H, 7.97; N, 5.03; Found: C, 70.73; H, 7.86; N, 5.17.

Example 39

7-[N-3-(4-Fluorophenyl)propionyl]-1-[N-(1,2,3,4-tetrahydro-1-(4-N-phthalimidomethyl)-phenyl-6,7-dimethoxyisoguinolinyl)]-4,4-diphenylheptane hydrochloride Step 1: [N-(3,4-dimethoxynhenyl)ethyl](4-[N-phthalimidomethyl)benzoyl amide The procedure described in experiment 36 was used but substituting (4-N-phathalimido- methyl)benzoic acid for trans-(4-N-phthalimidomethyl)cyclohexanecarboxylic acid in step I to give ,-[(3,4-dimethoxyphenyl)ethyl](4-N-phthalimidomethyl)benzoyl amide: MS showed (M+H) @ 445; ¹H-NMR (d₆DMSO, 6): 2.73–2.85 (m, 2H), 3.37–3.53 (m, 2H), 3.73 (s, 6H), 4.83 (s, 2H), 6.7–6.77 (dd, 1H), 6.8–6.9 (m, 2H), 7.37–7.44 (d, 1H), 7.45–7.60 (m, 1H), 7.76–7.98 (m, 6H), 8.6 (broad t, 1H).

Step 2: 3 .4-dihydro-1- F4-N-2-phthalimidomethyl)phenyll-6,7-dimethoxyisoquinoline N-[(3,4-dimethoxyphenyl)ethyl]-(4-N-phthalimidomethyl)benzoyl amide was reacted with POCl3, using same conditions as described in experiment 36, step 2, to give 3,4-dihydro-1-[4-N- phthalimidomethyl)phenyl]-6,7-dimethoxyisoquinoline: MS showed (M+H)⁺ @ 427; ¹H-NMR (CDCl₃, δ): 2.64–2.74 (m, 2H), 3.72 (s, 3H), 3.74–3.83 (m, 2H), 3.94 (s, 3H), 4.91 (s, 2H), 6.74- 6.79 (d, 2H), 7.43–7.50 (d, 2H), 7.5–7.6 (d, 2H), 7.68–7.77 (m, 2H), 7.82–7.91 (m, 2H).

Step 3: 1,2,3,4-tetrahydro-1-[(4-N-phthalimidomethyl)lhenyll-6,7-dimethoxyisoquinoline 3,4-Dihydro-1-[(4-N-phthalimidomethyl)phenyl]-6,7-dimethoxyisoquinolinyl was-treated with sodium cyanoborohydride, using same conditions as described in experiment 36, step 3, to yield 1,2,3,4-tetrahydro-1-[(4-N-phthalimidomethyl)phenyl]-6,7-dimethoxyisoquinoline: MS showed (M+H)⁺ @ 429; ¹H-NMR (CDCl₃, δ): 2.35 (broad s, 1H), 2.68–2.80 (m, 1H), 2.82–3.04 (m, 2H), 3.09–3.20 (m, 1H), 3.63 (s, 3H), 3.87 (s, 3H), 4.84 (s, 2H), 5.04 (s, 1H), 6.22 (s, 1H), 6.62 (s. 1H), 7.11–7.22 (d, 2H), 7.33–7.42 (d, 2H), 7.65–7.75 (m, 2H), 7.8–7.88 (m, 2H).

Step 4: 7-[N-3-(4-Fluorophenyl)propionyl]-1-[N-(1 .2.3.4-tetrahydro-1-(4-N- phthalimidomethyl)-phenyl-6,7-dimethoxyisoquinolinyl)]-4,4-diphenylheptanehydrochloride 1,2,3,4-Tetrahydro-1-[4-(N-phthalimidomethyl)phenyl]-6,7-dimethoxyisoquinoline was reacted with 7-[N-3-(4- fluorophenyl)propionyl]amino-4,4-diphenylheptan-1-al in the presence of sodium cyanoborohydride, using the same conditions described in experiment 36, step 4, to give 7-[N-3-(4-fluorophenyl)propionyl]amino-1-[N-(1,2,3,4-tetrahydro-1-(4-N-phthalimidomethyl)- phenyl-6,7-dimethoxyisoquinolinyl)]-4,4-diphenylheptane: MS showed (M+H)$^+$ @ 844; $^1$H- NMR (CDCl$_3$, δ): 0.94–1.25 (broad m, 4H). 1.57–1.78 (broad m, 2H). 1.89–2.48 (m, 8H), 2.56–2.77 (m. 1H). 2.77–3.0 (m. 4H), 3.02–3.20 (broad m. 2H), 3.58 (s, 3H), 3.83 (s, 3H). 4.36 (broad m, 1H). 4.77–4.92 (q. 2H), 6.10 (s. 1H), 6.56 (s, 1H). 6.82–6.96 (m, 2H), 7.0–7.4 (m. 16H), 7.67- 7.76 (m, 4H), 7.77–7.88 (m, 2H); IR (KBr) u 3308, 3055, 2939, 1769, 1716, 1668, 1510 cm$^{-1}$. The hydrochloride salt was prepared as in example 4 to give 7-[N-3-(4-fluorophenyl)propionyl]- 1-[N-(1,2,3,4-tetrahydro-1-(4-N-phthalimidomethyl)phenyl-6,7-dimethoxyisoquinolinyl)]-4,4-diphenylheptane hydrochloride: mp 114–128° C. (dec.); Anal. Calcd for C$_{54}$H$_{54}$N$_3$O$_5$F-HCl: C, 73.66; H, 6.30; N, 4.77; Found: C, 72.21; H, 6.37; N, 4.67.

Example 40

7-[N-3-(4-Fluorophenyl)propionyl]-1-[N-(1,2,3,4-tetrthydro-1-(4-aminomethylphenyl)-6,7-dimethoxyisoquinolinyl)1–4.4-diphenylheptane dihydrochloride To a solution of 7-[N-3-(4-fluorophenyl)propionyl] amino-1-[N-(1,2,3,4-tetrahydro-1-(4-(N-phthalimidomethyl)phenyl-6,7-dimethoxyisoquinolinyl)]-4,4-diphenylheptane (0.265 g) in ethanol (10 mL) was added methyl hydrazine (1 mL) and the solution was stirred at rt for 15 min and then refluxed for 1 hr. The reaction mixture was concentrated in vacuo and the residue was taken up in ethyl acetate. The solution was washed with sodium bicarbonate and brine solutions, dried (Na$_2$SO$_4$) and again concentrated in vacuo to give 7-[N-3-(4-fluorophenyl)propionyl]- amino-1-[N-(1,2,3,4-tetrahydro-1-(4-aminomethylphenyl)-6,7-dimethoxyisoquinolinyl)]-4,4- diphenylheptane as solid foam: MS showed (M+H)$^+$ @ 714; $^1$H-NMR (CDCl$_3$, δ): 0.97–1.2 (m, 4H), 1.56–1.92 (m, 3H), 1.93–2.27 (m, 4H), 2.28–2.48 (m, 4H), 2.6–2.78 (m, 1H), 2.82–2.98 (m, 4H), 3.03–3.17 (q, 2H), 3.60 (s, 3H), 3.84 (s, 3H), 3.88 (s, 2H), 4.38 (s, 1H), 5.23 (broad t, 1H), 6.14 (s, 1H), 6,58 (s, 1H), 6,84–6.96 (m, 2H), 7.03–7.30 (m, 16H). The hydrochloride salt was prepared as in example 4 to give 7-[N-3-(4-fluorophenyl)propionyl]amino-1-[NL-(1,2,3,4- -tetrahydro-1-(4-aminomethyl)phenyl-6,7-dimethoxyisoquinolinyl)]-4,4-diphenylheptane dihydrochloride: mp 126–134° C. (dec.); Anal. Calcd for C$_{46}$H;,N$_3$O$_3$F,2HCl2H$_2$O: C, 67.14; H, 7.10; N, 5.10; Found: C, 67.11; H, 7.11; N, 5.16.

Example 41

7-[N-3-(4-Fluorophenyl)propionyl]-1-[N-(1,2,3,4-tetrahydro-1-(4-(N-isopropylaminomethyl)phenyl-6,7-dimethoxyisoquinolinyl)1-4,4-diphenylheptane dihydrochloride To a solution of 7-[N-3-(4-fluorophenyl)propionyl] amino-1-[N-( I2. 3),4-tetrahydro-1-(4- aminomethyl) phenyl-6,7-dimethoxyisoquinolinyl)]-4,4-diphenylheptane (0.102 g) in methanol (15 mL) was added acetone (0.010 mL), sodium cyanoborohydride (0.010 g) and three drops of acetic acid. The reaction mixture was stirred at rt for 3 hr and then concentrated in vacuo. The residue was taken in ethyl acetate and washed with sodium bicarbonate and brine solutions. The organic phase was dried (Na7SO$_4$) and concentrated in vacuo. The residue was purified by a silica gel column to give 7-[N-3-(4-fluorophenyl)propionyl]-1-[N-(1,2,3,4-tetrahydro-1-(4-N- isopropylaminomethyl)phenyl-6,7-dimethoxyisoquinolinyl)]-4,4-diphenytheptane (0.045 g); (M+H)$^+$ (756; $^1$H-NMR (CDCl$_3$, δ): 0.9–1.1 (broad m, 2H), 1.13–1.31 (broad m, 3H), 1.33- 1.47 (d, 6H), 1.76–2.22 (broad m, 4H), 2.35–2.58 (m, 2H), 2.70–2.93 (broad m, 6H), 2.98–3.13 (broad m, 2H), 3.13–3.42 (broad m, 3H), 3.58 (s, 3H), 3.86 (s, 3H), 4.03 (s, 2H), 4.94 (broad m, 1H), 6.09 (s, 1H), 6.63 (s, 1H), 6.84–6.97 (m, 2H), 7.03–7.37 (m, 14H), 7.42–7.52 (d, 2H). The hydrochloride salt was prepared as in example 4 to give 7-[IV-3-(4-fluorophenyl)propionyl]-1-[N-(1,2,3,4-tetrahydro-1-(4-N-isopropylaminomethyl) phenyl-6,7-dimethoxyisoquinolinyl)]- 4,4-diphenylheptane dihydrochloride: mp 128–139° C. (dec.); Anal. Calcd for C$_{49}$H$_{58}$N$_3$O$_3$F-2HCl1H$_2$O: C, 69.48; H, 7.37; N, 4.96; Found: C, 69.44; H, 7.39; N, 4.94.

Example 42

7-[N-3-(4-Fluorophenol)propionyl]-1-[N-(1,2,3,4-tetrahydro-1-(4-N-cyclobutylaminomethyl)phenyl-6,7-dimethoxyisoquinolinyl)l-4,4-diphenylheptane dihydrochloride To a solution of 7-[N-3-(4-fluorophenyl)propionyl]-1-[N-(1,2,3,4-tetrahydro-1-(4-amino- methyl)phenyl-6,7-dimethoxyisoquinolinyl)]-4,4-diphenylheptane (0.10 g) in methanol (15 mL) was added cyclobutanone ((0.0108 g), sodium cyanoborohydride (0.0097 g) and three drops of acetic acid. The reaction mixture was stirred at rt for 3 hr and then concentrated in vacuo. The residue was taken in ethyl acetate and washed with sodium bicarbonate and brine solutions. The organic phase was dried (Na$_2$SO$_4$) and concentrated in vacuo. The residue was purified by a silica gel column to yield 7-[N-3-(4-fluorophenyl)propionyl]amino-1-[N-(1,2,3,4-tetrahydro-1- (4-(N-cyclobutylaminomethyl) phenyl)-6,7-dimethoxyisoquinolinyl)]-4,4-diphenylheptane (0.020 g); (M+H)$^+$ @ 768; $^1$H-NMR (CDCl$_3$, δ): 0.75–1.32 (broad m ,7H), 1.52–2.21 (m, 6H), 2.21- 2.38 (m, 2H), 2.38–2.97 (m, 8H), 2.97–3.21 (m, 2H), 3.21–3.44 (m, 2H), 3.58 (s, 3H). 3.58–3.74 (m, 1H), 3 87 (s, 3H), 3.92 (s, 2H), 5.3 (s. 1H), 6.04 (s, 1H). 6.62 (s. 1H). 6.84–6.98 (m. 2H), 7.0- 7.52 (m. 16H). The hydrochloride salt was prepared as in example 4 to give 7-[;V-3-(4-fluoro- phenyl)propionyl]-1-[IV-(1,2,3,4-tetrahydro-1-(4-N-cyclobuty-laminomethyl) phenyl-6,7-di- methoxyisoquinolinyl)]-4,4-diphenylheptane dihydrochloride: mp 121–133° C.; Anal. Calcd for C$_{50}$H$_{58}$N$_3$O$_3$F-2HC1H$_2$O: C, 69.91; H. 7.27; N. 4.89; Found: C. 69.82; H. 7.24; N, 4.87.

Example 43

7-[N-3-(4-Fluorophenyl)propionyl]-1-[N-(1,2,3,4-tetrahydro-1-(4-N-cyclopropylmethylaminomethyl) phenyl-67-dimethoxyisoquinolinyl)]-4,4-diphenylheptane dihydrochloride The procedure described in example 42 was used but substituting cyclopropylcarboxaldehyde for cyclobutanone. After workup and silica gel column purification 7-[N-3-(4-fluorophenyl)- propionyl] -1-[N-(1,2,3,4-tetrahydro-1-(4-N-cyclopropylmethyl aminomethyl)phenyl-6,7-di-methoxyisoquinolinyl)]-4,4-diphenylheptane was obtained: MS showed (M+H)$^+$ @ 768; $^1$H- NMR (CDCl$_3$, δ): 0.07–0.22 (m, 2H), 0.45–0.6 (m, 2H), 0.92–1.24 (m, 5H), 1.6 (m, 1H), 2.0–2.28 (m, 2H), 2.29–2.49 (m, 5H), 2.5–2.77 (m, 3H), 2.82–3.0 (t, 4H), 01–3.18 (q, 2H), 3.6 (s, 3H), 3.85 (s, 3H), 3.91 (s, 2H), 4.19 (broad s, 2H), 4.39 (s, 1H), 5.4 (t, 1H), 6.11 (s, 1H), 6.58 (s, 1H), 6.85- 6.97 (t, 2H), 7.0–7.34 (m, 16H). The hydrochloride salt was prepared as in example 4 to give 7-[N-3-(4-fluorophenyl)propionyl]-1-[N-(1,2,3,4-tetrahydro-1-(4-N-cyclopropylmethylaminomethyl)phenyl-6,7-dimethoxyisoquinolinyl)]-4,4-diphenylheptane dihydrochloride: mp 124- 136 ° C.; Anal. Calcd for $C_5OH_{58}N_3O_3F2HCl1H_2O$: C, 69.91; H, 7.27; N, 4.89; Found: C, 69.88; H, 7.31; N, 4.88.

Example 44

7-[N-3-(4-Fluorophenyl)propionyl]-1-[N-(1,2,3,4-tetrahydro-1-(4-N-bis-cyclopropylmethylaminomethyl)phenyl-6,7-dimethoxyisoquinolinyl)l-4,4-diphenylheptane dihydrochloride The procedure described in example 42 was adopted but using three equivalents of cyclopropylcarboxaldehyde for cyclobutanone. After workup and silica gel column chromatography 7-[N-3-(4-fluorophenyl)propionyl]-1-[N-(1,2,3 4-tetrahydro-1-(4-N-bis- cyclopropylmethylaminomethyl) phenyl-6,7-dimethoxyisoquinolinyl)]-4,4-diphenylheptane was obtained: MS shows (M+H)$^+$ (822; $^1$H-NMR (CDCl$_3$, δ): 0.25–0.36 (m, 4H), 0.66–0.80 (m. 4H), 1.0–1.18 (m, 6H), 1.66–1.81 (m, 1H), 1.9–2.22 (m, 3H), 2.29–2.83 (m, 6H), 2.83–3.22 (m, l0H). 3.61 (s. 3H). 3.85 (s, 3H), 4.11–4.33 (m. 21H), 4.62 (broad m, 1H), 5.67 (broad m, 1H), 6.11 (s, 1H), 6.61 (s, 1H), 6.82–6.97 (t, 2H), 7.01–7.37 (m, 14H), 7.37–7.50 (d, 2H). The hydrochloride salt was prepared as in example 4 to give 7-[N-3-(4-fluorophenyl)propionyl]-1-[N-(1,2,3,4-tetrahydro-1-(4-N-biscyclopropylmethylaminomethyl)phenyl-6,7-dimethoxyisoquinolinyl)]-4,4-diphenylheptane dihydrochloride: mp 118–134° C. (dec.); Anal. Calcd for $C_{54}H64N_3O_3F-2HCl1H_2O$: C, 71.30; H, 7.50; N, 4.60; Found: C, 71.08; H, 7.54; N, 4.56.

Example 45

7-[N-3-(4-Fluorophenyl)propionyl]-1-[N-(1,2,3,4-tetrahydro-1-(4-(N-acetylaminomethl)p,henyl-6,7-dimethoxyisoquinolinyl)]-4,4-diphenylheptane hydrochloride To solution of 7-[N-3-(4-fluorophenyl)propionyl]-1-[N-(1,2,3,4-tetrahydro-1-(4-amino- methyl)phenyl-6,7-dimethoxyisoquinolinyl)]-4,4-diphenylheptane (0.101 g) in methylene chloride (10 mL) was added acetic anhydride (1 mL) and diisopropylethylamine (1 mL). The reaction mixture was stirred at rt overnight and then poured into a separatory funnel and washed with sodium bicarbonate and brine solutions. The organic phase was dried and concentrated in vacuo. The residue was purified by a silica gel column chromatography to yield 7-[N-3-(4- fluorophenyl)propionyl]-1-[N-(1,2,3,4-tetrahydro-1-(4-(N-acetylaminomethyl)phenyl-6,7- dimethoxyisoquinolinyl)]-4,4-diphenylheptane (0.070 g): MS shows (M+H)$^+$ @ 756. The hydrochloride salt was prepared as in example 4 to give 7-[N-3-(4-fluorophenyl)propionyl]- amino-1-[N-(1,2,3,4-tetrahydro-1-(4-N-acetylaminomethyl)phenyl-6,7-dimethoxyiso- quinolinyl)]-4,4-diphenylheptane hydrochloride: mp 118–132 UC (dec.); Anal. Calcd for $C_{48}H_{54}N_3O_4FHCl0.75H_2O$: C, 71.53; H, 7.60; N, 5.21; Found: C, 71.19; H, 7.08; N, 5.16.

Example 46

7-[N-3-(4-Fluorophenyl)propionyl]-1-UN-(1,2,3,4-tetrahydro-1-methyl-6,7-dihydroxyisoguinolinyl) 1–4.4-diphenylheptane hydrochloride The procedure described in experiment 1 was used but substituting 1,2,3,4-tetrahy-dro- 1-methyl-6,7-dihydroxyisoquinoline for 1,2,3,4-tetrahydro-1-methyl-6,7-dimethoxyisoquinoline. After workup and purification by a silica gel column chromatography eluting with (95:5) methylene chloride/methanol 7-[N-3-(4-fluorophenyl) propionyl]-1-[N-( I ,2,3,4-tetrahydro- 1-methyl-6,7-dihydroxyisoquinolinyl)]-4,4-diphenylheptane was obtained: MS shows (M+H)$^+$ @ 595; $^1$H-NMR (CDCl$_3$, δ): 1.05–1.20 (m, 2H), 1.27 (s, 3H), 1.88–2.19 (m, 7H), 2.33–2.51 (m, 4H), 2.67–2.94 (m, 3H), 3.05–3.19 (m, 2H), 3.30 (broad s, 1H), 4.12 (broad s, 1H), 5.37 (t, I1H), 6.28 (t, 1H), 6.53 (s, 1H), 6.59 (s, iH), 6.83–6.97 (m, 2H), 7.04–7.30 (m, 12H). The hydrochloride salt was prepared as in example 4 to give 7-[N-3-(4-fluorophenyl)propionyl]-amino-1-[N-(1,2,3,4-tetrahydro-1-methyl-6,7-dihydroxyisoquinolinyl)]-4,4-diphenylheptane hydrochloride.

Example 47

7-[N-3-(4-Fluorophenyl)propionyl]-1-[N-(1,2,3,4-tetrahydro-1-methylisoquinolinyl)1–4.4-diphenylheptane hydrochloride The procedure described in experiment 1 was used but substituting 1,2,3,4-tetrahydro- 1-methylisoquinoline for 1,2,3,4-tetrahydro-1-methyl-6,7-dimethoxyisoquinoline. After workup and purification by a silica gel column chromatography eluting with (95:5) methylene chloride/methanol 7-[N-3-(4-fluorophenyl)propionyl]amino-1-[N-(1,2,3,4-tetrahydro-1-methyl- isoquinolinyl)]-4,4-diphenylheptane was obtained: MS shows (M+H)$^+$ (563; $^1$H-NMR (CDCl$_3$, δ): 1.07–1.17 (m, 2H), 1.18–1.30 (m, SH), 2.01–2.15 (m, 4H), 2.30–2.38 (t, 2H), 2.42- 2.58 (m, 2H), 2.58–2.69 (m, 2H), 2.77–2.98 (m, 4H), 3.09–3.17 (m, 2H), 3.71–3.79 (q, I1H), 5.10 (broad s, 1H), 6.88–7.29 (m, 18H); IR (KBr) u 3416, 3300, 2939, 1613, 1716, 1509 cm$^1$. The hydrochloride salt was prepared as in example 4 to give 7-[N-3-(4-fluorophenyl)propionyl]-1- [N-(1,2,3,4-tetrahydro-1-methylisoquinolinyl)]-4,4-diphenylheptane hydrochloride: mp 83–87 -C; Anal. Calcd for $C_{38}H_{43}N_2OF$, HCl 0.5H$_2$O: C, 72.30; H, 8.27; N, 5.1 1; Found: C, 72.61; H. 7.42: N. 443.

Example 48

7-[N-3-(4-Fluorophenyl)propionyl]-1-[N-(1,2,3,4-tetrahydro-1-methyl-6,7-dioxalane-isoquinolinyl) 1–4,4-dip[]henylheptane hydrochloride The procedure described in experiment 1 was used but substituting 1,2,3,4-tetrahydro-1- methyl-6,7-dioxalane-isoquinoline for 1,2,3,4-tetrahydro-1-methyl-6,7-dimethoxyisoquinoline. After workup and purification by silica gel column chromatography eluting with ethyl acetate 7-[N-3-(4-fluorophenyl)propionyl]-1-[N-(1,2,3,4-tetrahydro-1-methyl-6,7-dioxalane- isoquinolinyl)]-4,4-diphenylheptane was obtained: MS shows (M+H)$^+$ (607; $^1$H-NMR (CDCl$_3$, δ): 1.08–1.26 (m, 7H), 2.02–2.14 (m, 4H), 2.33–2.38 (t, 2H), 2.38–2.58 (m, 4H), 2.68- 2.83 (m, 1H), 2.83–2.94 (m, 3H), 3.10–3.18 (q, 2H), 3.57–3.64 (q, 1H), 5.14 (broad s, 1H), 5.88 (s, 2H), 6.48 (s, 1H), 6.51 (s, 1H), 6.89–6.97 (t, 2H), 7.08–7.30 (m, 12H) ); IR (KBr) D 3420, 3296, 2939, 1643, 1550, 1510, 1482 cm$^{-1}$. The hydrochloride salt was prepared as in example 4 to give 7-[N-3-(4-fluorophenyl)propionyl]amino-1-[N-(1,2,3,4-tetrahydro-1-methyl-6,7- dioxalane-isoquinolinyl)]-4,4-diphenylheptane hydrochloride: mp 91–95° C.; Anal. Calcd for $C_{39}H_{43}N_2O_3F$,HCL1.25H$_2$O: C, 70.36; H. 7.30; N, 4.20; Found: C, 70.49; H, 7.00; N, 4.07.

Example 49

7-[N-3-(4-Fluorophenyl)propionyl]amino-1-[N-(1,2,3,4-tetrahydro-1-methyl-6,7-dioxane-isoguinolinyl) 1–4.4-diphenylheotane hydrochloride The procedure described in experiment 1 was used but substituting 1,2,3,4-tetrahydro-1- methyl-6,7-dioxane-isoquinoline for 1,2,3,4-tetrahydro-1-methyl-6,7-dimethoxyisoquinoline. After workup and purification by silica gel column chromatography eluting with (95:5) methylene chloride/methanol to give 7-[N-3-(4-fluorophenyl)propionyl]amino-1-[N-(1,2,3,4- tetrahydro-1-methyl-6,7-dioxane-isoquinolinyl)]-4,4-diphenylheptane: MS shows (M+H)[] ( 621; $^1$H-NMR (CDCl$_3$, δ): 1.04–1.32 (m. 7H). 1.97–2.13 (m. 4H), 2.28–2.59 (m, 6H). 2.61–2.67 (m, 1H), 2.80–2.94 (m, 3H), 3.06–3.65 (m. 1H). 4.22 (s. 4H). 5.04 (broad s, 1H). 6.51 (s 1H), 6.54 (s, 1H). 6.85–6.97 (t, 2H), 7.06–7.28 (m, 12H); IR (KBr) u 3417, 3312. 2931, 2870, 1644. 1509 cm$^{-1}$. The hydrochloride salt was prepared as in example 4 to give 7-[N-3-(4-fluoro- phenyl)propionyl]amino-1-[N-( I 2,3,4-tetrahydro-1-methyl-6,7-dioxane-isoquinolinyl)]- 4,4-diphenylheptane hydrochloride, mp 104–109° C.: Anal. Calcd for C$_{40}$H$_4$iN$_0$O$_3$F·HCl·H$_2$O: C, 71.14; H. 7.16; N, 4.14; Found: C, 71.00; H. 7.21: N. 4.01.

Example 50

7-[N-3-(4-Fluorophenyl)propionyl]amino-1-[-1-(1,2,3,4-tetrahydro-1-methv,l-6-methoxyisoquinolinyl) 1–4.4-diphenylheptane hydrochloride Step 1: [N-2-(3-Methoxyphenyl)ethyllacetyl amide (Compound 12. Scheme 3)

To a stirred solution of 3-methoxyphenethylamine (3.11 g) in methylene chloride (150 mL) was added under nitrogen triethylamine (6.0 mL). acetic anhydride (2.1 mL) and DNIAP (0.126 g). The mixture was stirred at rt overnight and then consecutively washed with solutions of sodium bicarbonate, IN hydrochloric acid and brine. The organic phase was dried (iNa$_2$SO$_4$) and concentrated in vacuo to give [N-2-(3-methoxyphenyl)ethyl]acetyl amide (3.65 g) as a yellow oil: MS shows (M+H)$^+$ @ 194, (M+NH$_4$)$^+$ @ 211; $^1$H-NMR (CDCl$_3$, δ): 1.94 (s, 3H), 2.75–2.83 (t, 2H), 3.45–3.56 (q, 2H), 3.80 (s, 3H), 5.64 (broad s, 1H), 6.72–6.81 (m, 3H), 7.19–7.28 (m, 1H); IR (KBr) u 3285, 3080, 2935, 1651, 1584, 1490 cm$^{-1}$.

Step 2: 4.5-Dihydro-7-methoxy-9b-methyl-oxazolof2.3-alisoquinoline-2.3-dione (Compound 14. Scheme 3)

To a stirred solution of [N-2-(3-methoxyphenyl)ethyl]acetyl amide (3.65 g) in methylene chloride (175 mL) was added 2M oxalyl chloride solution in methylene chloride (10.4 mL) followed by a portionwise addition of FeCl$_3$ (3.68 g). The mixture was stirred at rt overnight. To the dark brown mixture was added 2N HCl (150 mL) and stirring was continued for 1 hr. The mixture was poured in a separatory finnel and the layers were separated. The organic phase was washed with brine, dried (MgSO$_4$) and concentrated in vacuo to give 1-(3-methoxy- phenethyl)-2-chlorooxazolidine-4,5-dione (3.60 g) as a dark brown solid: MS shows (M+H)$^+$ @ 248, (M+NH$_4$)$^+$ @ 265. This solid was recrystallized from ethyl acetate to give the 7-methoxy isomer (1.139 g) as the major product and the 9-methoxy isomer (0.128 g) as the minor one. The spectral data were consistent with the 7-methoxy isomer, $^1$H-NMR (CDCl$_3$, δ): 2.84–2.91 (dd, 1H), 3.10–3.20 (m, 1H), 3.48–3 .56 (m, 1H), 3.81 (s, 3H), 4.51–4.58 (dq, 1H), 6.65 (d, 1H), 6.85- 6.89 (dd, 1H) 7.2–7.25 (d, 1H); IR (KBr) u 33423, 2921, 1806, 1737 cm$^{-1}$: mp 135–136° C.; Anal. Calcd for C$_{13}$H$_{13}$NO$_4$: C, 63.15; H, 5.29; N, 5.66; Found: C, 63.01; H, 5.27; N, 5.62.

Step 3: 3.4-Dihydro-6-methoxy-1-methylisoquinoline (Compound 15. Scheme 3)

To a stirred slurry of 4,5-dihydro-7-methoxy-9b-methyl-oxazolo[2,3-a]soquinoline-2,3-dione (2.27 g) in methanol (100 mL) was added conc. H2S04 (2 mL) and the mixture was heated at 75 OC overnight and then concentrated in vacuo. The residue was partitioned between ethyl acetate and water. The organic phase was washed twice with 2N HCl. The aqueous extracts were combined and basified with NaOH solution to pH 11.0 and extracted with chloroform three times. The organic extracts were combined, dried (MgSO$_4$) and concentrated in vacuo to give 3,4-dihydro-6-methoxy-1-methylisoquinoline as a brown oil (1.503 g): MS shows (M+H)$^+$ @ 176; $^1$H-NMR (CDCl$_3$, δ): 2.36 (t, 3H), 2.65–2.73 (t. 2H). 3.59–3.69 (dt, 2H), 3.85 (s, 3$^1$H), 6.68-6.72 (d, 1H). 6.72–6.82 (dd, 1H), 7.4–7.46 (d, 1H); IR (MIC) u 2937, 2837, 1627. 1569 cm$^{-1}$.

Step 4: 1 2,3,4-Tetrahydro-6-methoxy-1-methylisoguinoline (CompoundA. Scheme 3)

To a stirred solution of 3,4-dihydro-6-methoxy-1-methylisoquinolinyl (1.503 g) in methanol (100 mL) was added sodium cyanoborohydride (1.078 g). The solution pH was adjusted to pH 4–5 by the addition of few drops of acetic acid. The reaction mixture was stirred at rt overnight and then concentrated in vacuo. The residue was partitioned between ethyl acetate and sodium bicarbonate solution. The aqueous phase was washed three times with ethyl acetate. The organic extracts were combined and washed with brine, dried (MgSO$_4$) and concentrated in vacuo. to give 1,2,3,4-tetrahydro-6-methoxy-1-methylisoquinoline (1.48 g) as brown oil: MS shows (M+H)$^+$ (178; $^1$H-NMR (CDCl$_3$, δ): 1.60–1.67 (d, 31H) 2.87–3.0 (m, 1H), 3.02–3.17 (m, 1H), 3.19–3.30 (m, 1H), 3.40–3.52 (m, 1H), 3.79 (s, 3H), 3.31–4.41 (m, 1H), 5.10 (broad s, 1H), 6.63–6.68 (d, 1H), 6.77–6.82 (dd, 1H), 7.05–7.10 (d, 1H). 1,2,3,4-Tetrahydro-6-methoxy-1-methylisoquinoline was reacted with 7-[N-3-(4-fluoro- phenyl)propionyl]amino-4,4-diphenylheptan-1-al in the presence of sodium cyanoboro-hydride using the procedure described in example 1. After workup and purification by a silica gel column chromatography 7-[N-3-(4-fluorophenyl)propionyl]amino-1-[N-(1,2,3,4-tetrahydro-1-methyl-6-methoxyisoquinolinyl)]-4,4-diphenylheptane was obtained: MS shows (M+H)$^+$ @ 593; $^1$H-NMR (CDCl$_3$, δ): 1.05–1.27 (m, 5H), 1.57–1.76 (m, 2H), 2.0–2.15 (m, 4H), 2.29–2.39 (t, 2H), 2.39–2.66 (m, 4H), 2.70–2.96 (m, 4H). 3.07–3.18 (q, 2H), 3.62–3.72 (q, 1H), 3.78 (s, 3H), 5.05 (broad t, 1H), 6.57–6.60 (d, 1H), 6.67–6.83 (dd, 1H), 6.87–6.97 (m, 3H), 7.06–7.30 (m, 12H); IR (MIC) v 3296, 2943, 1644, 1509 cm$^{31\ 1}$. The hydrochloride salt was prepared as in example 4 to give 7-[N-3-(4-fluorophenyl)propionyl]amino-1-[N-(1,2.3,4-tetrahydro-1-methyl-6-methoxy- isoquinolinyl)]-4,4-diphenylheptane hydrochloride.

Example 51

7-[N-3-(4-Fluorophenylpropionyl]-1-FA-f 1,2,3,4-tetrahydro-1-methyl-7-methoxy-isoguinolinyl)1–4.4-diphen%-lheptane hydrochloride The procedure described in experiment 50 was used but substituting 1,2,3,4-tetrahydro- 7-methoxyisoquinoline for 1,2,3,4-tetrahydro-6-methoxyisoquinoline. After workup and purification by a silica gel column chromatography 7-[N-3-(4-fluorophenyl)propionyl]-1- [N-(1,2,3,4-tetrahydro-1-methyl-7-methoxy-isoquinolinyl)]-4,4-diphenylheptane: MS shows (M+H)$^+$ @ 593; $^1$H-NMR (CDCl$_3$, δ): 1.08- 1.30 (m, 7H), 2.02–2.16 (m, 4H), 2.31

−2.38 (t, 2H), 2.40–2.62 (m, 4H), 2.70–2.80 (m, 1H), 2.86–2.97 (m, 3H), 3.09–3.18 (q, 2H), 3.64–3.72 (q, 1H), 3.78 (s, 3H), 5.14 (broad s, 1H), 6.56 (d, 1H), 6.67–6.72 (dd, 1H), 6.88–7.0 (mn, 3H, m), 7.07–7.31 (I 2H, m); IR (MI C) ) 3296, 2944, 1644, 1509 cm$^{-1}$. The hydrochloride salt was prepared as in example 4 to give 7-[N-3-(4-fluoropheny) propionyl]-1-[N-(1,2,3,4-tetrahydro-1-methyl-7-methoxyisoquinolinyl)]-4,4-diphenylheptane hydrochloride.

Example 52

7-[N-3-(4-Fluorophenyl)propionyl]-1-[N-(1,2,3,4-tetrahydro-1-methyl-7-chloro-isoguinolinyl)-4,4-dithenylhepMtane hydrochloride The procedure described in experiment 50 was used but substituting 1i,2,3,4,-tetrahydro- isoquinolinyl-1-methy-1-7-chloroisoquinoline for 1,2,3,4-tetrahydroisoquinolinyl-1-methyl-6- methoxyisoquinoline. After workup and purification by a silica gel column chromatography 7- [N-3-(4-fluoropheny)lpropionyl]-1-[N-(1,2,3,4-tetrahydro-1-methyl-7-chloro-isoquinolinyl)]-4,4 diphenylheptane was obtained: MS shows (M+H) v do597;H-NMRi (CDCl$_3$, δ): 1.05–1.25(m, 7H), 2.00–2.12 (mn, 4H), 2.3–2.37 (t, 2H), 2.37–2.60 (m, 4H), 2.70–2.82 (mn, I1H), 2.82–2.93 (m, 3)H), 3.09–3J.17 (q, 2H), 3 .60–3.68 (m, I1H), 5.02 (broad s, I1H), 6.88–7.00 (m, 3H), 7.02–7.29 (m, 14H); IR (MIC) u 3423, 3300, 2940, 1642, 1509 cm$^{31\ 1}$. The hydrochloride salt was prepared as in example 4 to give 7-cN-3l-(4-fluorophenyl)propionyl]-[N-(dI,2s,4-tetrahydro-1-methyl-7-chloroisoquinolinyl)]-4,4-diphenylheptane h ydrochloride: mp 84–88 sC; An al. Calcd for $C_{38}H_{42}N?OFCl^1HCl25H$-)O: C, 69.55; H, 6.98; N, 4.26; Found: C, 69.49; H, 6.97; N, 4.22.

Example 53

7-[N-3-(4-Fluorophenyy)propionyl]-1-[N-(1,2,3,4-tetrahydro-1-methyl-7-fluoro-isoquinolinyl)l -4,4-diphenylheptane hydrochloride The procedure described in experiment 50 -as used but substituting 1,2,3,4-tetrahydro-1- methyl-7-fluoroisoquinoline for 1. ),34-tetrahydro-1-methyl-6-methoxyisoquinoline. After workup and purification by a silica gel column chromatography 7-[N-3-(4-fluorophenyl)-30O propionyl]-1-[N-(1,2,3,4-tetrahydro-11-methyl-7-fluoroisoquinolinyl)]-4,4-diphenylheptane -was obtained: MS shows (M+H)$^+$ @ 581; $^1$H-NMR (CDCl$_3$, δ): 1.05–1.29 (m, 7H), 1.98–2.15 (m. 4H), 2.29–2.37 (t, 2H), 2.37–2.62 (m, 4H), 2.70–2.80 (m, 4H), 2.84–2.98 (m, 1H), 3.08–3.17 (q, 2H), 3.62–3.70 (q, 2H), 5.16 (broad m, 1H), 6.67–6.72 (dd, 1H), 6.75–6.82 (td, 1H), 6.88–6.95 (t, 2H), 6.95–7.02 (m, 1H), 7.05–7.20 (m, 8H), 7.20–7.28 (t, 4H); IR (MIC) u 3291, 3086, 2943, 1643, 1552, 1509, 1500 cm$^{-1}$. The hydrochloride salt was prepared as in example 4 to give 7-[N-3-(4-fluorophenyl)propionyl]-1-[N-(1,2,3,4-tetrahydro-1-methyl-7-fluoroisoquinolinyl)]-4,4- diphenylheptane hydrochloride: mp 80–84° C.; Anal. Calcd for $C_{38}H_{42}N_2OF_2$-HCl H$_2$O: C, 71.85; H, 7.13; N, 4.40; Found: C, 71.44; H, 7.08; N, 4.24.

Example 54

7-[N-3-(4-Fluorophenyl)Propionyl]-1-[N-(1,2,3,4-tetrahydro-1-methyl-7-nitro-isoquinolinyl)l-4,4-diphenylheiptane hydrochloride The procedure described in experiment 50 was used but substituting 1,2,3,4,-tetrahydro- 1-methyl-7-nitroisoquinoline for 1,2,3,4-tetrahydro-1-methyl-6-methoxyisoquinoline. After workup and purification by a silica gel column chromatography 7-[N-3-(4-fluorophenyl)-propionyl]-1-[N-(1,2,3,4-tetrahydro-1-methyl-7-nitro-isoquinolinyl)]-4,4-diphenylheptane was obtained: MS shows (M+H)$^+$ @ 608; $^1$H-NMR (CDCl$_3$, δ): 1.08–1.32 (m, 7H), 2.0–2.18 (m, 4H), 2.32–2.42 (m, 2H), 2.42–2.57 (m, 2H), 2.58–2.68 (broad m, 1H), 2.68–2.97 (t, 4H), 3.08–3.18 (q, 2H), 3.73–3.82 (m, 1H). 5.18 (broad m, 1H), 6.88–6.97 (m, 2H), 7.07–7.30 (m, 13H), 7.88–7.98 (m, 2H); IR (MIC) u 3297, 3086, 2943, 1645, 1522 cm[]$^1$. The hydrochloride salt was prepared as in example 4 to give 7-[N-3-(4-fluorophenyl)propionyl]-1-[N-(1,2,3,4-tetrahydro-1-methyl-7- nitroisoquinolinyl)]-4,4-diphenylheptane hydrochloride.

Example 55

7-[N-3-(4-Fluorophenyl)propionyl]-1-[N-(1,2,3,4-tetrahydro- 1 -methyl-7-acetylamino-isoquinolinyl) 1–4.4-diphenylheptane hydrochloride A solution of 7-[A-.3-(4-fluorophenyl)propionyl]-1-[N-(1,2,3,4-tetrahydro-1-methyl-7-nitro- isoquinolinyl)]-4,4-diphenylheptane (0.060 g) in ethyl acetate (10 mL) was hydrogenated in the presence of 10% Pd/C (0.030 g) to give 7-[N-3-(4-fluorophenyl)propionyl]-1-[N-(1,2,3,4-tetrahydro-1-methyl-7-aminoisoquinolinyl)]-4,4-diphenylheptane (0.057 g). A solution of this amine in methylene chloride (10 mL) was treated with triethylamine (0.021 mL), acetic anhydride ((0.010 mL), and catal,tic amount of DMAP and stirred at rt overnight. The reaction mixture was diluted with methylene chloride and the organic phase was washed three times with sodium bicarbonate and brine solutions, dried (Na$_2$SO$_4$) and concentrated in vacuo. The residue was purified by a silica gel column chromatography to give 7-[N-3-(4-fluorophenyl)propionyl]- amino-1-[N-(1,2,3,4-tetrahydro-1-methyl-7-acetylaminoisoquinolinyl)]-4,4-diphenylheptane (0.025 g): MS shows (M+H)$^+$ @ 620. The hydrochloride salt was prepared as in example 4 to give 7-[N-3-(4-fluorophenyl) propionyl]-1-[N-(1,2,3,4-tetrahydro-1-methyl-7-acetylamino- osoquinolinyl)]-4,4-diphenylheptane hydrochlorid: mp 114° C.; Anal. Calcd for $C_{40}H_{46}N_3OF$,HCl 1.75H$_2$O: C, 69.85; H, 7.40; N, 6.10; Found: C. 70.01; H, 7.49; N, 5.90.

Example 56

7-[N-3-(4-Fluorophenyl)propionyl]-1-[N-(1,2,3,4-tetrahydro-1-methyl-6,7-dichloro-isoquinolinyl) 1–4.4-diphenylheptane hydrochloride The procedure described in experiment 50 was used but substituting 1,2,3,4-tetrahydro-1- methyl-6,7-dichloroisoquinoline for 1,2,3,4-tetrahydroisoquinoline-1-methyl-6-methoxy- isoquinoline. After workup and purification by a silica gel column chromatography 7-[N-3-(4-fluorophenyl)propionyl]-1-[N-(1,2,3,4-tetrahydro-1-methyl-6,7-dichloro- isoquinolinyl)]-4,4-diphenylheptane was obtained: MS shows (M+H)$^+$ @ 63 1; $^1$H-NMR (CDCl$_3$, δ): 1.08–1.18 (m, 2H), 1.18–1.32 (m, 5H), 2.02–2.14 (m, 4H), 2.32–2.40 (t, 2H), 2.4–2.64 (m, 4H), 2.70–2.81 (m, 1H), 2.86–2.95 (m, 3H). 3.10–3.19 (q, 2H), 3.62–3.71 (q. 1H), 5.23 (broad s, I H), 6.89–6.97 (t, 2H), 7.07–7.30 (m, 14H); IR (KBr) u 3431. 2932, 1642, 1509 cm$^{-1}$. The hydrochloride salt was prepared as in example 4 to give 7-[N-3-(4-fluorophenyl)propionyl]-1- [N-(1,2,3,4-tetrahydro-1-methyl-6,7-dichloroisoquinolinyl)]-4,4-diphenylheptane hydrochloride.

Example 57

7-[N-3-(4-Fluorophenyl)propionyl]-1-[N-(1,2,3,4-tetrahydro-1-methyl-6-chloro-7-fluoroisoquinolinyl) 1–4.4-diphenylheptane hydrochloride

The procedure described in experiment 50 was used but substitutino 1,2,3,4.-tetrahydro-1- methyl-6-chloro-7-fluoroisoquinoline for 1,.2,3.4-tetrahydro-1-methyl-6-methoxyisoquinoline. After workup and purification by a silica gel column chromatography 7-[N-3-(4-fluorophenyl)-propionyl]-1-[N-(1,2,3,4-tetrahydro-1-methyl-6-chloro-7-fluoroisoquinolinyl)]-4,4-diphenyl- heptane was obtained: MS shows (M+H)$^+$ @ 615; $^1$H-NMR (CDCl$_3$, δ): 0.97–1.29 (m, 7H). 1.91–2.07 (m, 4H). 2.22–2.57 (m, 6H), 2.60–2.71 (m, 1H), 2.71–2.85 (m. 3H), 3 .0–3.11 (q, 2H). 3.50–3.61 (m, 1H), 5.02 (broad m, 1H), 6.7–6.74 (d, 1H), 6.81–6.89 (t, 2H), 6.97–7.22 (m, 131H): IR (KBr) u 3285, 2942, 1642, 1509 cm$^{-1}$. The hydrochloride salt was prepared as in example 4 to give 7-[N-3-(4-fluorophenyl)propionyl]-1-[N-(1 ,2,3,4-tetrahydro-1-methyl-6-chloro-7-fluoroisoquinolinyl)]-4,4-diphenylheptane hydrochloride: mp 97–99° C.; Anal. Calcd for C$_{38}$H$_{41}$N$_2$OClF,·HCl·3H$_2$O: C, 68.65; H, 6.32; N, 4.21; Found: C, 68.29; H, 6.65; N, 3.96.

Example 58

7-[N-3-(4-Fluorophenyl)propionyl]-1-[N-(1,2,3,4-tetrahydro-1-methYI-6,7-diacetoxyisoquinolinyl)]-4,4-dilhenylheptane

A methylene chloride solution of the dihydroxy compound (0.250 g), obtained from experiment 46, was treated with acetic anhydride, triethylamine and DMAP at rt overnight. After workup and purification by a silica gel column chromatography 7-[N-3-(4-fluorophenyl)- propionyl]-1-[N-(1,2,3,4-tetrahydro-1-methyl-6,7-diacetoxyisoquinolinyl)]-4,4-diphenylheptane was obtained: MS shows (M+H)$^+$ @ 679; $^1$H-NMR (CDCl$_3$, δ): 1.08–1.32 (m, 7H), 2.0–2.16 (m, 4H), 2.32–2.38 (t, 2H), 2.38–2.55 (m, 2H), 2.55–2.64 (m, 2H), 2.72–2.83 (m, 1H), 2.85–2.95 (m, 3H), 3.07–3.18 (q, 2H), 3.66–3.74 (q, 1H), 5.28 (broad s, 1H), 6.79–6.98 (m, 2H), 7.07–7.40 (m, 14H); IR (KBr) U 3403, 2939, 1769, 1509 cm$^{-1.}$

Example 59

7-[N-3-(4-Fluorophenyl)propionyl]-1-[N-(1,2,3,4-tetrahydro-1-methyl-6-bromo-7-methoxyisoguinolinyl)]-4,4-diphenylheptane hydrochloride

The procedure described in experiment 50 was used but substituting 1,2,3,4,-tetrahydro-1- methyl-6-bromo-7-methoxyisoquinoline for 1,2,3,4-tetrahydro-1-methyl-6-methoxyisoquinoline. After workup and purification with a silica gel column chromatography 7-[N-3-(4-fluorophenyl)-propionyl]-1-[N-(1,2,3,4-tetrahydro-1-methyl-6-bromo-7-methoxyisoquinolinyl)]-4,4-diphenyl- heptane was obtained: MS shows (M+H) @ 673; $^1$H-NMR (CDCl$_3$, δ): 1.06–1.28 (m, 7H). 0- 2.12 (m, 4H). 2.3–2.36 (t, 2H), 2.36–2.58 (m, 4H), 2.68–2.77 (m, I H), 2.82–2.92 (m, 3H), 3.07- 3.17 (q, 2H). 3.59–3.67 (q, 1H), 3.84 (s, 3H), 5.04 (broad s, 1H), 6.51 (s, 1H), 6.87–6.94 (t, 1H), 7.05–7.28 (m. 14H); IR (KBr) u 3419, 2936, 1643, 1509 cm$^{-1}$. The hydrochloride salt was prepared as in example 4 to give 7-[N-3-(4-fluorophenyl)propionyl]-1-[N-(1, 2,3,4-tetrahydro-1- methyl-6-bromo-7-methoxyisoquinolinyl)]-4,4-diphenylheptane hydrochloride: mp 104–108° C.; Anal. Calcd for C39H44N$_2$O$_2$BrF·HCl,1.25H$_2$O: C, 64.10; H, 6.55; N, 3.85; Found: C, 63.94; H, 6.55; N, 3.68.

Example 60

7-[N-3-(4-Fluorophenyl)propionyl]-1-[N-(1,2,3,4-tetrahydro-1-methyl-6-fluoro-7-methoxyisoguinofinyl)1–4.4-diphenylheptane hydrochloride

The procedure described in experiment 50 was used but substituting 1,2,3,4-tetrahydro-1- methyl-6-fluoro-7-methoxyisoquinoline for 1,2,3,4-tetrahydro-1-methyl-$^6$-methoxyisoquinoline. After workup and purification with a silica gel colurnn chromatography 7-[N-3-(4-fluorophenyl)-propionyl]-1-[N-(1,2,3,4-tetrahydro-1-methyl-6-fluoro-7-methoxyisoquinolinyl)]-4,4-diphenyl- heptane was obtained: MS shows (M+H)$^+$ @ 611; $^1$H-NMR (CDCl$_3$, δ): 1.08–1.30 (m, 7H), 2.02–2.18 (m, 4H), 2.32–2.40 (t, 2H), 2.40–2.62 (m, 4H), 2.68–2.78 (m, 1H), 2.85–2.95 (m, 3H), 3.10–3.18 (q, 2H), 3.62–3.70 (q, 2H), 3.84 (s, 3H), 5.25 (broad s, 1H), 6.54–6.61 (d, 1H), 6.72- 6.78 (d, 1H), 6.89–6.97 (t, 2H)) 7.08–7.31 (m, 12H); IR (MIC) v 3298, 2941, 1644, 1510 cm$^{-1}$. The hydrochloride salt was prepared as in example 4 to give 7-[N-3-(4-fluorophenyl)propionyl]-1-[N-(1,2,3,4-tetrahydro-1-methyl-6-fluoro-7-methoxyisoquinolinyl)]-4,4-diphenylheptane hydrochloride.

Example 61

7-[N-3-(4-Fluorophenyl)propionyl]-1-[N-(1,2,3,4-tetrahydro-1-methyl-6-methoxy-7-bromoisoguinolinyl)1–4.4-diphenylheptane hydrochloride

The procedure described in experiment 50 was used but substituting 1,2,3,4-tetrahydro-1- methyl-6-methoxy-7-bromoisoquinoline for 1,2,3 .4-tetrahydro-1-methyl-6-methoxyisoquinoline. After workup and purification with a silica gel column chromatography 7-[N-3-(4-fluorophenyl-propionyl)]amino-1-[N-( I .23,4-tetrahydro-1-methyl-6-methoxy-7-bromoisoquinolinyl)]-4,4- diphenylheptane was obtained: MS shows (M+H) , 673; $^1$H-NMR (CDCl$_3$, δ): 1.07–1.28 (m. 7H), 2.0–2.12 (m, 4H), . 30–2.52 (m, 4H), 2.60–2.77 (m, 3H), 2.83–2.94 (m, 3H), 3.07–3.16 (m. 2H). 3.65–3.70 (m, 1H). 3.86 (s, 3H). 5.18 (broad s. 1H), 6.70–6.75 (d, 1H), 6.88–6.96 (m. 3H). 7.06–7.28 (m, 12H); IR (MIC) u 3293. 2939, 1646. 1509 cm-i The hydrochloride salt was prepared as in example 4 to give 7-[)V-3-(4-fluorophenyl)propionyl]-1-[N-(1, 2,3,4-tetrahydro-I-methyl-$^6$-methoxy-7-bromoisoquinolinyl)]-4,4-diphenylheptane hydrochloride.

Example 62

7-[N-3-(4-Fluorophenyl)propionyl]-1-[N-(1,2,3,4-tetrahydro-1.6-dimethyl-7-methoxyisoquinolinyl) 1–4.4-diphenylhelptane hydrochloride

The procedure described in experiment 50 was used but substituting 1,2.3,4-tetrahydro- 1,6-dimethyl-7-methoxyisoquinoline for 1,2,3,4-tetrahydro-1-methyl-6-methoxyisoquinoline. After workup and purification with a silica gel colum chromatography 7-[N-3-(4-fluorophenyl)-propionyl]-1-[N-(1,2,3,4-tetrahydro- 1,6-dimethyl-7-methoxyisoquinolinyl)]-4,4-diphenylheptane was obtained: MS shows (M+H)$^+$ @ 607; $^1$H-NMR (CDCl$_3$, δ): 1.07–1.20

(m, 2H). 1.22–1.38 (m, 5H), 2.01–2.17 (m, 4H), 2.14 (s, 3H), 2.34–2.43 (t, 2H), 2.47–2.78 (m, 5H), 2.85–2.94 (t, 2H), 2.94–3.05 (m, 1H), 3.10–3.19 (q, 2H), 3.72–3.78 (m, 1H), 3.78 (s, 3H), 5.59 (broad s, 1H), 6.42 (s, 1H), 6.81 (s, 1H), 6.87–6.95 (t, 2H), 7.08–7.29 (m, 12H). The hydrochloride salt was prepared as in example 4 to give 7-[N-3-(4-fluorophenyl)propionyl]-1-[N-(1,2,3,4-tetrahydro- 1,6-dimethyl-7-methoxyisoquinolinyl)]-4,4-diphenylheptane hydrochloride.

Example 63

7-[N-3-(4-Fluorophenyl)propionyl]-1-[N-(1,2,3,4-tetrahydro-1-methyl-6-carbomethoxy-7-methoxyisoguinolinyl)1–4.4-diphenylhentane hydrochloride A solution 7-[N-3-(4-fluorophenyl)propionyl]-1-[N-(1,2,3,4-tetrahydro-1-methy 1-7-methoxy-6-bromoisoquinolinyl)]-4,4-diphenylheptane (0.10 g) in methanol (25 mL) was treated with [1, 1-bis(diphenylphosphino)ferrocene]dchloropalladium(II) complex with dichloromethane (0.025 g) and lutidine (0.032 g) heated at 120° C. under 180 psi pressure of carbon monoxide for 22 hr. The catalyst was filtered and the solution was concentrated in v acuo. The residue was purified by a silica gel column chromatography to give 7-[N-3-(4-fluorophenyl)propionyl]-1- [N-(1,2,3,4-tetrahydro-1-methyl-6-carbomethoxy-7-methoxy isoquinolinyl)]-4,4-diphenNl-heptane: MS shows (M+H)0 ® 651. The hydrochloride salt was prepared as in example 4 to give 7-[N-3-(4-fluorophenyl-propionyl)]amino-1-[N-(1,2,3. 4-tetrahydro-1-methyl-6-carbo- methoxy-7-methoxyisoquinolinyl)]-4,4-diphenylheptane hydrochloride: mp 92° C.: Anal. Calcd for $C_{41}H_{47}N_2O_4F,HCl2.5H_2O$: C, 67.18; H, 6.55; N, 3.82; Found: C, 67.15; H. 6.93: N. 3.62.

Example 64

7-[N-3-(4-Fluorophenyl)propionyl]amino-1-[N-(1,2,3,4-tetrahydro-1-cyclobutyl-6-bromo-7-methoxyisoquinolinyl)l-4,4-diiphenylheptane hydrochloride The procedure described in example 50 was used but substituting 1,2.3,4-tetrahydro- 1-cyclobutyl-6-bromo-7-methoxyisoquinoline for substituting 1,2,3,4-tetrahydro-1-methyl- 6-bromo-7-methoxyisoquinoline. After workup and purification with a silica gel column chromatography 7-[N-3-(4-fluorophenyl)propionyl]-1-[N-(1,2,3,4-tetrahydro-1-cyclobutyl- 6-bromo-7-methoxyisoquinolinyl)]-4,4-diphenylheptane was obtained: MS shows (M+H)⁺ @ 713; ¹H-NMR (CDCl₃, δ): 1.07–1.13 (m, 4H), 1.51–1.91 (m, 6H), 1.91–2.18 (m, 6H), 2.27–2.58 (m, 6H), 2.60–2.80 (m, 2H), 2.86–3.24 (m, 3H), 3.84 (s, 3H), 5.03 (broad s, 1H), 6.48 (s, 1H,), 6.89–6.97 (t, 2H), 7.08–7.30 (m, 13H); IR (MIC) u 3295, 2941, 1644, 1509 cm⁻¹. The hydrochloride salt was prepared as in example 4 to give 7-[N-3-(4-fluorophenyl)propionyl]-1- [N-(1,2,3,4-tetrahydro-1-cyclobutyl-6-bromo-7-methoxyisoquinolinyl)]-4,4-diphenylheptane hydrochloride.

Example 65

7-[N-3-(4-Fluorophenyl)propionyl]-1-[N-(1,2,3,4-tetrahydro- 1.3-dimethyl-6,7-dimethoxyisoguinolinyl)1–4.4-diphenylheptane hydrochloride The procedure described in example 50 was used but substituting 1,29.3,4-tetrahydro- 1,3- dimethyl-6,7-dimethoxyisoquinoline for 1,2,3,4-tetrahydro-1-methyl-6-methoxyisoquinoline. After workup and purification with a silica gel column chromatography 7-[N-3-(4-fluorophenyl)-propionyl]-1-[N-(1,2,3,4-tetrahydro- 1,3-dimethyl-6,7-dimethoxyisoquinolinyl)]-4,4-diphenyl- heptane was obtained: MS shows (M+H)⁺ @ 637; ¹H-NMR (CDCl₃, δ): 0.98–1.34 (m, 8H). 1.54–1.68 (m. 2H), 1.33–2.10 (m. 4H). 2.28–2.40 (m, 4H), 2.28–2.40 (t. 2H). 2.45–2.64 (m, 4H). 2.79–9.94 (q. 2H).3.60–3.77 (m, 1H).3.84 (s, 6H), 5.05 (broad s, 1H). 6.52 (s, 1H), 6.57 (s. 1H), 6.86–6.97 (t. 2H), 7.05–7.29 (m. 12H); IR (KBr) u 3414, 2933, 1646, 1509 cm⁻¹. The hydrochloride salt was prepared as in example 4 to give 7-[N-3-(4-fluorophenylpropionyl)]- amino-1-[N-(1.2. 3,4-tetrahydro- 1,3-dimethyl-6,7-dimethoxyisoquinolinyl)]-4,4-diphenylheptane hydrochloride: mp 97–108° C.

Example 66

7-[N-3-(4-Fluorophenyl)propionyl]-1-[N-(1,2,3,4-tetrahydro-3-mekyl-6,7-dimethoxyisoguinolinyl)]-4,4-diphenylheptane hydrochloride The procedure described in example 50 was used but substituting 1,2,3,4-tetrahydro-3- methyl-6,7-dimethoxyisoquinoline for 1,2,3,4-tetrahydro-1-methyl-6-methoxyisoquinoline. After workup and purification with a silica gel column chromatography 7-[N-3-(4-fluorophenyl)-propionyl]-1-[N-(1, 2,3,4-tetrahydro-3-methyl-6,7-dimethoxyisoquinolinyl)]-4,4-diphenylheptane was obtained: MS shows (M+H)⁺ @ 623; ¹H-NMR (CDCl₃, δ): 0.94–1.04 (d, 31H), 1.04–1.30 (m, 4H), 1.98–2.15 (m, 4H), 2.27–2.60 (m, 5H), 2.76–2.94 (m, 4H), 3.05–3.18 (q, 2H), 3.36–3.59 (m, 2H), 3.83 (s, 6H), 5.03 (broad s, 1H), 6.47 (s, 1H), 6.53 (s, 1H), 6.87–6.98 (m, 2H), 7.06–7.30 (m, 12H); IR (KBr) v 3384, 2934, 1646, 1510 cm⁻¹. The hydrochloride salt was prepared as in example 4 to give 7-[N-3-(4-fluorophenyl)propionyl] I -1[N-(1,2,3,4-tetrahydro-3-methyl-6,7- dimethoxyisoquinolinyl)]-4,4-diphenylheptane hydrochloride: mp 87–91° C.; Anal. Calcd for $C_{40}H_{47}N_2O_3F^1HCl^1H2O$: C, 70.93; H, 7.44; N, 4. 13; Found: C, 70.49; H, 7.28; N, 3.85.

Example 67

7-[N-3-(4-Fluorophenyl)propionyl]-1-[N-(1,2,3,4-tetrahydro- 1.1-dimethyl-6,7-dimethoxyisoguinolinyl)1–4.4-diphenylheptane hydrochloride The procedure described in example 50 was used but substituting 1,2,3,4-tetrahydro-1,1- dimethyl-6,7-dimethoxyisoquinolinyl for 1,2,3 .4-tetrahydro-1-methyl-6-methoxytetra- hydroisoquinoline. After workup and purification with a silica gel column chromatography 7-[N-3-(4-fluorophenyl)propionyl]-1-[N-(1,2,3 .4-tetrahydro- 1.1-dimethyl-6,7-dimethoxy- isoquinolinyl)]-4,4-diphenylheptane was obtained: MS shows (M+H)⁺ (a 637; ¹H-NMR (CDCl₃, δ): 1.08–1.23 (m, 4H). 1.37 (s. 6H). 2 01–2.12 (21) 9 ) .91 (m, 2H), 2.31–2.39 (t, 2H). 2.39–2.48 (broad m, 2H), 2.56–2.70 (m. 4H). 2.87–2.95 (t, 2H). 3.10–3.19 (q, 2H), 3.83 (s, 31H), 3.89 (s, 33H), 5.13 (broad s, 1H), 6.51 (s, 1H). 6.72 (s. 1H), 6.89–6.96 (t, 1H), 7.08–7.30 (m, 131H); IR (KBr) u 3388, 2932, 1646, 1510 cm⁻¹. The hydrochloride salt was prepared as in example 4 to give 7-[N-3-(4-fluorophenyl)propionyl]-1-[N-(1,2,3,4-tetrahydro- 1.–3-dimethyl-6,7- dimethoxyisoquinolinyl)]-4, 4-diphenylheptane hydrochloride: mp 104–107° C.; Anal. Calcd for $C_{41}H_{49}N_2O_3F,HC,11.25H_2O$: C, 70.77; H, 7.60; N, 4.20; Found: C, 70.76; H, 7.57; N, 3 84.

Example 68

7-[N-3-(4-Fluorophenyl)propionyl]-1- rN-(1,2,3,4-tetrahydro- 1.3-dimethyl-7-methoxyisoquinolinyl) 1–4.4-diphenylheiltane hydrochloride

The procedure described in example 50 was used but substituting 1,2.3,4-tetrahydro-1,3-di methyl-7-methoxyisoquinoline for 1,2,3,4-tetrahydro-1-methyl-6-methoxytetrahydro- isoquinoline. After workup and purification with a silica gel column chromatography 7-[N-3-(4-fluorophenyl)propionyl]-1-[N-(1,2,3,4-tetrahydro- 1,3-dimethyl-7-methoxy- isoquinolinyl)]-4,4-diphenylheptane was obtained: MS shows $(M+H)^+$ @ 607; IR (KBr) v 3273, 2934, 1616, 1509 $cm^{-1}$. The hydrochloride salt was prepared as in example 4 to give 7-[N-3-(4-fluorophenyl)propionyl] amino-1-[N-(1,2,3,4-tetrahydro- 1,3-dimethyl-7-methoxy-isoquinolinyl)]-4,4-diphenylheptane hydrochloride.

Example 69

7-[N-3-(4-Fluorophenyl)propionyl]-1-[N-(2,3,4,5-tetrahydro-1-methyl-7.8-dimethoxy-I H-2-benzazepinyl)1–4.4-diphenylheptane hydrochloride

The procedure described in example 50 was used but substituting 2,3,4.5-tetrahydro-1- methyl-7,8-dimethoxy- I H-2-benzazepine for 1,2,3,4-tetrahydro-1-methyl-6-methoxy- isoquinoline. After workup and purification with a silica gel column chromatography 7-[N-3-(4-fluorophenyl)propionyl]-1-[N-(2,3,4.5-tetrahydro-1-methyl-7,8-dimethoxy- 1H- 2-benzazepinyl)]-4,4-diphenylheptane was obtained: MS shows $(M+H)^+$ @ 637; $^1$H-NMR (CDCl$_3$, δ): 1.04–1.21 (m, 4H), 1.21–1.35 (broad m, 1H). 1.43–1.52 (d, 3H), 1.52–1.68 (m, 2H), 1.87–1.99 (m, 2H), 1.99–2.12 (m. 3H). 2.14–2.46 (m. 3H), 2.68–2.85 (broad m, 1H), 2.85–3.02 (m, 3H), 3.06–3.17 (t, 2H), 3.18–3.32 (broad m, 1H). 3.80 (s. 3H), 3.84 (s, 3H). 5.48 (broad s, 1H). 6.48 (broad s. I H), 6.62 (s. I H). 6.87–6.97 (t. 2H). 7.03–7.30 (m. 12H). The hydrochloride salt was prepared as in example 4 to give 7-[A-3-(4-fluorophenyl)propionyl]-1-[N-(2,3,4,5-tetra- hydro-1-methyl-7,8-dimethoxy- 1H-2-benzazepinyl)]-4,4-diphenylheptane hydrochloride.

Example 70

6-[N-3-(4-Fluorophenyl)propionylamino-1-[N-(1,2,3,4-tetrahydro-1-methyl-6,7-methoxyisoquinolinyl)]-3.3-diphenylhexane hydrochloride

Step 1: 4.4-Diphenyl-6-methoxyhex-5-enenitrile (Compound 16. Scheme 4)

To a solution of (methoxymethyl)triphenylphosphonium chloride (9.83 g, 28.7 mmol, 1I.1 eq.) in anhydrous THF (60 mL) cooled to 0–5° C. under nitrogen was added dropwise a solution of n-butyllithium (13.7 mL of 2M solution. in pentane). The reaction mixture was stirred at the same temperature for 1 hr. Then a solution of 4,4-diphenyl-4-formylbutyronitrile (Compound L Scheme 2) (6.5 g, 26.1 mmol) in THF (20 mL) was added via syringe and stirring was continued for 16 hr. The reaction mixture was concentrated in vacuo and the residue was purified by silica gel column chromatography (eluted with 3% to 10% ethyl acetate/hexane) to give the desired product as a yellow oil (4.2 g, 58 %): $^1$H-NMR (CDCl$_3$, δ): 2.06–2.17 (m, 2H), 2.81–2.86 [2.62–2.68] (m, 2H), 3.57 (s, 3H), 4.76 (d, J=7.3 Hz, 1H), 5.95 (d, J=7.3 Hz, 1H), 7.15–7.42 (m, 10H).

Step 2: 4.4-Diphenyl-5-formylpentanonitrile (Compound 17. Scheme 4)

To a solution of 4,4-diphenyl-6-methoxyhex-5-enenitrile (4.0 g, 14.4 mmol) in diethylether (60 mL) was added HCl (2 mL, 37 %). The reaction mixture was stirred at room temperature for 16 hr and then the solvent was evaporated in vacuo . The residue was dissolved in dichloro- methane and filtered through a plug of silica gel to give the desired aldehyde as an oil (3.78 g, 99%): $^1$H-NMR (CDCl$_3$, δ): 2.03–2.10 (m, 2H), 2.56- 2.64 (m, 2H), 3.12 (d, J=3 Hz, 2H), 7.14–7.41 (m, 1OH), 9.34 (t, J=3 Hz, 1H). Anal. Calcd for C$_1$8HI$_7$NO: C, 82.10; H, 6.51; N, 5.32. Found: C, 82.10; H. 7.02; N. 4.78.

Step 3: 6-Amino-3.3-diphenylhexan-1-ol (Compound 18. Scheme 4)

To a suspension of lithium aluminumhydride (0.57 g. 15 mmol) in anhydrous THF (20 mL) was added carefully dropwise a solution of 4,4-diphenyl-5-formylpentanonitrile (1.96 g. 7.4 mmol) in anhydrous THF (20 mL). The mixture was stirred at rt for 1.5 hr. The reaction mixture was quenched by careful addition of SN NaOH (2.5 mL) and followed by water (1.5 mL). The mixture was stirred at room temperature for 10 min and then filtered and the solid was washed twice with diethylether. The organic filtrates were combined, dried (Na$_2$SO$_4$) and concentrated to give the desired product as solid foam (1.60 g, 80%): MS showed $(M+H)^+$ ( 270; $^1$H-NMR (CDCl$_3$, δ): 1.17–1.34 (m, 2H), 2.12–2.22 (m, 2H), 2.31–2.43 (m, 2H), 2.62–2.74 (m, 2H), 3.30–3.40 (m, 2H), 7.11–7.34 (m, 1OH).

Step 4: 6-[N-3-(4-Fluorophenyl)propionyl]amino-3.3-diphenylhexan-1-ol (Compound 19. Scheme 4).

To an ice-cold and stirred solution of 6-amino-3,3-diphenylhexan-1-ol (0.54 g, 2 mmnol) in methylene chloride solution (10 mL) was added 3-(4-fluorophenyl)propionic acid (0.37 g, 2.2 mmol) followed by I -hydroxybenzotriazole hydrate (HOBt) (0.297 g, 2.2 mmol), triethylamine (0.31 mL), and 1-(3-dimethylaminopropyl)-3-ethylcarbodiimide (EDCI) (0.422 g, 2.2 mnmol). The reaction mixture was stirred at rt overnight and then diluted with methylene chloride (30 mnL) and the solution was washed first with water and then with brine. The organic phase was dried (Na$_2$SO$_4$) and concentrated in vacuo. The residue was purified by a silica gel column using (1:1) ethyl acetate/ hexane yielding the desired compound as amorphous solid (0.24 g): MS showed $(M+H)^+$ @ 420; $^1$H-NMR (CDCl$_3$, δ): 1.10–1.21 (m, 2H), 2.05–2.12 (m. 2H), 2.37 (dd, 4H, J=7, 14Hz), 2.90 (t, 2H, J=7.5 Hz), 3.14 (dd, 2H, J=7, 13 Hz), 3.41 (t, 2H, J=7 Hz), 5.29 (bs, 1H), 6.91–7.02 (m, 4H), 7.10–7.30 (m, 1OH).

Step, 5: 6-[N-3-(4-Fluorophenyl)propionyl]amino-3.3-diphenylhexyl mesylate (Compound 20. Scheme 4).

To a solution of 6-[N-3-(4-fluorophenyl)propionyl] amino-3,3-diphenylhexan-1-ol (0.20 g. 0.49 mmol) in methylene chloride (5 mL) was added at 0° C. methanesulfonyl chloride (0.046 mL) followed by triethylamine (0.074 mL). The solution was stirred at 0° C. for 30 min. The reaction mixture was washed with I N HCl, water and brine. The organic phase was dried and concentrated in vacuo to give the desired product as an oil (0.227 g, 93%): MS showed (M+H) @ 498; $^1$H-NMR (CDCl$_3$, δ): 1.12–1.22 (m. 2H), 2.06–2.13 (m, 2H), 2.42 (t, 2H, J=7.5 Hz), 2.56 (t, 2H. J=7.5 Hz), 2.87–2.96 (m, 5H), 3.16 (dd, 2H, J=7.3, 12.2 Hz), 3.94 (t, 2H, J=7 Hz). 5.39 (bs. 1H), 6.89–6.98 (m, 4H). 7.09–7.31 (m. 1OH). Anal. Calcd for C$_2$sH$_{32}$NO$_4$FS: C. 67.58; H. 6.48; N, 2.81; Found: C, 67.80; H, 6.64; N, 2.74. This was used in the next step without further purification.

Step 6: 6-[N-3-(4-Fluorophenyl)propionyl]amino 1-[N-(1,2,3,4-tetrahydro-1-methyl-6,7- dimethoxy-isoquinoline)1–3, 3-diphenylhexane hydrochloride (Compound III. Scheme 4) 6-[N-3-($^4$-Fluorophenyl)propionyl]amino I -l[N-(1,2,3,4-tetrahydro-1-methyl-6,7-dimethoxy- isoquinoline)]-3,3- diphenylhexane hydrochloride was prepared using the procedure described in example 4 but substituting 6-[N-3-(4-fluorophenyl)propionyl]amino-3,3-diphenylhexyl mesylate for 7-[N-3-(4-fluorophenyl)propionyl]amino-4,4-diphenylheptyl mesylate and 1,2,3,4-tetrahydro-1-methyl-6,7-dimethoxy-isoquinoline hydroiodide for 1-cyclopropyl-4,5-dimethoxy-1,2,3,4-tetrahydroisoquinoline hydroiodide. The obtained residue was purified by a silica Oel column chromatography (ethyl acetate to ethyl acetate/methanol (95:5)) to give the product as an amorphous solid: MS showed (M+H)[] @ 609; $^1$H-NMR (CDCl$_3$, δ): 1.11–1.28 (m, 5H), 2.00-2.11 (m, 2H), 2.22–2.28 (m, 1H), 2.35–2.62 (m, 6H), 2.68–3.02 (m, 5H), 3.06–3.24 (m, 2H), 3.81 (s, 3H), 3.82 (s, 3H), 3.88 (q, 1H, J=7 Hz), 5.95 (bt, 1H), 6.43 (1H, s), 6.49 (1H, s), 6.90–6.97 (2H, m), 7.10–7.29 (12H, m). This compound was treated with methanol/HCl, the solution was concentrated in vacuo and the residue was dissolved in (1:1) acetonitrile/water and lyophilized to give the hydrochloride salt: IR (MIC) u 3300, 2942, 1646 cm$^{-1}$; Anal. Calcd for C$_{39}$H$_{45}$N$_2$O$_3$F-HCl 0.5 H$_2$O: C, 71.59; H, 7.24; N, 4.28; Found: C, 71.35; H, 7.13; N. 4.01.

Example 71

8-[N-3-(4-Fluorophenyl)propionyl]amino-1-[N-(1,2,3,4-tetrahydro-1-methyl-6,7-dimethoxyisoquinolinyl)1–5.5-diphenyloctane hydrochloride Step 1: Methyl 7-cyano-5.5-diphenyl-hept-2-enoate (Compound 21. Scheme 5)

A mixture of 4,4-diphenyl-5-formylpentanonitrile (1.87 g, 7.1 mmol) and (carbomethoxymethylene)triphenyl phosphorane (2.85 g. 8.5 mmol) in toluene (50 mL) was heated under reflux for three days. The reaction mixture was concentrated in vacuo and the residue was purified by silica gel column chromatography to give the desired product as a colorless oil (1.56 g 69%): MS showed (M+H)$^+$ c 320; $^1$H-NMR (CDCl$_3$, δ): 1.97–2.0(m. 2H), 2.44–2.51 (m. 2H), 3.00 (dd, 2H, J=1.4, 7.4 Hz), 3.68 (s, 3H), 5.82 (dt, 1H, J=1.4. 15.6 Hz), 6.52 (dt, 1H. J=7.3, 15.6 Hz), 7.10–7.55 (m, 4H), 7.21–7.35 (m, 6H); Anal. Calcd for C,,H$_{21}$NO$_2$: C. 78.97; H. 6.63; N, 4.39; Found: C, 78.68; H, 6.85; N. 4.27.

Step 2: Methyl 7-cyano-5,5-diphenylheptanoate (Compound 22 Scheme 5)

To a solution of methyl 7-cyano-5,5-diphenyl-hept-2-enoate (1.4 1 g, 4.41 mmol) in MeOH (di00 mL) was added Pd/C (0.714 g). The reaction mixture was hydrogenated at 4 atm for 21 hr. 5 The catalyst was filtered and the filtrate was evaporated in vacuo. The oily residue (2 g) was purified by a silica gel column chromatography (eluting with 15:85 mixture of ethyl acetateihexane) to yield the desired product as a colorless oil (96 %): MS showed (M+H)$^+$ e 322;H-NMR (CDCl$_3$, δ): 1.25–1.36 (mn, 2H), 1.98–2.13 (m,. 4H), 2.26 (t, 2H, J =7.1 Hz). 2.49–2.58 (mn, 2H) 3 .65 (s, )H), 7.10–7.17 (mn, 4H), 7.21–7.36 (mn, 6H); IR (MIC) u 2951, 2247, 1735, 1444, 1196 cm$^{-1}$; Anal. Calcd for C$_2$1H$_{21}$N0$_2$: C, 78.47; H, 7.2 1; N, 4.3 6; Found: C, 78.58; H, 7.12; N, 4.14.

Step 3: 8-Amino-5,5-diphenylocta-1-ol (Compound 23. Scheme 5)

To a solution of methyl 7-cyano-5,5-diphenyl-heptanoate (1.26 g, 3.92 mmol) in anhydrous THF (7 mL) was added dropwise a solution of LAH (7.8 mmol) in anhydrous THF (7.8 mL). The mixture was stirred at rt for 2 hr. The reaction mixture was quenched by careful addition of N NAOH (2.5 mL). The mixture was stirred at rt for 10 min and then filtered. The solid was washed twice with diethylether. The organic filtrates were combined, d1:ed (Mm$_2$SO$_4$) and concentrated in vacuo to give the desired product as solid foam (1.09 g, 88 %): MS showed (M+; 2H-NMR (CDCl$^3$, (Dl 6)1.00–1.18 (n, 4H). 1.41–1.527 (m, 2H), 2.05–2.19 (H , 4H), 2.62 (t, J=7H, 2H), 3.52 (t, J =7 Hz, 2H), 7.10–7.36 (m. I0H); IR (MIC) u171 29 45 , 1597, 1495. 1079 cm$^{-1}$; Anal. Calcd for C$_{20}$H$_{27}$NO C0.5 H$_2$O: C. 78.28; H, 9.20; N, 4 .59; Found: C, 78.92: H, 8.89; N, 4.30.

Step 4: 8-[N-3-(4-Fluorolphenyl)Propionyl]amino-5,5-dil[]henyloctan-lI-ol (Compound 243 Scheme 5)

To an ice-cold and stirred solution of 8-amino-5,5-diphenylocta-1-ol (0.531.2 1.79 mmol) in 15ethylene chloride solution (5 mL) and DMF (0.5 mL) was added (-(4-fluorophenyl)propionic acd (0.452 g, 2.7 mmol) followed by 1-hydroxybenzotriazole hydrate (HOBt) (0.363 g), 2.7 mmol), triethylamine (0.27g, 2.7 mmol), and Il-(3J-dimethylaminopropyl)-3-ethylcarbo- diimide (EDCI) (0.518 ga 2.7 mmol). The reaction mixture was stirred a t room temperature ovenight and then concentrated in vacuo. The residue was dissolved in methanol (50 mL) and a solution of LiOH (I M, 8 mL) was added and stirred overnight. The volatiles were evaporated, the residue was diluted with water (10 mL) and extracted with ethyl acetate (3×15 mL). The combined organic layers were washed with water, 1 M HCl, water and brine, dried (M-SO$_4$) filtered and concentrated in vacuo. The residue was purified by a silica gel column chromatography (eluting with a gradient of 60 % to 100% ethyl acetate/hexane) yielding the desired compound as amorphous solid: MS showed (M+H)$^+$ @ 448; $^1$H-NMR (CDCl$_3$, δ): 0.96- 1.16 (m, 4H), 1.37–1.54 (m, 2H), 2.01–2.12 (m, 4H), 2.35 (t, J =7.2 Hz, 2H), 2.90 (t, J =7.8 Hz, 2H), 3.08–3.17 (m, 2H), 3.56 (t, J=7 Hz, 2H), 5.16 (bt, 1H), 6.88–6.97 (m, 2H), 7.10–7.36 (m, 12H); Anal. Calcd for C$_{29}$H$_{34}$[NO$_2$: C, 77.82; H, 7.66; N, 3.13; Found: C, 77.72; H, 7.76; N, 3.15.

Step 6: 8-[N-3-(4-Fluorophenyl)propionyl]amino-5,5-diphenyloctly mesylate (Compound 25. Scheme 5).

To a solution of 8-[N-3-(4-fluorophenyl)propionyl] amino-5,5-diphenyloctan-1-ol (0 181 g, 0.404 mmol) in methylene chloride (3 mL) was added at 0° C. methanesulfonyl chloride (0.034 mL) followed by triethylamine (0.085 mL). The solution was stirred at 0° C. for 30 min. The reaction mixture was washed with water, 1 N HCl, water and brine. The organic phase was dried (MgSO$_4$) and concentrated in vacuo to give the desired product as an oil (0.201 g, 95%): MS showed (M+H)$^+$ @ 526; $^1$H-NMR (300 MHz, CDCl$_3$, δ): 1.00–1.17 (m, 4H), 1.62–1.73 (mn, 2H), 2.01–2.11 (mn, 4H), 2.37 (t, J=7.2 Hz, 2H), 2.90 (t, J=7.8 Hz, 2H), 2.92 (s, 3H), 3.08- 3.18 (mn, 2H), 4.16 (t, J=7 Hz, 2H), 5.24 (bt, 1H), 6.89–6.96 (m, 2H), 7.10–7.29 (m, 12H). This was used in the next step without fuirther purification.

Step 7: 8-[N-3-(4-Fluorophenyl)propionyl]amino 1-[N-(1,2,3,4-tetrahydro-1-methyl-6,7-dimethoxyisoquinolinyl)]-5,5-diDhenyloctane (Compound IV. Scheme 5)

8-[N-3-(4-Fluorophenyl)propionyl] amino-1-[N-(1, 2.3 .4-tetrahydro-1-methyl-6,7-dimethoxy-isoquinolinyl)]-5,5-diphenyloctane was prepared using the procedure described in example 4 but substituting 8-[N-3-(4-fluorophenyl) propionyl]amino-5,5-diphenyloctyl mesylate for 7-[N-3-(4-fluorophenyl)propionyl]amino-4,4-diphenylheptyl mesylate and 1-methyl-6,7-dimethoxy-1,2,3,4-tetrahydroisoquinoline hydroiodide for 1-cyclopropyl-6,7-dimethoxy-1,2,3,4-tetrahydro-isoquinoline hydroiodide. The residue was purified by a silica gel column chromatography using a gradient of (95:5) of ethyl acetate/methanol to give the desired product as an amorphous solid: MS showed (M+H)- @ 637; $^1$H-NMR (CDCl$_3$, δ): 0.94–1.13 (m, SH), 1.27 (d, J =6.6 Hz, 3H), 1.46–1.55 (m, 2H), 1.99–2.10 (m, 4H), 2.32 (t, J=7.5

Hz, 2H), 2.42- 2.60 (m, 3H), 2.67–2.80 (m, 2H), 2.88 (t, J=8 Hz, 2H), 2.94–3.00 (m, 1H), 3.10 (q, J=6.8 Hz, 2H), 3.73 (q, 1H, J=6.6 Hz), 3.82 (s, 6H), 5.08 (bt, 1H), 6.51 (1H, s), 6.54 (1H, s), 6.88–6.95 (2H, m), 7.08–7.24 (12H, m); IR (MIC) u 3306, 2935, 1653, 1510, 1224 $cm^{-1}$. This compound was treated with methanol/HCl, the solution was concentrated in vacuo and the residue was dissolved in (1:1) acetonitrilelwater and lyophilized to give 8-[N-3-(4-fluorophenyl) propionyl] amino-1- [N-(1,2,3,4-tetrahydro-1-methyl-6,7-dimethoxy-isoquinolinyl)]-5,5-diphenyloctane hydrochloride: Anal. Calcd for $C_{41}H_{49}N_2O_3F,HCl$ 1.5 $H_2O$: C, 70.31; H, 7.62; N, 4.00; Found: C, 70.11; H, 7.57; N, 4.22.

Example 72

8-[N-(4-Fluorophenylacetyl)]amino-1-[N-(1,2,3,4-tetrahydro-1-methyl-6,7-dimethoxyisoguinolinal) 1–5,5-diphenyloctane hydrochloride Step 1: 8-(4-Fluorophenylacetyl)amino-5,5-diphenyloctan-1-ol To an ice-cold and stirred solution of 8-amino-5,5-diphenylocta-1-ol (Compound 23, Scheme 5) (0.437 g, 1.47 mmol) in methylene chloride solution (5 mL) and DMF (0.5 mL) was added 4-fluoro-phenylacetic acid (0.34 g, 2.2 mmol) followed by 1-hydroxybenzotriazole hydrate (HOBt) (0.30 g, 2.2 mmol), triethylamine (0.22 g, 2.2 mmol), and 1-(3-dimethylamino- propyl)-3-ethylcarbodiimide (EDCI) (0.422 g, 2.2 mnmol). The reaction mixture was stirred at room temperature overnight and then concentrated. The residue was dissolved in methanol (50 mL) and a solution of LiOH (1 M, 8mL) was added and stirred overnight. The volatiles were evaporated, the residue was treated with water (10 mL) and extracted with ethyl acetate (3×15 mL). The combined organic layers were washed with water, 1 M HC1, water and brine, dried ($MgSO_4$) filtered and concentrated in vacuo. The residue was purified by a silica gel column chromatography (using a gradient of 60 % to 100% of ethyl acetate in hexane) yielding the desired product as amorphous solid: MS showed $(M+H)^+$ @ 434; $^1$H-NMR ($CDCl_3$, δ): 0.91–1.17 (m. 4H), 1.39–1.51 (m, 2H), 1.95–2.12 (m. 4H). 3 04–3 16 (m, 2H). 3.45 (s. 2H), 3.52 (t. J=7 Hz. 2H), 5.50 (bt, I H), 6.95- 7. 36 (m, 14H); Anal. Calcd for $C_{28}H_{32}[NO_2$: C. 77.57; H, 7.44; N, 3 .23; Found: C, 77.34; H, 7.55; N, 3.18.

Step 2: 8-(4-Fluorophenylacetyl)amino-5.5-diDhenylhexyl mesylate

To a solution of 8- (4-fluorophenyl)propionylamino-5,5-diphenyloctan-1-ol (0.189 g, 0.436 mmol) in methylene chloride (3 mL) was added at 0° C. methanesulfonyl chloride (0.037 mL) followed by triethylamine (0.091 mL). The solution was stirred at 0° C. for 30 min. The reaction mixture was washed with water, 1 N HCl, water and brine. The organic phase was dried ($MgSO_4$) and concentrated in vacuo to give the desired product as an oil (0.198 g, 89 %). This was used in the next step without further purification: MS showed $(M+H)^+$ @ 512; $^1$H-NMR ($CDCl_3$, δ): 1.00–1.14 (m, 4H), 1.63–1.71 (m, 2H), 1.97–2.09 (m, 4H), 2.93 (s, 3H), 3.11–3.20 (m, 2H), 3.48 (s, 2H), 4.15 (t, J=7 Hz, 2H), 5.30 (bt, 1H), 6.98–7.28 (m, 14H).

Step 3: 8-[N-(4-Fluorophenylacetyl)lamino-1-[N-(1,2,3,4-tetrahydro-1-methyl-6,7-dimethoxy- isoquinoline)]-5.5-diphenyloctane 8-[N-(4-Fluorophenylacetyl)]amino-1-[N-(1,2,3,4-tetrahydro-1-methyl-6,7-dimethoxy- isoquinoline)]-5,5-diphenyloctane was prepared using the procedure described in example 4 but substituting 8-(4-fluorophenylacetyl) amino-5,5-diphenylhexyl mesylate for 7-[N-3-(4-fluorophenyl)propionyl]amino-4,4-diphenylheptyl mesylate and 1-methyl-6,7-dimethoxy- 1,2,3,4- tetrahydroisoquinoline hydroiodide for 1-cyclopropyl-4,5-dimethoxy-1,2,3,4-tetrahydroiso- quinoline hydroiodide. The residue was purified by a silica gel column chromatog-raphy (using a gradient of 100% to 95% of ethyl acetate/methanol) to give the desired product as an amorphous solid: MS showed $(M+H)^+$ @ 623; $^1$H-NMR ($CDCl_3$, δ): 0.94–1.01 (m, 2H), 1.07- 1.17 (m, 2H), 1.30 (d, J=6.7 Hz, 3H), 1.45–1.56 (m, 2H), 1.96–2.09 (m, 4H), 2.43–2.62 (m, 3H), 2.69–2.86 (m, 2H), 2.97–3.05 (m, 1H), 3.13 (q, J=6.1 Hz, 2H), 3.45 (s, 2H), 3.77 (q, 1H, J=6.5 Hz), 3.83 (s, 6H), 5.25 (bt, 1H), 6.51 (1H, s), 6.54 (s, 1H), 6.97–7.04 (2H, m), 7.07- 7.25 (12H, m). ; IR (MIC) u 3301, 2934, 1648, 1509, 1225, 1033 $cm^1$. This compound was dissolved in methanol1HCl, the solution was concentrated in vacuo and the residue was dissolved in (1:1) acetonitrile/water and lyophilized to give 8-[N-(4-fluorophenylacetyl)]amino-1-[N-(1,2,3,4- tetrahydro-1-methyl-6,7-dimethoxyisoquinolinyl)]-5,5-diphenyloctane hydrochloride: Anal. Calcd for $C_{40}H_{47}N_2O3F\cdot HCl$ 0.75 $H_2O$: C, 71.40; H, 7.41; N, 4.16;.Found: C, 71 .37; H, 7.3 1; N, 4.06.

Example 73

7-[N-3-(4-Fluorophenyl)propionyl]amino-1-[N-(1,2, 3,4-tetrahydro-1-methyl-7-methoxy-3-methoxycarbonylisoquinolinyl)-4,4-diphenylheptane hydrochloride Step 1: 3.4-Dihydro-7-methoxy-3-methoxycarbonyl-1-methyl-isoquinoline To a solution of N-acetyl-O-methyltyrosine methyl ester (10 g, 39.8 mmol) in anhydrous dichloromethane (350 mL) was added oxalyl chloride (44 mL, 2 M solution). The reaction mixture was stirred for 1 hr and then cooled to - 10° C. and to it anhydrous iron (III) trichloride (7.75 g, 47.8 mmol) was added portionwise. The stirring was continued overnight at room temperature and then the reaction mixture was treated with 2 M HC1 (100 mL) for 2 hrs. The organic phase was separated, washed with water and brine, dried ($MgSO_4$) and concentrated in vacuo. Methanol (130 mnL) and concentrated sulfuric acid (6 niL) were added to the foamy residue and reaction was heated to reflux for 8 hrs. The reaction mixture was concentrated in vacuo, diluted with water (100 mL) and extracted with ethyl acetate (2×50 mL). The water layer was basified with ammonium hydroxide to pH >9 and extracted with dichloromethane (3×50 mL). The organic phase was washed with water, brine, dried ($MgSO_4$) and concentrated in vacuo. The dark yellow product (8.7 g) was purified by a silica gel column chromatography eluting with (1: 1) ethyl acetate/ hexane to yield 5.61 g (60 %) of yellow product: $^1$H-NMR ($CDCl_3$, δ): 2.45 (d, J=2 Hz, 3H), 2.82- 3.00 (m. 2H), 3.82 (s, 3H), 3.83 (s, 3H), 4.19 (qq. J=2. 6.8 Hz, I H), 6.93 (dd, J=2.7, 7.5 Hz, 1H), 7.05 (d, J=2.7 Hz, 1H), 7.14 (d, J=7.5 Hz- 1H): MS showed (M+H) +@ 234; Anal. Calcd for $C_{13}H_{15}NO_3$: C, 66.94; H, 6.48; N, 6.00; Found: C, 66.78; H, 6.36; N, 5.96.

Step 2: 1,2,3,4-Tetrahydro-7-methoxy-3-methoxycarbonyl-1-methyl-isoquinoline

To a solution of 3,4-dihydro-7-methoxy-3-methoxycarbonyl-1-methyl-isoquinoline (2.0 g. 8.57 mmol). obtained from the previous step, in veOH (I 50 mL) was added Pd/C (0.g). The reaction mixture was hydrogenated for 21 hr at 4 atm hydrogen pressure. The catalyst was filtered off and the filtrate was concentrated in vacuo. The oily residue (2 g) was purified by a silica gel column using (1: 1) ethyl acetate/ hexane to yield a yellowish oil (94 %): IR (MIC) U 3340, 2951, 1739, 1616, 1503, 1436, 1290, 1228, 1035 cm$^{-1}$; $^1$H-NMR (CDCl$_3$, δ): 1.51 (d.J=6.6 Hz, 3H). 2.75 (broad s, 1H), 2.89- 3.03 (m. 2H), 3.72 (dd, J=4.5, 11.1 Hz, 1H). 3.79 (s. 6H), 4.14 (q. J=6.6 Hz, 1H), 6.71- 6.75 (m, 2H), 7.02 (d, J=7.8 Hz, I H): MS showed (M+H) +@ 236; Anal. Calcd for C$_{13}$Hl$_7$NO$_3$ . HCl: C, 57.46; H, 6.68; N, 5.15; Found: C, 57.42; H, 6.64; N, 5.02.

Step 3: 1,2,3,4-Tetrahydro-7-methoxy-3-methoxycarbonyl-1-methyl-isoquinoline hydroiodide To a solution of 1,2,3,4-tetrahydro-7-methoxy-3-methoxycarbonyl-1-methyl-isoquinoline (0.526 g, 2.24 mmol) in methanol (10 mL) cooled to 0° C. was added dropwise a solution of 57% HI solution (0.33 mL). The ice bath was removed and the solution was stirred at rt for 20 min. To the bright orange solution was added ether (100 mL) and the mixture was stirred for 10 min. The light yellow precipitate was filtered and dried in vacuo (P$_2$O$_5$) to give the desired salt (0.736 g).

Step 4: 7-[N-3-(4-Fluorophenyl)provionyl]amino-1-[N-(1,2, 3,4-tetrahydro-1-methyl-7-methoxy-3-methoxycarbonolisoquinolinyl)-4,4-diphenylheptane hydrochloride 7-[N-3-(4-Fluorophenyl)propionyl]amino-1-[N-(1,2,3,4-tetrahydro-1-methyl-7-methoxy-3-methoxycarbonylisoquinolinyl)]-4,4-diphenylheptane hydrochloride was prepared in a manner analogous to Example 4 but substituting 7-methoxy-3-methoxycarbonyl-1-methyl-1,2,3,4-tetrahydroisoquinoline for 1-cyclopropyl-6,7-dimethoxy-1,2,3,4-tetrahydroisoquinoline hydroiodide. The residue was purified by a silica gel column chromatography (eluting with a gradient of 100% to 95% of ethyl acetate/methanol) yielding an amorphous solid. MS showed (M+H)i: @ 651; IR (MIC) u 3303,2948, 1734, 1647, 1509, 1222, 1034 cm$^{-1}$; $^1$H-NMR (CDCl$_3$, δ): 1.02- 1.20 (m, 4H), 1.23 (d, J=6.8 Hz, 3H), 1.99- 2.06 (m, 4H), 2.35 (t, J=7.2 Hz, 2H), 2.57- 2.68 (m, 2H), 2.81 (dd, J=15.8, 4.8 Hz, 1H), 2.89 (t, J=7.8 Hz, 2H), 3.01 (dd, J=15.8, 8.4 Hz, 1H), 3.12 (q, J=6.1 Hz, 2H), 3.39- 3.45 (m, 1H), 3.63 (s, 3H), 3.70- 3.75 (m; 1H), 3.76 (s, 3H), 5.20 (bt, 1H), 6.57 (d, J=2.4 Hz, 1H), 6.70 (dd, J=2.4, 8.4 Hz,1H), 6.86- 6.95 (m, 2H). 7.00 (d, J=8.4, 1H), 7.07- 7.25 (12H, m). This compound was dissolved in methanol/HCl, the solution was concentrated in vacuo and the residue was dissolved in (1:1) acetonitrile/water and Iyophilized to give 7-[N-3-(4-fluorophenyl) propionyl]amino-1-[N-(1,2,3,4-tetrahydro-1- methyl1-7-methoxy-3-methoxycarbonylisoquinolinyl)]-4,4-diphenylheptane hydrochloride: Anal. Calcd for C$_4$1H$_{47}$N$_2$O$_4$F-HCl 0.5 H$_2$O: C, 70.72; H, 7.09; N, 4.02; Found: C, 70.84; H, 7.19; N, 3.87.

Example 74

7-[N-3-(4-Fluorophenyl)propionyl]amino-1-[N-(1,2, 3,4-tetrahydro-3-(2-hydroxyethylaminocarbonyl)-1-methyl-7-methoxyisoguinolinyl)]-4,4-diphenylheptane hydrochloride 7-[N-3-(4-Fluorophenyl)propionyl] amino-1-[N-(1,2,3,4-tetrahydro-1-methyl-7-methoxy-3-methoxycarbonylisoquinoline)]-4,4-diphenylheptane (72 mg) was dissolved in DMF (0.5 mL) and ethanolamine (1 mL) and the solution was stirred for 3 days at room temperature. The reaction mixture was concentrated in vacuo to give an oily residue which was purified by a silica gel column chromatography (eluting with a gradient of 100% to 95% of dichloromethane/ methanol). MS showed (M+H)$^+$ @ 680; IR (MIC) U 3304,2938, 1651, 1510, 1222, 1032cmrl; $^1$H-NMR (CDCl$_3$, δ): 0.95- 1.30 (m, 7H), 1.92- 2.09 (m, 4H), 2.34–2.53 (m, 4H), 2.76–3.70 (m, 12H), 3.77 (s, 3H), 5.23 (broad 1H), 5.48 (broad t, 1H), 6.57- 6.60 (m, 1H), 6.69–6.74 (m, 1H), 6.86–6.95 (m, 2H), 7.07–7.25 (m, 13H). This compound was dissolved in methanol/HCl, the solution was concentrated in vacuo and the residue was dissolved in (1 :1) acetonitrile/water and lyophilized to give 7-[N-3-(4-fluorophenyl)propionyl]amino-1-[N-(1,2,3,4-tetrahydro-3-(2- hydroxyethylaminocarbonyl)-1-methyl-7-methoxyisoquinolinyl)]-4,4-diphenylheptane hydrochloride; Anal. Calcd for C$_{42}$H$_5$oN$_3$O$_4$F-HCl: C, 70.42; H, 7.18; N, 5.87; Found: C, 69.96; H,7.35;N,5.71.

Example 75

7-[N-3-(4-Fluorophenyl)propionyl]amino-1-[N-(1,2, 3,4-tetrahydro-(3-hydroxypropylaminocarbonyl)-1-methyl-7-methoxyisoquinoline)l-4,4-diphenylheptane hydrochloride The procedure described in example 74 was used but substituting 3-amino-1-propanol for ethanolamine. The obtained residue was purified by a silica gel column chromatography (using a gradient of 100% to 95% dichloromethane/methanol) to yield the desired product as an amorphous solid: MS showed (M+H)$^+$ @ 694; IR (MIC) u 3296, 2943, 1669, 1510.1201 cm-I: $^1$H-NMR (CDCl$_3$, δ): 0.95–1.37 (m, 7H), 1.50–1.76 (m, 2H), 1.90–2.08 (m, 4H), 2.34–2.59 (m. 4H), 2.80–3.56 (m. 12H), 3.77 (s, 3H), 5.36 (bs, 2H), 6.58–6.75 (m, 2H), 6.84–6.93 (m. 2H), 7.07- 7.25 (m, 13H). This compound was dissolved in methanol/HCl, the solution was concentrated in vacuo and the residue was dissolved in (1: 1) acetonitrile/water and lyophilized to give 7-[N-3-(4-fluorophenyl)propionyl]amino-1-[N-(1,2,3,4-tetrahydro-3-(3-hydroxypropyl- aminocarbonyl)-1-methyl-7-methoxyisoquinoline)]-4,4-diphenylheptane hydrochloride: Anal. Calcd for C$_{43}$H$_{52}$N$_3$O$_4$F-HCl: C, 70.71; H, 7.31; N, 5.75; Found: C, 70.40; H, 7.38; N, 5.60.

Example 76

7-[N-3-(4-Fluorophenyl)propionyl]amino-1-[N-(1,2, 3,4-tetrahydro-3-(4-hydroxybutylaminocarbonyl)-1-methyl-7-methoxyisoquinolinyl)]-4,4-diphenylheptane hydrochloride The procedure described in example 74 was used but substituting 4-amino-1-butanol for ethanolamine. The crude residue was purified by a silica gel column chromatography (eluting with a gradient of 100% to 95% of dichloromethane/methanol) to yield the desired product as an amorphous solid: MS showed (M+H)$^+$ (708; IR (MIC)× 3294, 2938, 1653, 1510, 1221 cm$^{-1}$; $^1$H-NMR (CDCl$_3$, δ): 0.98–1.50 (m, 1 1H), 1.92–2.06 (m, 4H), 2.34–2.53 (m, 4H), 2.80–3.62 (m, 12H), 3.78 (s, 3H), 4.22 (t, J=8.8 Hz, 1H), 5.39 (broad t, 1H), 5.51 (broad t, 1H), 6.61–6.73 (m, 2H), 6.87–6.95 (m, 2H), 7.02–7.29 (m, 13H). This compound was dissolved in methanol/HCl, the solution was concentrated in vacuo and the residue was dissolved in (1:1) acetonitrile/water and lyophilized to give 7-[N-3-(4-fluorophenyl) propionyl]amino-1-[N-(1,2,3,4-tetrahydro- 3-(4-hydroxybutylaminocarbonyl)-1-methyl-7-methoxyisoquinolinyl)]-4,4-diphenylheptane hydrochloride; Anal. Calcd for C$_{44}$H$_{54}$N$_3$O$_4$F-HCl H$_2$O: C, 70.14; H, 7.49; N, 5.61; Found: C, 69.97; H, 7.51; N, 5.37.

Example 77

7-[N-3-(4-Fluorophenyl)propionyl]amino-1- .V-(1,2, 3,4-tetrahydro-1-methyl-7-methoxy-3-(2-(N-pvrrolidinyl)ethylaminocarbonyl)isoquinolinyl)l-4,4-diphenylheptane hydrochloride The procedure described in example 75 was used but substituting )V-(2-hydroxyethyl)- pyrrolidine for ethanolamine. The residue was purified by a silica gel column chromatography (using a gradient of 100% to 95% of dichloromethane/methanol) to yield the product as an amorphous solid: MS showed (M+H)⁺ @ 733; ¹H-NMR (CDCl₃, δ): 0.79–1.12 (m, 4H), 1.36 (d, J=6.8 Hz, 3H), 1.75–2.17 (m, 8H), 2.38–2.58 (m, 9H), 2.84–2.95 (m, 5H), 3.08–3.19 (m, 4H), 3.24–3.30 (m, 1H), 3.47 (q, J=6.8 Hz, 1H), 3.77 (s, 3H), 5.77 (bt, 1H), 6.64 (d, J=3.4 Hz, 1H), 6.70 (dd, J=3.4, 8.1 Hz, 1H), 6.86–6.95 (m, 2H), 7.03 (d, J=8.1 Hz, 1H), 7.07- 7.26 (m, 12H). This compound was dissolved in methanol/HCl, the solution was concentrated in vacuo and the residue was dissolved in (1:1) acetonitrile/water and lyophilized to give 7-[N-3-(4-fluorophenyl)- propionyl]amino-1-[N-(1,2,3,4-tetrahydro-1-methyl-7-methoxy-3-(2-(N-pyrrolidinyl)-ethyl- aminocarbonyl)isoquinolinyl)]-4,4-diphenylheptane hydrochloride.

Example 78

7-[N-3-(4-Fluorophenyl)propionyl]amino-1-[N-(1,2,3,4-tetrahydro-1-methyl-3-hydroxymethyl-7-methoxyisoquinolinyl)]-4,4-diphenylheptane hydrochloride Step 1: 1,2,3,4-Tetrahydro-1-methyl-3-hydroxymethyl-7-methoxyisoquinoline To a solution of 1,2,3,4-tetrahydro-1-methyl-3-methoxycarbonyl-7-methoxyisoquinoline (0.67 g, 2.87 mmol) (described in example 73) in anhydrous tetrahydrofuran (5 mnL) was added dropwise I M solution of lithium aluminium hydride (5.7 nunol) in anhydrous tetrahydrofuran (5.7 mL). The mixture was stirred at rt for 3 hr. The reaction mixture was quenched by a careful addition of 5N NaOH (2 mL). The mixture was stirred at room temperature for 10 min and then filtered and the solid was washed twice with diethylether. The organic filtrates were combined, dried (MgSO₄) and concentrated in vacuo to give the desired product as solid foam (0.486 g, 82%): ¹H-NMR (CDCl₃, δ) 1.48 (d,J=6.3¹Hz, 3H), 2.46–2.67 (m, 2H), 3.04–3.12 (m, 1H), 3.72 (dd, J=8.4, 11.1 Hz, 1H), 3.72–3.81 (m, 1H), 3.79 (s, 3H), 4.08 (q. J=6.3 Hz, 1H), 6.71–6.75 (m, 2H), 7.02 (d, J =7.8 Hz, 1H): MS showed (M+H) +@ 208.

Step 2: 1,2,3,4-Tetrahydro-1-methyl-3-hydroxymethyl-7-methoxyisoguinoline hydroiodide To a solution of 1,2,3,4-tetrahydro-1-methyl-3-hydroxymethyl-7-methoxyisoquinoline (0.486 g, 2.3 mmol) in methanol (10 mL) cooled to 0° C. was added dropwise a solution of 57% HI solution (0.34 mL). The ice bath was removed and the solution was stirred at rt for 20 min. To the bright orange solution was added ether (100 mL) and the mixture was stirred for 10 min. The liaht yellow precipitate was filtered and dried in vacuo (P₂O₅) to give the desired salt.

Step3: 7-[N-3-(4-Fluorophenyl)propionyl]amino-1-[N-(1,2,3,4-tetrahydro-1-methyl-3-hydroxymethyl-7-methoxyisoquinoline)]-4,4-diphenylheptane 7-[N-3-(4-Fluorophenyl)propionyl]amino-1-[N-(1,2,3,4-tetrahydro-1-methyl-3-hydroxy- methyl-7-methoxyisoquinoline)]-4,4-diphenylheptane was prepared using the procedure described in example 4 but substituting 1,2,3,4-tetrahydro-1-methyl-3-hydroxymethyl-7- methoxyisoquinoline hydroiodide, from previous step, for 1,2,3,4-tetrahydro-1-cyclopropyl- 4,5-dimethoxyisoquinoline hydroiodide. The residue was purified by a silica gel columnn chromatography (eluting with a gradient of 100% to 95% of ethyl acetate/methanol) to yield an amorphous solid: MS showed (M+H)⁺ (623; IR (MIC) v 3290, 2929, 1647, 1510, 1222, 1032 cm⁻¹; ¹H-NMR (CDCl₃, δ): 0.83–1.18 (m, 4H), 1.41 (broad d, 3H), 2.01–2.11 (m, 4H), 2.43 (t, J=7.5 Hz, 2H), 2.57–2.78 (m, 3H), 2.92 (t, J=7.2 Hz, 2H), 3.01 (dd, J=15.8, 8.4 Hz, 1H), 3.13- 3.20 (m, 2H), 3.44–3.72 (m, 2H), 3.77 (s, 3H), 5.75 (bs, 1H), 6.58 (d, J=2.4 Hz, 1H), 6.70 (dd, J 2.4, 8.4 Hz, I H), 6.88–6.97 (m, 2H), 7.04 (d, J=8.4. 1 H), 7.08–7.28 (12H, m). This compound was dissolved in methanol/HCl, the solution was concentrated in vacuo and the residue was dissolved in (1:1) acetonitrile/water and lyophilized to give 7-[N-3-(4-fluorophenyl)propionyl]-amino-1-[N-(1,2,3,4-tetrahydro-1-methyl-3-hydroxymethyl-7-methoxyisoquinolinyl)]-4,4-diphenylheptane hydrochloride.

Example 79

The procedure described in example 1 was used wherein the appropriate acids were substituted for 3-(4-fluorophenyl) propionic acid. After workup and chromatographic purification the following compounds were obtained:

(79a) 7-[N-3-(phenyl)propionyl1amino-1-N-(1,2,3,4-tetrahydro-1-methyl-6,7-dimethoxyisoguinolinyl)]-4,4-diphenylheptane hydrochloride: MS showed (NI H)⁺ @ 605. (79b) 7-[N-3-(3,4-dichlorophenyl)propionyl]amino-1-[N-(1,2,3,4-tetrahydro-1-methyl-6,7-dimethoxyisoquinolinyl)]-4,4-dilphenylheptane hydrochloride: MS showed (M+H)⁺ @ 675. (79c) 7-[N-3-(3,4-difluoronhenyl)propionyl]amino-1-[N-(1,2,3,4-tetrahydro-1-methyl-6,7-dimethoxyisoquinolinyl)]-4,4-diohenylheptane hydrochloride: MS showed (M+H)⁺ @ 641; mp 96–99° C.; Anal. Calcd for C₄₀H₄₆N₂O₃F₂-HCL1.25H₂O: C. 68.65; H. 7.12; N; 4.00; Found: C, 68.45; H, 7.12: N, 3.99. (79d) 7-r.V-3-(3-fluoro-4-chloro-Dhenyl)propion-l1amino-1-[N-( I .2.3.4-tetrahydro-1-methyl-6,7-dimethoxyisoguinolinyl)1–4.4-diphenylheptane hydrochloride: MS showed (M+H)⁺ @ 658; mp 99–103° C.; Anal. Calcd for C₄₀H₄₆N₂O₃ClF¹HCl 1.25H₂O: C, 66.65; H, 6.99; N, 3.88; Found: C, 66.96; H, 6.99; N, 3.93. (79e) 7-[N-3-(4-fluoro-3-chloro-Iphenyl) propionyl]amino-1-[N-(1.2.3 .4-tetrahydro-1-methyl-6,7-dimethoxyisoquinolinyl)]-4,4-diphenylheptane hydrochloride: MS showed (M+H)⁺ (658. (79f) 7-[N-3-(3 .4-dimethoxylphenyl)propionyl]amino-1-[N-(1,2,3,4-tetrahydro-1-methyl- 6,7-dimethoxyisoquinolinyl)1–4,4-diphenylheptane hydrochloride: MS showed (M+H)⁺ @ 681. (79g,) 7-[N-3-(4-methoxyphenyl)propionyl]amino-1-[N-(1,2,3,4-tetrahydro-1-methyl-6,7-dimethoxyisoquinolinyl)]-4,4-diphenylheptane hydrochloride: MS showed (M+H)⁺ @ 651. (79h) 7-[N-3-(4-chlorophenol)propionyl]amino-1-[N-( I .2.3,4-tetrahydro-1-methyl-6,7-dimethoxyisoguinolinyl)1–4,4-diphenylheptane hydrochloride: MS showed (M+H)⁺ @ 640. (79i) 7-[N-3-(4-fluorophenyl)acetyl]amino-1-[N-(1.2.3 .4-tetrahydro-1-methyl-6,7-dimethoxyisoquinolinyl)]-4,4-diphenylhentane hydrochloride: MS showed (M+H)⁺ @ 609.

Example 80

7-[N-3-(4-Fluorophenyl)propionyl]amino-1-[NT(1,2,3,4-tetrahydro-1-(3-N-phthalimidopropyv)-6,7-dimethoxyisoquinolinyl)1–4.4-diphenylheptane hydrochloride The procedure described in example 22 was used substituting in the first step 4-N-phthalimidobutyric acid for N-phthalimidoglycine. After work up and chromatographic purification 7-[.v-3-(4-fluorophenyl)propionyl]amino-1-[N-(1 ,2,3,4-tetrahydro-1-(3-N-phthalimidopropyl)-6,7-dimethoxyisoquinolinyl)]-4,4-diphenylheptane was obtained: MS showed (M+H) @ 797. The hydrochloride salt was prepared as in example 4 to give 7-[N-3-(4- fluorophenyl)propionyl]amino-1-[N-(1,2,3,4-tetrahydro-1-(3-N-phthalimidopropyl)-6,7-dimethoxyisoquinolinyl)]-4,4-diphenylheptane hydrochloride.

Example 81

7-[N-3-(4-Fluorophenyl)Propionyl]amino-1-[N-(1,2,3,4-tetrahydro-1-(3-aminoproYIyl)-6,7-dimethoxyisoquinolinyl)1–4–4-diphenylheptane hydrochloride The procedure described in example 22 was used but substituting 4-N-phthalimidobutyric acid for N-phthalimidoglycine in step 1. After work up and chromatography 7-[N-3-(4-fluoro-phenyl)propionyl]amino-1-[N-( I,2,3,4-tetrahydro-1-(3-aminopropyl)-6,7-dimethoxyisoquinolinyl)]-4,4-diphenylheptane was obtained: MS showed $(M+H)^+$ @ 666. The hydrochloride salt was prepared as in example 4 to give 7-[N-3-(4-fluorophenyl)propionyl]- amino-1-[N-(1,2,3,4-tetrahydro-1-(3-aminopropyl)-6,7-dimethoxyisoquinolinyl)]-4,4-diphenylheptane hydrochloride: Anal. Calcd for $C_{42}H5_2[N_3O3–2HCl$ $1.25H_2O$: C, 66.26; H, 7.48; N, 5.5 1; Found: C, 66.02; H, 6.96; N, 5.52.

Example 82

7-[N-3-(4-Fluorophenyl)propionyl]amino-1-[N-(1,2,3,4-tetrahydro-1-[3-N-(biscyclobutylamino)propyll-6,7-dimethoxyisoquinolinyl)1 4.4-diphenylheptane dihydrochloride The procedure described in example 28 was used but using an excess of cyclobutanone in the reductive alkylation step. After workup and chromatographic purification 7-[N-3-(4-fluoro- phenyl)propionyl]amino-1-[N-(1,2,3,4-tetrahydro-1-[3-N-(biscyclobutylamino)propyl]-6,7-dimethoxyisoquinolinyl)]-4,4-diphenylheptane was obtained: MS showed $(M+H)^+$ @ 774. The hydrochloride salt was prepared as in example 4 to give 7-[N-3-(4-fluorophenyl)propionyl]- amino-1-[N-(1,2,3,4-tetrahydro-1-[3-N-(biscyclobutylamino)propyl]-6,7-dimethoxyisoquinolinyl)]-4,4-diphenylheptane dihydrochloride: Anal. Calcd for $C_5OH_{64}[N_3O_3$ $2HCl1H_2O$: C, 68.01; H, 7.99; N, 4.75; Found: C, 67.37; H, 7.79; N, 4.82.

Example 83

7-[N-3-(4-Fluorophenyl)propionyl]amino-1-[N-(1,2,3,4-tetrahydro-1-r3-N-(biscycloipropylmethylamino)lpropyll-6,7-dimethoxyisoquinolinyl)l-4,4-diphenylheptane dihydrochloride The procedure described in example 82 was used but substituting cyclopropylcarbox- aldehyde for cyclobutanone. After workup and chromatographic purification 7-[N-3-(4-fluoro- phenyl)propionyl]amino-1-[N-( 1.2.3,4-tetrahydro-1-[3-NV-(biscyclopropylmethyl-amino)propyl)-6,7-dimethoxyisoquinolinyl)]-4,4-diphenylheptane was obtained: MS showed (M+H) @ 775. The hydrochloride salt was prepared as in example 4 to give 7-[NA-3-(4-fluorophenylpropionyl)]- I-[N-(1,2,3,4-tetrahydro-1-[3-N-(biscyclopropylmethylamino)propyl]-6,7-dimethoxyisoquinolinyl)]-4,4-diphenylheptane dihydrochloride: Anal. Calcd for $C_5OH_{64}[N_3O_{3-2}HCl-H_2O$: C, 68.35; H, 7.97; N, 4.78; Found: C, 68.10; H, 7.57; N, 4.83.

Example 84

7-[N-3-(4-Fluorophenyl)propionyl]amino-1-[N-(1,2,3,4-tetrahydro-1-r3-N-(dimethylamino)propnyll-67-dimethoxyisoquinolinul)l-4,4-dinhenylheptane dihydrochloride The procedure described in example 82 was used but substituting formaldehyde for cyclobutanone. After workup and chromatographic purification 7-[N-3-(4-fluorophenyl-propionyl)]amino-1-[N-(1,2,3,4-tetrahydro-1-[3-N-(dimethylamino)propyl]-6,7-dimethoxy- isoquinolinyl)]-4,4-diphenylheptane dihydrochloride was obtained: MS showed $(M+H)^+$ @ 693. The hydrochloride salt was prepared as in example 4 to give 7-[N-3-(4-fluorophenyl)propionyl]- amino-1-[N-(1,2,3,4-tetrahydro-1-[3-N-(dimethylamino)propyl]-6,7-dimethoxyisoquinolinyl)]- 4,4-diphenylheptane dihydrochloride.

Example 85

7-[N-3-(4-Fluorophenyl)propionyl]amino-1-[N-(1,2,3,4-tetrahydro- -r3-N-(isoprovyl)-propyll-6,7-dimethoxyisoquinolinyl)]-4,4-diphenylheptane dihydrochloride The procedure described in example 82 was used but substituting acetone for cyclobutanone. After workup and chromatographic purification 7-[N-3-(4-fluorophenyl-propionyl)]amino-1-[N-(1,2,3,4-tetrahydro-1-(3-(N-isopropyl)propyl)-6,7-dimethoxy- isoquinolinyl)]-4,4-diphenylheptane dihydrochloride was obtained: MS showed $(M+H)^+$ @ 708. The hydrochloride salt was prepared as in example 4 to give 7-[N-3-(4-fluorophenyl)propionyl]- 1-[N-(1,2,3,4-tetrahydro-1-[3-N-(isopropyl)-propyl]-6,7-dimethoxyisoquinolinyl)]-4,4- diphenylheptane dihydrochloride.

Example 86

7-[N-3-(4-Fluorophenyl)propionyl]amino-1-[N-(1,2,3,4-tetrahydro-1-(5-A-phthalimidopentyl)-6,7-dimethoxyisoguinolinyl)]-4,4-diphenylheptane hydrochloride The procedure described in example 22 was used but substituting 6-N-phthalimido- hexanoic acid for N-phthalimidoglycine in step 1. After work up and chromatographic purification 7-[N-3-(4-fluorophenyl)propionyl]amino-1-[N-(1,2,3,4-tetrahydro-1- (5-N-phthalimidopentyl)-6,7-dimethoxyisoquinolinyl)]-4,4-diphenylheptane was obtained: MS showed $(M+H)^+$ @ 824. The hydrochloride salt was prepared as in example 4 to give 7-[N-3-(4-fluorophenyl)propionyl]-1-[N-(1,2,3,4-tetrahydro-1-(5-N-phthalimidopentyl)- 6,7-dimethoxyisoquinolinyl)]-4,4-diphenylheptane hydrochloride.

Example 87

7-[N-3-(4-Fluorophenyl)propionyl]amino-1-[N-(1,2,3,4-tetrahydro-1-(5-aminopentyl)-6,7-dimethoxyisoguinolinyl)1–4.4-diphenylhentane dihydrochloride The procedure described in example 22 for cleavage of the phthalimido group from 7-[N-3-(4-fluorophenyl)propionyl]amino-1-[N-(1,2,3,4-tetrahydro-1-(5-YV-phthalimidopentyl)- 6,7-dimethoxyisoquinolinyl)]-4,4-diphenylheptane was used. After work up and chromatographic 7-[N-3-(4-fluorophenyl)propionyl]amino-1-[.N-(1,2,3 4-tetrahydro-1- (5-aminopentyl)-6,7-dimethoxyisoquinolinyl)]-4,4-diphenylheptane was obtained: MS showed (M+H)- @ 694. The hydrochloride salt was prepared as in example 4 to give 7-[N-3-(4-fluorophenyl)propionyl]-amino-1-[N-(1,2,3,4-tetrahydro-1-(5-ami nopentyl)-6,7-dimethoxyiso- quinolinyl)]-4,4-diphenylheptane dihydrochloride: Anal. Calcd for $C_{44}H_{56}$

[N₃O₃2HCl-H₂O: C. 67.33: H. 7.70; n, 5.35; Found: C, 67.10; H. 7.24; N, 5.24.

Example 88

7-[N-3-(4-Fluorophenyl)propionyl]amino-1-[N-(1,2, 3,4-tetrahydro-1-r5-N-(bis-cyclobutylamino)pentyll-6,7-dimethoxyisoguinolinyl)]-4,4-diph enylheptane dihydrochloride

The procedure described in example 82 was used but substituting 7-[N-3-(4-fluoro- phenyl)propionyl]amino-1-[N-(1,2,3,4-tetrahydro-1-(5-aminopentyl)-6,7-dimethoxyisoquinolinyl)]-4,4-diphenylheptane for 7-[N-3-(4-fluorophenyl)propionyl]amino-1-[N-(1,2,3,4- tetrahydro-1-(3-aminopropyl)-6,7-dimethoxyisoquinolinyl)]-4,4-diphenylheptane. After work up and chromatographic purification 7-[N-3-(4-fluorophenyl)propionyl]amino-1-[N-(1,2,3,4- tetrahydro-1-[5-N-(biscyclobutylamino)pentyl]-6,7-dimethoxyisoquinoliny)1-4,4-diphenyl- heptane was obtained: MS showed (M+H)⁺ @ 802. The hydrochloride salt was prepared as in example 4 to give 7-[N-3-(4-fluorophenyl)propionyl]amino-1-[N-(1,2,3,4-tetrahydro-1-[5-N-(biscyclobutylamino)pentyl]-6,7-dimethoxyisoquinolinyl)]-4,4-diphenylheptane dihydrochloride.

Example 89

7-[N-3-(4-Fluorophenyl)Propionyl]amino-1-[N-(1,2, 3,4-tetrahydro-1-[5-N-(biscyclopropylmethylamino) pentyll-6,7-dimethoxyisoguinolinyl)]-4,4-diphenylheptane dihydrochloride

The procedure described in example 88 was used but substituting cyclopropylcarbox- aldehyde for cyclobutanone. After work up and chromatographic purification 7-[N-3-(4-fluoro- phenyl)propionyl]amino-1-[N-( I ,2,3,4-tetrahydro-1-[5-N-(biscyclopropylmethylamino)pentyl]-6,7-dimethoxyisoquinolinyl)]-4,4-diphenylheptane was obtained: MIS showed (Mv+H)⁺ @ 802. The hydrochloride salt was prepared as in example 4 to give 7-[YV-3-(4-fluorophenyl)- propionyl]amino-1-[N-(1,2,3,4-tetrahydro-1-[5-N-(biscyclopropylmethyl-amino)pentyl]-6,7-dimethoxyisoquinolinyl)]-4,4-diphenylheptane dihydrochloride: Anal. Calcd for C₅₂H₆₈[N₃O₃,2HCL,H₂O: C, 68.55; H, 8.18; N, 4.61; Found: C, 67.87; H. 7.84; N. 4.59.

Example 90

7-[N-3-(4-Fluorophenyl)lpropionyl]amino-1-[N-(1,2, 3,4-tetrahydro-1-r5-N-(dimethylamino)pentyll-6,7-dimethoxyisoguinolinyl)l-4,4-diphenylheptane dihydrochloride

The procedure described in example 88 was used but substituting formaldehyde for cyclobutanone. After work up and chromatographic purification 7-[N-3-(4-fluorophenyl)-propionyl]amino-1-[N-(1,2,3,4-tetrahydro-1-[5-NV-(dimethylamino)pentyl]-6,7-dimethoxy- isoquinolinyl)]-4,4-diphenylheptane was obtained: MS showed (M+H)⁺ @ 722. The hydrochloride salt was prepared as in example 4 to give 7-[N-3-(4-fluorophenyl)propionyl]- amino-1-[N-(1,2,3,4-tetrahydro-1-[5-N-(dimethylamino)pentyl]-6,7-dimethoxyisoquinolinyl)]- 4,4-diphenylheptane dihydrochloride.

Example 91

7-[N-3-(4-Fluorophenyl)Propionyl]amino-1-[N-(1,2, 3,4-tetrahydro-1-[5-N-(isolpropylamino)pentyll-6,7-dimethoxyisoguinolinyl)l-4,4-diphenylheptane dihydrochloride

The procedure described in example 88 was used but substituting acetone for cyclobutanone. After work up and chromatographic purification 7-[N-3-(4-fluorophenyl-propionyl)]amino-1-[N-(1,2,3,4-tetrahydro-1-[5-YV-(isopropylamino)pentyl]-6,7-dimethoxy- isoquinolinyl)]-4,4-diphenylheptane was obtained: MS showed (M+H)⁺ @ 736. The hydrochloride salt was prepared as in example 4 to give 7-[N-3-(4-fluorophenyl)propionyl]- amino-1-[N-(1,2,3,4-tetrahydro-1-[5-N-(isopropylamino)pentyl]-6,7-dimethoxyisoquinolinyl)]- 4,4-diphenylheptane dihydrochloride: Anal. Calcd for C₄₇H₆₂[N₃O₃,0.75 H?O: C, 75.15; H, 10.33: N. 5.59; Found: C, 74.99; H. 8.34: N, 5.51.

Example 92

7-[N-3-(4-Fluorophenyl)propionyl]-1-[N-(1,2,3,4-tetrahydro-1-cyclobutyl-6-fluoro-7-methoxyisoguinolinyl )]-4,4-diphenylheptane hydrochloride

The procedure described in example 9 was used but substituting 1,2,3,4-tetrahydro-1- cyclobutyl-6-fluoro-7-methoxyisoquinoline for 1,2,3,4-tetrahydro-1-cyclobutyl-6, 7-dimethoxy- isoquinoline. After workup and chromatographic purification 7-[N-3-(4-fluorophenyl)- propionyl]-1-[N-(1,2,3,4-tetrahydro-1-cyclobutyl-6-fluoro-7-methoxyisoquinolinyl)]- 4,4-diphenylheptane was obtained: MS showed (M+H)⁺ @ 651; ¹H-NMR (CDCl₃, δ): 1.05–1.21 (m, 4H), 1.62–1.90 (m, 5H) 1.90–2.17 (m, 5H), 2.25–2.58 (m, 6H), 2.60–2.76 (m, 2H), 2.84–2.92 (t, 2H), 2.97–3.09 (m, 1H), 3.09–3.20 (m, 3H), 3.81 (s, 3H), 5.11 (broad m, 1H), 6.47–6.53 (d, 1H), 6.69–6.76 (d, 1H), 6.86–6.95 (t, 2H), 7.05–7.29 (m, 12H); 1R (MIC) u 3310, 2940, 1630, 1510 cm⁻¹. The hydrochloride salt was prepared as in example 4 to give 7-[N-3-(4- fluorophenyl)propionyl]-1-[N-(1,2,3,4-tetrahydro-1-cyclobutyl-6-fluoro-7-methoxyisoquinolinyl)]-4,4-diphenylheptane hydrochloride.

Example 93

7-[N-3-(4-Fluorophenyl)iropionyl]amino-1-r(N-F 1, 2,3,4-tetrahydro-1-(4-N-phthalimidobutyl)-6-methyl-7-methoxy isoguinolinyl)]-4,4-diphenylheptane

The synthetic procedure described in example 24 was used but substituting 1,2,3,4-tetrahydro-1-(4-N-phthalimidobutyl)-6-methyl-7-methoxyisoquinoline for substituting 1,2,3,4-tetrahydro-1-(4-N-phthalimidobutyl)-6, 7-dimethoxyisoquinoline. After workup and purification with a silica gel column chromatography 7-[N-3-(4-fluorophenyl)propionyl]amino- 1-[(N-[1,2,3-,4-tetrahydro-1-(4-N-phthalimidobutyl)-6-methyl-7-methoxyisoquinolinyl)]-4,4- diphenylheptane was obtained: MS showed (M+H)⁺ (794; ¹H-NMR (CDCl₃, δ): 1.08–1.23 (m. 4H), 1.38–1.51 (m, 2H), 1.56–1.79 (m, 5H), 1.98–2.13 (m, 3H), 2.14 (s, 3H), 2.29–2.52 (m, SH), 2.56–2.74 (m, 2H), 2.87–2.93 (t, 2H), 2.95–3.08 (m, 1H), 3.09–3.24 (m, 2H), 3.29–3.37 (m, 1H), 3.61–3.72 (t, 2H), 3.78 (s, 3H), 5.42–5.50 (brs, 1H), 6.43 (s, 1H), 6.58 (s, 1H), 6.87–6.95 (t,

Example 94

7-[N-3-(4-Fluorophenyl)Propionyl]-1-[(N-(1,2,3,4-tetrahydro-1-(4-aminobutyl)-6-methyl-7-methoxyisoguinolinyl)l-4,4-diphenylheptane

The synthetic procedure described in example 22 for the cleavage of the phthalimido group was used. After workup and purification with a silica 7-[N-3-(4-fluorophenyl) propionyl]- amino-1-[(N-[1,2,3,4-tetrahydro-1-(4- aminobutyl)-6-methyl-7-methoxyisoquinolinyl)]-4,4-diphenylheptane was obtained: MS showed (M+H)+ @ 664; $^1$H-NMR (CDCl$_3$, δ): 1.04–1.28 (m, 4H), 1.34–1.76 (m, 6H), 1.95–2.13 (m, 3H), 2.14 (s, 3H), 2.30–2.41 (m, 3H), 2.41–2.48 (t, 2H), 2.56–2.76 (m, 4H), 2.82–2.92 (t, 2H), 2.95–3.22 (m, 6H), 3.32–3.41 (broad q, 1H), 3.27 (s, 3H), 5.65–5.73 (broad t, 1H), 6.41 (s, 1H), 6.78 (s, 1H), 6.87–6.94 (t, 2H), 7.07–7.28 (m, 12H); IR (KBr) u 3280,2940, 1630, 1510 cm$^{-1}$.

Example 95

7-[N-3-(4-Fluorophenyl)propionyl]amino-1-r(N-(V1,2,3,4-tetrahydro-1-(4-N-isopropylaminobutyl)-6-methyl-7-methoxyisoquinolinyl)l-4,4-diphenylheptane 7-[N-3-(4-Fluorophenyl)propionyl]amino-1-[(N-(1,2,3,4-tetrahydro-1-(4-aminobutyl)-6-methyl-7-methoxyisoquinolinyl)]-4,4-diphenylheptane was reductive alkylated upon treatment with acetone and sodium cyanoborohydride as described in example 26. After workup and purification with a silica 7-[N-3-(4-fluorophenyl) propionyl]amino-1-[(N-[1,2,3,4-tetrahydro- 1-(4-V-isopropylaminobutyl)-6-methyl-7-methoxyisoquinolinyl)]-4,4-diphenylheptane was obtained: MS showed (M+H)+ @ 706; $^1$H-NMR (CDCl$_3$, δ): 1.02–1.29 (m, 5H), 1.13–1.16 (d, 6H), 1. 33–1.48 (m, 2H), 1.51–1.75 (m, 4H), 1.94–2.12 (m, 4H). 2.14 (s, 3H), 2.28–2.48 (m, 5H), 25 2.53–2.71 (m, 4H), 2.83–3.04 (m, 4H), 3.07–3.18 (broad q, 2H). 3.32–3.42 (m, 1H), 3.77 (s. 3H), 5.52–5.59 (broad t, 1H) 6.41 (s, 1H), 6.78 (s, 1H), 6.88–6.96 (t, 2H), 7.07–7.29 (m, 12H); IR (KBr) u 3280,2940, 1630, 1510 cm$^{-1}$.

Example 96

7-[N-3-(4-Fluorophenyl)propionyl]amino-1-)F(N-(1, 2,3,4-tetrahydro-1-cyclobutyl-6-methyl-7-methoxyisoguinolinyl)1–4.4-diphenylheptane hydrochloride The procedure described in example 92 was used but substituting 1,2.3.4-tetrahydro- 1-cyclobutyl-6-methyl-7-methoxyisoquinoline for 1,2,3,4-tetrahydro-1-cyclobutyl-6-fluoro- 7-methoxyisoquinoline. After workup and purification by a silica gel column 7-[N-3-(4-fluoro- phenyl) propionyl]amino-1-[(N-[ 1,2,3,4-tetrahydro-1-cyclobutyl-6-methyl-7-methoxy-iso- quinolinyl)]-4,4-diphenylheptane: MS showed (M+H)- @ 647; $^1$H-NMR (CDCl$_3$, δ): 1.04–1.22 (m, 4H), 1.62–2.0 (m, 6H), 2.0–2.15 (m, 4H), 2.17 (s. 3H), 2.23–2.58 (m, 6H), 2.61–2.77 (m, 2H), 2.83–2.92 (t, 2H), 2.98–3.08 (m, 1H), 3.08–3.21 (m, 3H), 3.75 (s, 3H), 5.06–5.10 (broad t, 1H), 6.39 (s, 1H), 6.79 (s, 1H), 6.85–6.96 (t, 2H), 7.05–7.28 (m, 12H); IR (KBr) v) 3320, 2940, 1635, 1510 cm$^{-1}$. The hydrochloride salt was prepared as in example 4 to give 7-[N-3-(4-fluoro- phenyl) propionyl]amino-1-[(N-[ 1,2,3,4-tetrahydro-1-cyclobutyl-6-methyl-7-methoxy- 5 isoquinolinyl)]-4,4-diphenylheptane hydrochloride.

LHRH ANTAGONIST ACTIVITY

Representative compounds of the present invention were evaluated in vitro for potency against for LHRH rat pituitary receptor binding [pK, ]. Methods for the assay procedures are described in F. Haviv, et al. *J Med. Chem.*, 32: 2340–2344 (1989).

Values of pK, are the negative logarithms of the equilibrium dissociation constant of the particular antagonist test compound for the receptor binding. Typically values of 7.0 or greater are indicative of good LHRH antagonist potency, with values of 8.0 or greater being preferred. Leuprolide LHRH agonist, disclosed and claimed in U.S. Pat. No. 4,005, 063, has the structure 5-oxo-Pro$^1$-His$^2$-Trp$^3$-Ser$^4$-Tyr -D-Leu$^6$-Leu$^7$-Arg$^8$-Pro$^9$-NHEt.

Results for the assay of representative compounds within the scope of the invention are summarized in Tables 1–3. pK[ values for compounds of formula (I) wherein I is 2, m is 3, p is 1, X is flourine, Y is hydrogen, R$_2$ is hydrogen, and W and Z are both -OCH$_3$, as represented by formula (V) below

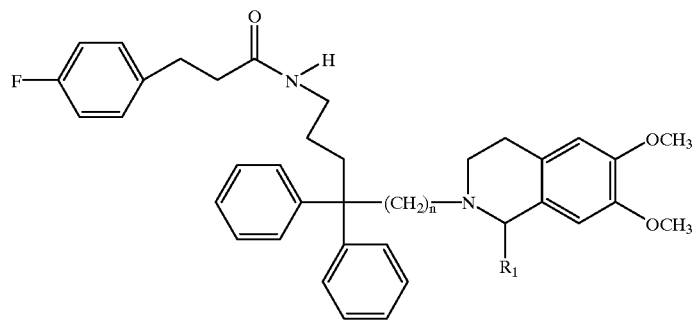

(V)

are described by the corresponding value of n and the substituent R$_1$ in Table 1.

TABLE 1

| Example | n | R$_1$ | pK$_I$ |
|---|---|---|---|
| 1 | 3 | CH$_3$ | 8.80 |
| 2 | 3 | (R)CH$_3$ | 8.25 |
| 3 | 3 | (S)CH$_3$ | 7.0 |
| 4 | 3 |  | 9.87 |

TABLE 1-continued

| Example | n | R₁ | pK_I |
|---|---|---|---|
| 5 | 3 | -CH(CH₃)- (ethyl branch) | 8.80 |
| 6 | 3 | -CH(CH₃)₂ (isopropyl) | 8.80 |
| 7 | 3 | phenyl | 7.34 |
| 8 | 3 | cyclopentyl | 9.41 |
| 9 | 3 | cyclobutyl | 10.07 |
| 10 | 3 | cyclohexyl | 8.54 |
| 11 | 3 | -CH₂CN | 8.71 |
| 12 | 3 | -CH₂OCH₃ | 8.08 |
| 13 | 3 | -CH₂CH₂OCH₂C₆H₅ | 8.46 |
| 14 | 3 | 4-methoxyphenyl | 8.14 |
| 15 | 3 | 4-aminophenyl | 8.53 |
| 16 | 3 | 4-(isopropylamino)phenyl | 8.53 |
| 17 | 3 | benzyl | 8.56 |
| 18 | 3 | 4-chlorobenzyl | 7.41 |
| 19 | 3 | 4-methoxybenzyl | 8.23 |
| 20 | 3 | phenethyl | 7.60 |
| 21 | 3 | 4-aminobenzyl | 10.14 |
| 22 | 3 | -CH₂NH₂ | 9.24 |
| 23 | 3 | -CH₂NH-CH(CH₃)₂ | 8.91 |
| 24 | 3 | -(CH₂)₄-phthalimidyl | 9.39 |
| 25 | 3 | -(CH₂)₄-NH₂ | 9.73 |

TABLE 1-continued

| Example | n | R₁ | pK_I |
|---|---|---|---|
| 26 | 3 |  -NH-CH(CH₃)₂ | 8.56 |
| 27 | 3 | -NH-CH₂-cyclopropyl | 10.0 |
| 28 | 3 | -NH-cyclobutyl | 9.60 |
| 29 | 3 | -NH-CH₂-CH(CH₃)₂ | 8.60 |
| 30 | 3 | -N(H)-CH₂-CH(CH₃)₂ (branched) | 8.00 |
| 31 | 3 | -NH-CH(CH₃)-phenyl | 8.40 |
| 32 | 3 | -N(CH₂-cyclopropyl)₂ | 9.20 |
| 33 | 3 | -N(CH₃)₂ | 8.9 |
| 34 | 3 | -NH-C(=O)CH₃ | 8.63 |
| 35 | 3 | -NH-C(=O)-(3-pyridyl) | 8.61 |
| 36 | 3 | cyclohexyl-CH₂-phthalimide derivative | 8.27 |
| 37 | 3 | cyclohexyl-CH₂-NH₂ | 8.40 |
| 38 | 3 | cyclohexyl-CH₂-NH-CH(CH₃)₂ | 8.80 |
| 39 | 3 | phenyl-CH₂-NH-CH(CH₃)₂ | 8.0 |
| 40 | 3 | phenyl-CH₂-NH-cyclobutyl | 7.70 |
| 41 | 3 | phenyl-CH₂-NH-CH₂-cyclopropyl | 7.80 |
| 42 | 3 | phenyl-CH₂-N(CH₂-cyclopropyl)₂ | 8.30 |
| 43 | 3 | phenyl-CH₂-NH-C(=O)CH₃ | 8.10 |
| 44 | 2 | CH₃ | 7.15 |
| 45 | 4 | CH₃ | 7.45 |

Examples 46–71 pKi values for compounds of formula (I) wherein I is 2. m is 3, n is 3. X is fluorine Y is hydrogen, and an isoquinolinyl moiety is denoted by R as represented below by formula (VI):

(IV)
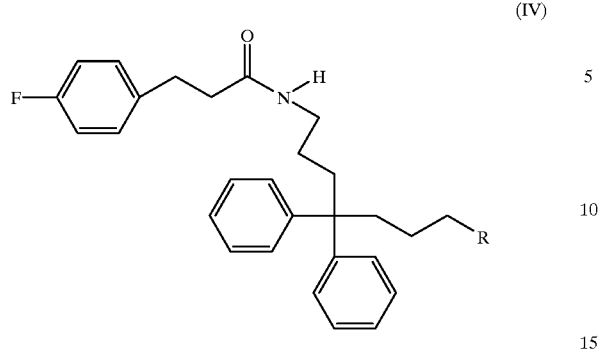
according to the substituent R in Table 2 below.
TABLE 2
| Example | R | $pK_I$ |
|---|---|---|
| 46 | 1,2,3,4-tetrahydroisoquinolin-2-yl, 1-CH₃, 6,7-di-OH | 7.81 |
| 47 | 1,2,3,4-tetrahydroisoquinolin-2-yl, 1-CH₃ | 7.84 |
| 48 | 6,7-methylenedioxy-1-methyl-1,2,3,4-tetrahydroisoquinolin-2-yl | 8.00 |
| 49 | 6,7-ethylenedioxy-1-methyl-1,2,3,4-tetrahydroisoquinolin-2-yl | 7.90 |
| 50 | 6-methoxy-1-methyl-1,2,3,4-tetrahydroisoquinolin-2-yl | 8.60 |
| 51 | 7-methoxy-1-methyl-1,2,3,4-tetrahydroisoquinolin-2-yl | 8.98 |

TABLE 2-continued

| Example | R | pK$_I$ |
|---|---|---|
| 52 | 7-Cl, 1-CH$_3$-tetrahydroisoquinolin-2-yl | 8.45 |
| 53 | 7-F, 1-CH$_3$-tetrahydroisoquinolin-2-yl | 7.84 |
| 54 | 7-NO$_2$, 1-CH$_3$-tetrahydroisoquinolin-2-yl | 8.36 |
| 55 | 7-NHCOCH$_3$, 1-CH$_3$-tetrahydroisoquinolin-2-yl | 8.06 |
| 56 | 6,7-diCl, 1-CH$_3$-tetrahydroisoquinolin-2-yl | 8.43 |
| 57 | 6-Cl, 7-F, 1-CH$_3$-tetrahydroisoquinolin-2-yl | 8.60 |
| 58 | 6,7-di(OCOCH$_3$), 1-CH$_3$-tetrahydroisoquinolin-2-yl | 7.91 |
| 59 | 6-Br, 7-OCH$_3$, 1-CH$_3$-tetrahydroisoquinolin-2-yl | 8.72 |
| 60 | 6-F, 7-OCH$_3$, 1-CH$_3$-tetrahydroisoquinolin-2-yl | 8.77 |

TABLE 2-continued

| Example | R | pK$_I$ |
|---|---|---|
| 61 | 6-OCH$_3$, 7-Br, 1-CH$_3$ tetrahydroisoquinoline | 8.43 |
| 62 | 6-CH$_3$, 7-OCH$_3$, 1-CH$_3$ tetrahydroisoquinoline | 9.30 |
| 63 | 6-CO$_2$CH, 7-OCH$_3$, 1-CH$_3$ tetrahydroisoquinoline | 8.17 |
| 64 | 6-Br, 7-OCH$_3$, 1-cyclobutyl tetrahydroisoquinoline | 8.22 |
| 65 | 3-CH$_3$, 6-OCH$_3$, 7-OCH$_3$, 1-CH$_3$ tetrahydroisoquinoline | 10.44 |
| 66 | 3-CH$_3$, 6-OCH$_3$, 7-OCH$_3$ tetrahydroisoquinoline | 9.21 |
| 67 | 6-OCH$_3$, 7-OCH$_3$, 1,1-(CH$_3$)$_2$ tetrahydroisoquinoline | 8.60 |
| 68 | 3-CH$_3$, 7-OCH$_3$, 1-CH$_3$ tetrahydroisoquinoline | 8.60 |

TABLE 2-continued

| Example | R | pK$_I$ |
|---|---|---|
| 69 | *structure: 1-methyl-7,8-dimethoxy-2,3,4,5-tetrahydro-1H-2-benzazepine* | 7.90 |
| 70 | *structure: methyl 1-methyl-7-methoxy-1,2,3,4-tetrahydroisoquinoline-3-carboxylate* | 7.66 |
| 71 | *structure: N-(2-pyrrolidin-1-ylethyl)-1-methyl-7-methoxy-1,2,3,4-tetrahydroisoquinoline-3-carboxamide* | 7.80 |

Examples 72–80 pK$_I$ values for compounds of formula (I) wherein m is 3, n is 3, p is 1, R$_1$ is methyl, R$_2$ is H, W and Z are both —OCH$_3$, and the substitution of the primary amine is denoted by R$^1$, as represented below by formula (VII)

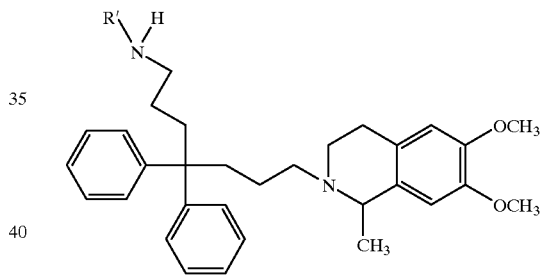
(VII)

are according to the substituent R$^1$ in Table 3 below.

TABLE 3

| Example | R' | pK$_I$ |
|---|---|---|
| 72 | *structure: 3-phenylpropanoyl* | 8.50 |
| 73 | *structure: 3-(3,4-dichlorophenyl)propanoyl* | 8.66 |

TABLE 3-continued
| Example | R' | pK_I |
|---|---|---|
| 74 | 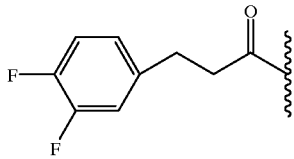 | 11.40 |
| 75 | 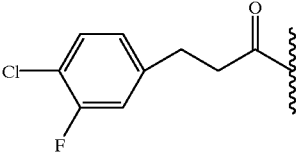 | 11.48 |
| 76 | 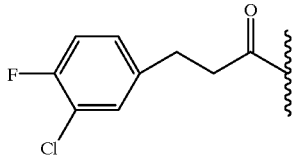 | 8.40 |
| 77 | 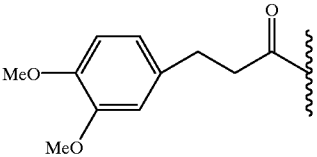 | 8.30 |
| 78 | 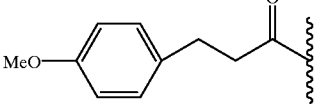 | 9.54 |
| 79 | 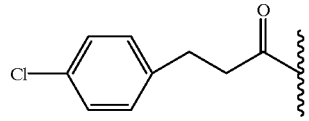 | 9.71 |
| 80 | 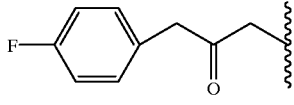 | 11.64 |

What is claimed is:
1. A compound having a formula:

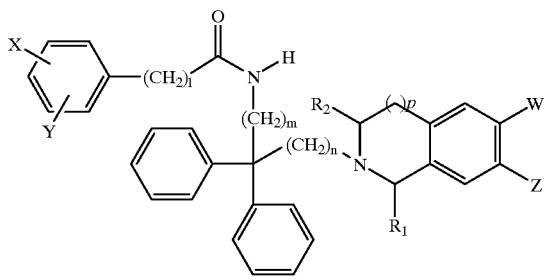

(I)

or a pharmaceutically acceptable salt, ester, or prodrug thereof, wherein:

l, m, and n are each independently 1, 2, 3, or 4;
p is 1 or 2;
$R_1$ is selected from the group consisting of:
 (a) alkyl,
 (b) cycloalkyl,
 (c) aryl,
 (d) cyano,
 (e) —$(CH_2)_q$—$R_4$, wherein q is 0 to 10,
 (f) -cycloalkyl-$R_5$, and
 (g) -aryl-$R_5$;
$R_2$ is selected from the group consisting of:
 (a) alkyld
 (b) hydrogen,
 (c) alkoxycarbonyl,
 (d) hydroxymethyl, and
 (e) —$(CH_2)$,-$R_4$, wherein q is 0 to 10;
$R_4$ is selected from the group consisting of:
 (a) alkyl,
 (b) alkoxy,
 (c) aryl,
 (d) aryloxy,
 (e) cyano,
 (f) cycloalkyl,
 (g) hydroxy,
 (h) halogen,
 (i) phthalimido,
 (j) -cycloalkyl-$R_5$,
 (k) -aryl-$R_5$, and
 (l) —$NR_6R_7$;
$R_5$ is selected from the group consisting of:
 (a) alkyl,
 (b) alkoxy,
 (c) cyano,
 (d) hydroxy,
 (e) halogen,
 (f) trifluoromethyl, and
 (g) —$(CH_2)q$—$NR_6R_7$, wherein q is 0 to 10;
$R_6$ and $R_7$ are independently selected from the group consisting of:
 (a) hydrogen,
 (b) alkyl,
 (c) cycloalkyl, and
 (d) aryl, or
$R_6$ is hydrogen and $R_7$ is a group of the formula -$COR_8$, wherein $R_8$ is selected from the group consisting of:
 (a) alkyl,
 (b) aryl, and
 (c) heterocycle;
X and Y are independently selected from the group consisting of:
 (a) hydrogen,
 (b) halogen,
 (c) alkoxy,
 (d) alkyl, and
 (e) trifluoromethyl; and
W and Z are independently selected from the group consisting of:
 (a) hydrogen,
 (b) hydroxy,
 (c) alkyl,
 (d) alkoxy,
 (e) alkoxycarbonyl,
 (f) nitro,
 (g) N-acyl,
 (h) halogen, and
 (i) trifluoromethyl, or
W and Z taken together form a cyclic ring.

2. A compound according to claim 1, wherein l is 2, m is 3, n is 3, and p is 1.

3. A compound according to claim 1, wherein $R_1$ is selected from the group consisting of alkyl, cycloalkyl, and —$(CH_2)_q$—$R_4$, wherein q is 0 to 10. and $R_4$ is a group of the formula —$NR_6R_7$, wherein $R_6$ and $R_7$ are each independently selected from hydrogen, alkyl, and cycloalkyl.

4. A compound according to claim 3, wherein $R_1$ is selected from the group consisting of methyl, cyclopropyl, cyclobutyl, aminomethyl aminoethyl, aminopropyl aminobutyl. N-[cyclopropylmethyl]aminobutyl, and N-[bis-cyclopropylmethyl]aminobutyl.

5. A compound according to claim 1, wherein R. is selected from the group consisting of hydrogen and methyl.

6. A compound according to claim 1, wherein X and Y are independently selected from the group consisting of hydrogen and halogen.

7. A compound according to claim 1, wherein W and Z are independently selected from the group consisting of hydrogen and methoxy.

8. A compound according to claim 1, selected from the group consisting of:
 (R,S) 7-[N-3-(4-fluorophenyl)propionyl]amino-1-[N-(1,2,3,4-tetrahydro-1-methyl-6,7-dimethoxyisoquinolinyl)]-4,4-diphenylheptane hydrochloride;
 (R) 7-[N-3-(4-fluorophenyl)propionyl]amino-1-[N-(1,2,3,4-tetrahydro-1-methyl-6,7-dimethoxyisoquinolinyl)]-4,4-diphenylheptane hydrochloride;
 (S) 7-[N-3-(4-fluorophenyl)propionyl]amino-1-[N-(1,2,3,4-tetrahydro-1-methyl-6,7-dimethoxyisoquinolinyl)]-4,4-diphenylheptane hydrochloride;
 7-[N-3-(4-fluorophenyl)propionyl]amino-1-[N-(1,2,3,4-tetrahydro-1-cyclopropyl-6,7-dimethoxyisoquinolinyl)]-4,4-diphenylheptane hydrochloride;
 7-[N-3-(4-fluorophenyl)propionyl]amino-1-[N-(1,2,3,4-tetrahydro-1-ethyl-6,7-dimethoxy-isoquinolinyl)]-4,4-diphenylheptane hydrochloride;
 7-[N-3-(4-fluorophenyl)propionyl]amino-1-[N-(1,2,3,4-tetrahydro-1-isopropyl-6,7-dimethoxyisoquinolinyl)]-4,4-diphenylheptane hydrochloride;
 7-[N-3-(4-fluorophenyl)propionyl]amino-1-[N-(1,2,3,4-tetrahydro-1-phenyl-6,7-dimethoxy-isoquinolinyl)]-4,4-diphenylheptane hydrochloride;

7-[N-3-(4-fluorophenyl)propionyl]amino-1-[N-(1,2,34-tetrahydro-1-cyclopentyl-6,7-dimethoxyisoquinolinyl)]-4,4-diphenylheptane hydrochloride;

7-[N-3-(4-fluorophenyl)propionyl]amino-1-[N-(1,2,3,4-tetrahydro-1-cyclobutyl-6,7-dimethoxyisoquinolinyl)]-4,4-diphenylheptane hydrochloride;

7-[N-3-(4-fluorophenyl)propionyl]amino-1-[N-(1,2,3,4-tetrahydro-1-cyclohexyl-6,7-dimethoxyisoquinolinyl)]-4,4-diphenylheptane hydrochloride;

7-[N-(4-fluorophenyl)propionyl]amino-1-[N-(1,2,3,4-tetrahydro-1-cyanomethyl-6,7-dimethoxyisoquinolinyl)]-4,4-diphenylheptane hydrochloride;

7-[N-(4-fluorophenyl)propionyl]amino-1-[N-(1,2,3,4-tetrahydro-1-methoxymethyl-6,7-dimethoxyisoquinolinyl)]-4,4-diphenylheptane hydrochloride;

7-[N-3-(4-fluorophenyl)propionyl]amino-1-[N-(1,2,3,4-tetrahydro-1-benzyloxymethyl-6,7-dimethoxyisoquinolinyl)]-4,4-diphenylheptane hydrochloride;

7-[N-3-(4-fluorophenyl)propionyl]amino-1-[N-(1,2,3,4-tetrahydro-1-(p-methoxy)phenyl-6,7-dimethoxyisoquinolinyl)]-4,4-diphenylheptane hydrochloride;

7-[N-3-(4-fluorophenyl)propionyl]amino-1-[N-(1,2,3,4-tetrahydro-1-(4-aminophenyl)-6,7-dimethoxyisoquinolinyl)]-4,4-diphenylheptane dihydrochloride;

7-[N-3-(4-fluorophenyl)propionyl]amino-1-[N-(1,2,3,4-tetrahydro-1-[4-(N-isopropyl-amino)phenyl]-6,7-dimethoxyisoquinolinyl)]-4,4-diphenylheptane dihydrochloride;

7-[N-3-(4-fluorophenyl)propionyl]amino-1-[N-(1,2,3,4-tetrahydro-1-benzyl-6,7-dimethoxy-isoquinolinyl)]-4,4-diphenylheptane hydrochloride;

7-[N-3-(4-fluorophenyl)propionyl]amino-1-[N-(1,2,3,4-tetrahydro-1-(4-chlorobenzyl)-6,7-dimethoxyisoquinolinyl)]-4,4-diphenylheptane hydrochloride;

7-[N-3-(4-fluorophenyl)propionyl]amino-1-[N-(1,2,3,4-tetrahydro-1-(4-methoxybenzyl)-6,7-dimethoxyisoquinolinyl)]-4,4-diphenylheptane hydrochloride;

7-[N-3-(4-fluorophenyl)propionyl]amino-1-[N-(1,2,3,4-tetrahydro-1-phenethyl-6,7-dimethoxyisoquinolinyl)]-4,4-diphenylheptane hydrochloride;

7-[N-3-(4-fluorophenyl)propionyl]amino-1-[N-(1,2,3,4-tetrahydro-1-(4-aminobenzyl)-6,7-dimethoxyisoquinolinyl)]-4,4-diphenylheptane dihydrochloride;

7-[N-3-(4-fluorophenyl)propionyl]amino 1-[N-(1,2,3,4-tetrahydro-1-aminomethyl-6,7-dimethoxyisoquinolinyl)]-4,4-diphenylheptane hydrochloride;

7-[N-3-(4-fluorophenyl)propionyl]amino-1-[N-(1,2,3,4-tetrahydro-1-(N-isopropyl-aminomethyl)-6,7-dimethoxyisoquinolinyl)]-4,4-diphenylheptane dihydrochloride;

7-[N-3-(4-fluorophenyl)propionyl]amino-1-[N-(1,2,3,4-tetrahydro-1-(4-N-phthalimido-butyl)-6,7-dimethoxyisoquinolinyl)]-4,4-diphenylheptane hydrochloride;

7-[N-3-(4-fluorophenyl)propionyl]amino-1-[N-(1,2,3,4-tetrahydro-1-(4-aminobutyl)-6,7-dimethoxyisoquinolinyl)]-4,4-diphenylheptane dihydrochloride;

7-[N-3-(4-fluorophenyl)propionyl]amino-1-[N-(1,2,3,4-tetrahydro-1-[4-(N-isopropyl-amino)butyl]-6,7-dimethoxyisoquinolinyl)]-4,4-diphenylheptane dihydrochloride;

7-[N-3-(4-fluorophenyl)propionyl]amino-1-[N-(1,2,3,4-tetrahydro-1-[4-(N-cyclopropyl-methylam ino)butyl]-6,7-dimethoxyisoquinolinyl)]-4,4-diphenylheptane dihydrochloride;

7-[N-3-(4-fluorophenyl)propionyl]amino-1-[N-(1,2,3,4-tetrahydro-1-[4-(N-cyclobutyl-amino)butyl]-6,7-dimethoxyisoquinolinyl)]-4,4-diphenylheptane dihydrochloride;

7-[N-3-(4-fluorophenyl)propionyl]amino-1-[N-(1,2,3,4-tetrahydro-1-[4-(N-isobutyl-amino)butyl]-6,7-dimethoxyisoquinolinyl)]-4,4-diphenylheptane dihydrochloride;

7-[N-3-(4-fluorophenyl)propionyl]amino-1-[N-(1,2,3,4-tetrahydro-1-[4-(N-isopentyl-amino)butyl]-6,7-dimethoxyisoquinolinyl)]-4,4-diphenylheptane dihydrochloride;

7-[N-3-(4-fluorophenyl)propionyl]amino-1-[N-(1,2,3,4-tetrahydro-1-[4-(N-alpha-methyl-benzylamino)butyl]-6,7-dimethoxyisoquinolinyl)]-4,4-diphenylheptane dihydrochloride;

7-[N-3-(4-fluorophenyl)propionyl]amino 1-[N-(1,2,3,4-tetrahydro-1-[4-(N,N-dicyclopropyl-methylamino)butyl]-6,7-dimethoxyisoquinolinyl)]-4,4-diphenylheptane dihydrochloride;

7-[N-3-(4-fluorophenyl)propionyl]amino-1-[N-(1,2,3,4-tetrahydro-1-[4-(N, N-dimethyl-amino)butyl]-6,7-dimethoxyisoquinolinyl)]-4,4-diphenylheptane dihydrochloride;

7-[N-3-(4-fluorophenyl)propionyl]amino-1-[N-(1,2,3,4-tetrahydro-1-[4-(N-acetyl-10 amino)butyl]-6,7-dimethoxyisoquinolinyl)]-4,4-diphenylheptane hydrochloride;

7-[N-3-(4-fluorophenyl)propionyl]amino-1-[N-(1,2,3,4-tetrahydro-1-[4-(N-nicotinyl-amino)butyl]-6,7-dimethoxyisoquinolinyl]-4,4-diphenylheptane hydrochloride;

7-[N-3-(4-fluorophenyl)propionyl]amino 1-[N-(1,2,3,4-tetrahydro-1-[4-(N-phthalimido-methyl]cyclohexyl-6,7-dimethoxyisoquinolinyl)]-4,4-diphenylheptane hydrochloride;

7-[N-3-(4-fluorophenyl)propionyl]amino-1-[N-(1,2,3,4-tetrahydro-1-[4-aminomethyl-cyclohexyl)-6,7-dimethoxyisoquinolinyl)]-4,4-diphenylheptane dihydrochloride;

7-[N-3-(4-fluorophenyl)propionyl]arino-1-[N-(1,2,3,4-tetrahydro-1-[4-N-isopropyl amino-methyl)cyclohexyl-6,7-dimethoxyisoquinolinyl)]-4,4-diphenylheptane dihydrochloride;

7-[N-3-(4-fluorophenyl)propionyl]amino-1-[N-(1,2,3 4-tetrahydro-1-[4-N-phthalimido-20 methyl)phenyl-6,7-dimethoxyisoquinolinyl)]-4,4-diphenylheptane hydrochloride;

7-[N-3-(4-fluorophenyl)propionyl]amino-1-[N-(1,2,3,4-tetrahydro-1-[4-aminomethyl-phenyl)-6,7-dimethoxyisoquinolinyl)] -4,4-diphenylheptane dihydrochloride;

7-[N-3-(4-fluorophenyl)propionyl]amino 1-[N-(1,2,3,4-tetrahydro-1-[4-N-isopropylamino-methyl)phenyl-6,7-dimethoxyisoquinolinyl)]-4,4-diphenylheptane dihydrochloride;

7-[N-3-(4-fluorophenyl)propionyl]amino-1-[N-(1,2,3,4-tetrahydro-1-[4-N-cyclobutylamino-meth,,l)phenyl-6,7-dimethoxyisoquinolinyl)]-4,4-diphenylheptane dihydrochloride;

7-[N-3-(4-fluorophenyl)propionyl]amino-1-[N-(1,2,3,4-tetrahydro-1-[4-N-cyclopropyl-methylaminomethyl)phenyl-6,7-dimethoxyisoquinolinyl)]-4,4 dihydrochloride;

7-[N-3-(4-fluorophenyl)propionyl]amino-1-[N-(1,2,3,4-tetrahydro-1-[4-N-biscyclopropyl-methylaminomethyl)phenyl-6,7-dimethoxyisoquinolinyl)]-4,4-diphenylheptane dihydrochloride;

7-[N-3-(4-fluorophenyl)propionyl]amino-1-[N-(1,2,3,4-tetrahydro-1-[4-N-acetylamino-methyl)phenyl-6,7-dimethoxyisoquinolinyt)]-4,4-diphenylheptane hydrochloride;

7-[N-3-(4-fluorophenyl)propionyl]amino-1-[N-(1,2,3,4-tetrahydro-1-methyl-6,7-dihydroxy-isoquinolinyl)]-4,4-diphenylheptane hydrochloride;

7-[N-3-(4-fluorophenyl)propionyl]amino-1-[N-(1,2,3,4-tetrahydro-1-methylisoquinolinyl)]-4,4-diphenylheptane hydrochloride;

7-[N-3-(4-fluorophenyl)propionyl]amino-1-[N-(1,2,3,4-tetrahydro-1-methyl-6,7-dioxalane-isoquinolinyl)]-4,4-diphenylheptane hydrochloride;

7-[N-3-(4-fluorophenyl)propionyl]amino-1-[N-(1,2,3,4-tetrahydro-1-methyl-6,7-dioxane-isoquinolinyl)]-4,4-diphenylheptane hydrochloride;

7-[N-3-(4-fluorophenyl)propionyl]amino-1-[N-(1,2,3,4-tetrahydro-1-methyl-6-methoxy-isoquinolinyl)]-4,4-diphenylheptane hydrochloride;

7-[N-3-(4-fluorophenyl)propionyl]amino-1-[N-(1,2,3,4-tetrahydro-1-methyl-7-methoxy-isoquinolinyl)]-4,4-diphenylheptane hydrochloride;

7-[N-3-(4-fluorophenyl)propionyl]amino-1-[N-(1,2,3,4-tetrahydro-1-methyl-7-chloro-isoquinolinyl)]-4,4-diphenylheptane hydrochloride;

7-[N-3-(4-fluorophenyl)propionyl]amino-1-[N-(1,2,3,4-tetrahydro-1-methyl-7-fluoro-isoquinolinyl)]-4,4-diphenylheptane hydrochloride;

7-[N-3-(4-fluorophenyl)propionyl]amino-1-[N-(1,2,3,4-tetrahydro-1-methyl-7-nitro-isoquinolinyl)]-4,4-diphenylheptane hydrochloride;

7-[N-3-(4-fluorophenyl)propionyl]amino-1-[N-(1,2,3,4-tetrahydro-1-methyl-7-acetylamino-isoquinolinyl)]-4,4-diphenylheptane hydrochloride;

7-[N-3-(4-fluorophenyl)propionyl]amino-1-[N-(1,2,3,4-tetrahydro-1-methyl-6,7-dichloro-isoquinolinyl)]-4,4-diphenylheptane hydrochloride;

7-[N-3-(4-fluorophenyl)propionyl]amino-1-[N-(1,2,3,4-tetrahydro-1-methyl-6-chloro-7-fluoroisoquinolinyl)]-4,4-diphenylheptane hydrochloride;

7-[N-3-(4-fluorophenyl)propionyl]amino-1-[N-(1,2,3,4-tetrahydro-1-methyl-6,7-diacetoxy-isoquinolinyl)]-4,4-diphenylheptane hydrochloride;

7-[N-3-(4-fluorophenyl)propionyl]amino-1-[N-(1,2,3,4-tetrahydro-1-methyl-6-bromo-7-methoxyisoquinolinyl)]-4,4-diphenylheptane hydrochloride;

7-[N-3-(4-fluorophenyl)propionyl]amino-1-[N-(1,2,3,4-tetrahydro-1-methyl-6-fluoro-7-methoxyisoquinolinyl)]-4,4-diphenylheptane hydrochloride;

7-[N-3-(4-fluorophenyl)propionyl]amino-1-[N-(1,2,3,4-tetrahydro-1-methyl-6-methoxy-7-bromo-isoquinolinyl)]-4,4-diphenylheptane hydrochloride;

7-[N-3-(4-fluorophenyl)propionyl]amino-1-[N-(1,2,3,4-tetrahydro-1,6-dimethyl-7-methoxy-isoquinolinyl)]-4,4-diphenylheptane hydrochloride;

7-[N-3-(4-fluorophenyl)propionyl]amino-1-[N-(1,2,3,4-tetrahydro-1-methyl-6-carbo-methoxy-7-methoxyisoquinolinyl)]-4,4-diphenylheptane hydrochloride;

7-[N-3-(4-fluorophenyl)propionyl]amino-1-[N-(1,2,3,4-tetrahydro-1-cyclobutyl-6-bromo-7-methoxy-isoquinolinyl)]-4,4-diphenylheptane hydrochloride;

7-[N-3-(4-fluorophenyl)propionyl]amino-1-[N-(1,2,3,4-tetrahydro-1,3-dimethyl-6,7-di-methoxyisoquinolinyl)]-4,4-diphenylheptane hydrochloride;

7-[N-3-(4-fluorophenyl)propionyl]amino-1-[N-(1,2,3,4-tetrahydro-3-methyl-6,7-dimethoxy-isoquinolinyl)]-4,4-diphenylheptane hydrochloride;

7-[N-3-(4-fluorophenyl)propionyl]amino-1-[N-(1,2,3,4-tetrahydro-1,1-dimethyl-6,7-di-methoxyisoquinolinyl)]-4,4-diphenylheptane hydrochloride;

7-[N-3-(4-fluorophenyl)propionyl]amino-1-[N-(1,2,3,4-tetrahydro-1 ,3-dimethyl-7-methoxy-isoquinolinyl)]-4,4-diphenylheptane hydrochloride;

7-[N-3-(4-fluorophenyl)propionyl]-1-[N-(2,3,4,5-tetrahydro-1-methyl-7,8-dimethoxy-1H-2-benzazepinyl)]-4,4-diphenylheptane hydrochloride;

6-[N-3-(4-fluorophenyl)propionyl]amino-1-[N-(1,2,3,4-tetrahydro-1-methyl-6,7-methoxy-isoquinolinyl)]-3,3-diphenylhexane hydrochloride;

8-[N-3-(4-fluorophenyl)propionyl]amino-1-[N-(1,2,3,4-tetrahydro-1-methyl-6,7-dimethoxy-isoquinolinyl)]-5,5-diphenyloctane hydrochloride;

8-[N-3-(4-fluorophenyl)acetyl]amino-1-[N-(1,2,3,4-tetrahydro-1-methyl-6,7-dimethoxy-isoquinolinyl)]-5,5-diphenyloctane hydrochloride;

7-[N-3-(4-fluorophenyl)propionyl]amino-1-[N-(1,2,3,4-tetrahydro-1-methyl-7-methoxy-3-methoxycarbonylisoquinolinyl)]-4,4-diphenylheptane hydrochloride;

7-[N-3-(4-fluorophenyl)propionyl]amino-1-[N-(1,2,3,4-tetrahydro-3-(2-hydroxyethyl-aminocarbonyl)-1-methyl-7-methoxyisoquinolinyl)]-4,4-diphenylheptane hydrochloride;

7-[N-3-(4-fluorophenyl)propionyl]amino-1-[N-(1,2,3,4-tetrahydro-(3-hydroxypropyl-aminocarbonyl)-1-methyl-7-methoxyisoquinolinyl)]-4,4-diphenylheptane hydrochloride;

7-[N-3-(4-fluorophenyl)propionyl]amino-1-[N-(1,2,3,4-tetrahydro-3-(4-hydroxybutyl-aminocarbonyl)-1-methyl-7-methoxyisoquinolinyl)]-4,4-diphenylheptane hydrochloride;

7-[N-3-(4-fluorophenyl)propionyl]amino-1-[N-(1,2,3,4-tetrahydro-1-methyl-7-methoxy-3-(2-( N-pyrrolidinyl)ethylaminocarbonyl)isoquinolinyl)]-4,4-diphenylheptane hydrochloride;

7-[N-3-(4-fluorophenyl)propionyl]amino-1-[N-(1,2,3,4-tetrahydro-1-methyl-3-hydroxy-methyl-7-methoxyisoquinolinyl)]-4,4-diphenylheptane hydrochloride;

7-[N-3-(phenyl)propionyl]amino-1-[N-(1,2,3,4-tetrahydro-1-methyl-6,7-dimethoxy-isoquinolinyl)]-4,4-diphenylheptane hydrochloride;

7-[N-3-(3,4-dichlorophenyl)propionyl]amino-1-[N-(1,2,3,4-tetrahydro-1-methyl-6,7-dimethoxyisoquinolinyl)]-4,4-diphenylheptane hydrochloride;

7-[N-3-(3,4-difluorophenyl)propionyl]amino-1-[N-(1,2,3,4-tetrahydro-1-methyl-6,7-dimethoxyisoquinolinyl)]-4,4-diphenylheptane hydrochloride;

7-[N-3-(3-fluoro-4-chloro-phenyl)propionyl]amino-1-[N-(1,2,3,4-tetrahydro-1-methyl-6,7-dimethoxy-isoquinolinyl)]-4,4-diphenylheptane hydrochloride;

7-[N-3-(4-fluoro-3-chloro-phenyl)propionyl]amino-1-[N-(1,2,3,4-tetrahydro-1-methyl-6,7-dimethoxy-isoquinolinyl)]-4,4-diphenylheptane hydrochloride;

7-[N-3-(3,4-dimethoxyphenyl)propionyl]amino-1-[N-(1,2,3,4-tetrahydro-1-methyl-6,7-dimethoxyisoquinolinyl)]-4,4-diphenylheptane hydrochloride;

7-[N-3-(4-methoxyphenyl)propionyl]amino-1-[N-(1,2,3,4-tetrahydro-1-methyl-6,7-dimethoxyisoquinolinyl)]-4,4-diphenylheptane hydrochloride;

7-[N-3-(4-chlorophenyl)propionyl]amino-1-[N-(1,2,3,4-tetrahydro-1-methyl-6,7-dimethoxy-isoquinolinyl)]-4,4-diphenylheptane hydrochloride;

7-[N-3-(4-fluorophenyl)acetyl]amino-1-[N-(1,2,3,4-tetrahydro-1-methyl-6,7-dimethoxy-isoquinolinyl)]-4,4-diphenylheptane hydrochloride;

7-[N-3-(4-fluorophenyl)propionyl]amino-1-[N-(1,2,3,4-tetrahydro-1-(3-N-phthalimido-propyl)-6,7-dimethoxyisoquinolinyl)]-4,4-diphenylheptane hydrochloride;

7-[N-3-(4-fluorophenyl)propionyl]amino-1-[N-(1,2,3,4-tetrahydro-1-(3-aminopropyl)-6,7-dimethoxyisoquinolinyl)]-4,4-diphenylheptane hydrochloride, 7-[N-3-(4-fluorophenyl)propionyl]amino-1-[N-(1,2,3,4-tetrahydro-1-[3-N-(biscyclobutyl-amino)propyl]-6,7-dimethoxyisoquinolinyl)]-4,4-diphenylheptane dihydrochloride;

7-[N-3-(4-fluorophenyl)propionyl]amino-1-[N-(1,2,3,4-tetrahydro-1-[3-N-(biscyclopropyl-mmethlamino)propyl]-6,7-dimethoxyisoquinotinyl)]-4,4-diphenmlheptane dihydrochloride;

7-[N-3-(4-fluorophenyl)propionyl]amino-1-[N-(1,2,3,4-tetrahydro-1-[3-N-(dimethylamino)-propyl]-6,7-dimethoxyisoquinolinyl)]-4,4-diphenylheptane dihydrochloride;

7-[N-3-(4-fluorophenyl)propionyl]amino 1-[N-(1,2,3,4-tetrahydro-1-[3-N-(isopropyl)propyl]-6,7-dimethoxyisoquinolinyl)]-4,4-diphenylheptane dihydrochloride;

7-[N-3-(4-fluorophenyl)propionyl]amino-1-[N-(1,2,3,4-tetrahydro-1-(5-N-phthalimido-pentyl)-6,7-dimethoxyisoquinolinyl)]-4,4-diphenylheptane hydrochloride:

7-[N-3-(4-fluorophenyl)propionyl]amino-1-[N-(1,2,3,4-tetrahydro-1-(5-aminopentyl)-6,7-dimethoxyisoquinolinyl)]-4,4-diphenylheptane dihydrochloride;

7-[N-3-(4-fluorophenyl)propionyl]amino-1-[N-(1,2,3,4-tetrahydro-1-[5-N-(biscyclobutyl-amino)pentyl]-6,7-dimethoxyisoquinolinyl)]-4,4-diphenylheptane dihydrochloride;

7-[N-3-(4-fluorophenyl)propionyl]amino 1-[N-(1,2,3,4-tetrahydro-1-[5-N-(biscyclopropyl-methylamino)pentyl]-6,7-dimethoxyisoquinolinyl)]-4,4-diphenylheptane dihydrochloride;

7-[N-3-(4-fluorophenyl)propionyl]amino-1-[N-(1,2,3,4-tetrahydro-1-[5-N-(dimethylamino)-pentyl]-6,7-dimethoxyisoquinolinyl)]-4,4-diphenylheptane dihydrochloride;

7-[N-3-(4-fluorophenyl)propionyl]amino-1-[N-(1,2,3,4-tetrahydro-1-[5-N-(isopropylamino)-pentyl]-6,7-dimethoxyisoquinolinyl)]-4,4-diphenylheptane dihydrochloride;

7-[N-3-(4-fluorophenyl)propionyl]amino-1-[N-(1,2,3,4-tetrahydro-1-cyclobutyl-6-fluoro-7-methoxyisoquinolinyl)]-4,4-diphenylheptane hydrochloride;

7-[N-3-(4-fluorophenyl)propionyl]amino-1-[N-(1,2,3,4-tetrahydro-1-(4-N-phthalimidobutyl)-6-methyl-7-methoxyisoquinolinyl)]-4,4-diphenylheptane hydrochloride;

7-[N-3-(4-fluorophenyl)propionyl]amino-1-[N-(1,2,3,4-tetrahydro-1-(4-aminobutyl)-6-methyl-7-methoxyisoquinolinyl)]-4,4-diphenylheptane dihydrochloride;

7-[N-3-(4-fluorophenyl)propionyl]amino-1-[N-(1,2,3,4-tetrahydro-1-(4-N-isopropylamino-butyl)-6-methyl-7-methoxyisoquinolinyl)]-4,4-diphenylheptane dihydrochloride; and 7-[N-3-(4-fluorophenyl)propionyl]amino-1-[N-(1,2,3,4-tetrahydro-1-cyclobutyl-6-methyl-7-methoxyisoquinolinyl)]-4,4-diphenylheptane hydrochloride.

9. A process of preparing a compound of formula:

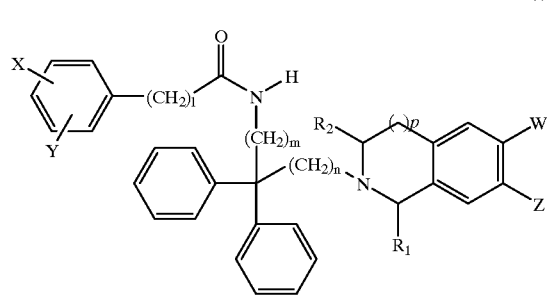

(I)

or a pharmaceutically acceptable salt, ester, or prodrug thereof, wherein:

l, m, and n are each independently 1, 2, 3, or 4;

p is 1 or 2.

$R_1$ is selected from the group consisting of:
(a) alkyl,
(b) cycloalkyl,
(c) aryl,
(d) cyano,
(e) —$(CH_2)$, —$R_4$ wherein q is 0 to 10,
(f) -cycloalkyl-$R_5$, and
(g) -aryl-$R_5$.

$R_2$ is selected from the group consisting of:
(a) alkyl,
(b) hydrogen,
(c) alkoxucarbonyl,
(d) hydroxymethyl, and (e) —(CH$_2$)$_q$—R$_4$, wherein q is 0 to 10;

R$_4$ is selected from the group consisting of:
(a) alkyl,
(b) alkoxy,
(c) aryl,
(d) aryloxy,
(e) cyano,
(f) cycloalkyl,
(g) hydroxy,
(h) halogen,
(i) phthalimido,
(j) -cycloalkyl-R$_5$,
(k) -aryl-R$_5$; and
(l) —NR$_6$R$_7$;

R$_5$ is selected from the group consisting of:
(a) alkyl,
(b) alkoxy,
(c) cyano,
(d) hydroxy,
(e) halogen,
(f) trifluoromethyl, and
(g) —(CH$_2$)$_q$NR$_6$R$_2$, wherein g is 0 to 10;

R$_6$ and R$_7$ are independently selected from the group consisting of:
(a) hydrogen,
(b) alkyl,
(c) cycloalkyl, and
(d) aryl, or R$_6$ is hydrogen and R$_7$ is a group of the formula —COR( wherein Rg is selected from the group consisting of:
(a) alkyl,
(b) aryl, and
(c) heterocycle;

X and Y are independently selected from the prouD consisting of:
(a) hydrogen,
(b) halogen,
(c) alkoxy,
(d) alkyl, and
(e) trifluoromethyl; and W and Z are independently selected from the group consisting of:
(a) hydrogen,
(b) hydroxy,
(c) alkyl,
(d) alkoxy,
(e) alkoxycarbonyl,
(f) nitro,
(g) N-acyl,
(h) halogen, and
(i) trifluoromethyl, or W and Z taken together form a cyclic ring; comnrising the steps of:
(a) treating a diphenyl-substituted aminoalkanol of the formula:

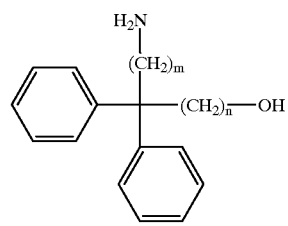

wherein m and n are as defined above, with an actuating reagent of the formula:

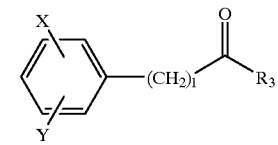

wherein l, X, and Y are as defined above, and R$_3$ is selected from hydroxy, halo, or an aryl ring substituted with an electron withdrawing group, to obtain an N-substituted aminoalkanol;
(b) oxidizing alcohol moiety of the N-substituted aminoalkanol to an aidehyde moiety; and
(c) alkylating the aldehyde moiety with an isoquinoline ring of the formula:

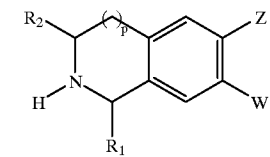

wherein p, R$_1$, R$_2$, W and Z are as defined above.

10. A compound according to claim 9, wherein R$_1$ is selected from the group consisting of alkyl, cycloalkyl, and —(CH$_2$)$_q$—R$_4$, wherein q is 0 to 10, and R$_4$ is a group of the formula —NR$_6$R$_7$, wherein R$_6$ and R$_7$ are each independently selected from hydrogen, alkyl, and cycloalkyl.

11. A compound according to claim 9, wherein X and Y are independently selected from the group consisting of hydrogen and halogen.

12. A compound according to claim 11, wherein the acylating reagent is 3-(4-fluorophenyl)propionic acid.

13. A process of preparing a compound of formula:

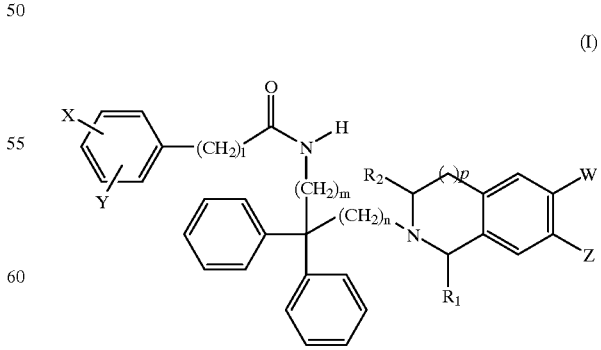

(I)

or a pharmaceutically acceptable salt, ester, or prodrug thereof, wherein:

l, m, and n are each independently 1, 2, 3, or 4;

p is 1 or 2;
R₁ is selected from the group consisting of:
  (a) alkyl,
  (b) cycloalkyl,
  (c) aryl,
  (d) cyano,
  (e) —(CH₂)$_q$—R₄, wherein g is 0 to 10,
  (f) -cycloalkyl-R₅, and
  (g) -aryl-R₅;
R₂ is selected from die group consisting of:
  (a) alkyl,
  (b) hydrogen,
  (c) alkoxycarbonyl,
  (d) hydroxymethyl, and
  (e) —(CH₂)$_q$—R₄, wherein a is 0 to 10;
R₄ is selected from the group consisting of:
  (a) alkyl,
  (b) alkoxy,
  (c) aryl,
  (d) aryloxy,
  (e) cyano,
  (f) cycloalkyl,
  (h) halogen,
  (i) phthalimido,
  (j) -cycloalkyl-R₅,
  (k) -aryl-R₅, and
R₅ is selected from the group consisting of:
  (a) alkyl,
  (b) alkoxy,
  (c) cyano,
  (d) hydroxy,
  (e) halogen,
  (f) trifluoromethyl, and
  (g) —(CH₂)—NR₆R₇, wherein g is 0 to 10;
R₆ and R₇ are independently selected from the group consisting of:
  (a) hydrogen,
  (b) alkyl,
  (c) cycloalkyl, and
  (d) aryl, or
R₆ is hydrogen and R₇ is a group of the formula —COR₈, wherein R₈ is selected from the group consisting of:
  (a) alkyl,
  (b) aryl, and
  (c) heterocycle;
X and Y are independently selected from the group consisting of:
  (a) hydrogen,
  (b) halogen,
  (c) alkoxy,
  (d) alkyl, and
  (e) trifluoromethyl; and
W and Z are independently selected from the group consisting of:
  (a) hydrogen,
  (b) hydroxy,
  (c) alkyl,
  (d) alkoxy,
  (e) alkoxycarbonyl,
  (f) nitro,
  (g) N-acyl,
  (h) halogen, and
  (i) trifluoromethyl, or
W and Z taken together form a cyclic ring; comprising the steps of:
  (a) treating a diphenyl-substituted aminoalkanol of the formula:

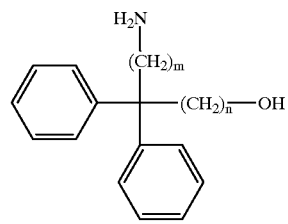

wherein m and n are as defined above, with an acylating reagent of the formula:

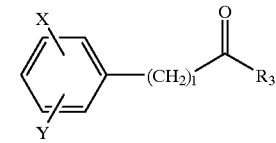

wherein l, X and Y are defined above, and R₃ is selected from hydroxy, halo, or an aryl ring substituted with an electron withdrawing group, to obtain an N-substituted aminoalkanol;

(b) preparing a reactive leaving group from the alcohol moiety of the N-substituted aminoalkanol to obtain a compound of the formula:

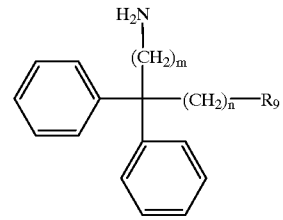

wherein R₉ is selected from the group consisting of halide and mesylate; and (c) alkylating the reactive N-substituted aminoalkanol with an isoquinoline ring of the formula:

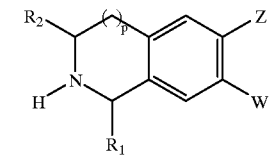

or the hydroiodide salt thereof, wherein p, R₁, R₂, W and Z are as defined above.

14. A compound according to claim 13, wherein R₁ is selected from the group consisting of alkyl, cycloalkyl, and —(CH₂)$_q$—R₄, wherein q is 0 to 10, and R₄ is a group of the formula —NR₆R₇, wherein R₆ and R₇ are each independently selected from hydrogen, alkyl, and cycloalkyl.

15. A compound according to claim 13, wherein X and Y are independently selected from the group consisting of hydrogen and halogen.

16. A compound according to claim 13, wherein the acylating reagent is 3-(4-fluorophenyl)propionic acid.

17. A pharmaceutical composition for inhibiting the release of luteinizing hormone comprising a therapeutically effective amount of a compound according to claim 1 and a pharmaceutically acceptable carrier.

18. A pharmaceutical composition for inhibiting the release of luteinizing hormone comprising a therapeutically effective amount of a compound according to claim 8 and a pharmaceutically acceptable carrier.

19. A method of modulating luteinizing hormone release in humans and other mammals in need of such treatment comprising administering to a patient in need thereof, a therapeutically effective amount of a compound according to claim 1.

20. A method of modulating luteinizing hormone release in humans and other mammals in need of such treatment comprising administering, to a patient in need thereof, a therapeutically effective amount of a compound according to claim 8.

* * * * *

UNITED STATES PATENT AND TRADEMARK OFFICE
CERTIFICATE OF CORRECTION

PATENT NO. : 5,981,521
DATED : November 9, 1999
INVENTOR(S) : Fortuna Haviv et al It is certified that error appears in the above-indentified patent and that said Letters Patent is hereby corrected as shown below:

On title page, item 75 Inventors
replace "Evanston"
with --North Chicago--.

On title page, item 75 Inventors
replace "Lawrenceville;"
with --Grayslake;--.

UNITED STATES PATENT AND TRADEMARK OFFICE
CERTIFICATE OF CORRECTION

PATENT NO. : 5,981,521
DATED : November 9, 1999
INVENTOR(S) : Fortuna Haviv et al It is certified that error appears in the above-indentified patent and that said Letters Patent is hereby corrected as shown below:

Col. 97, line 31
 replace "alkydl"
 with --alkyl--.

Col. 97, line 35
 replace "(CH2)-R4"
 with --(CH2)q-R4--.

Col. 100, line 40
 replace "(N-acetyl-10 amino)"
 with --(N-acetyl-amino)--.

Col. 100, line 56
 replace "arino"
 with --amino--.

Col. 100, line 61
 replace "phyhalimido-20"
 with --phthalimido-methyl--.

Col. 101, line 6
 replace "cyclobutylamino-mthy,,l"
 with --cyclobutylamino-methyl--.

Col. 101, line 12
 replace "dihydrochloride"
 with --diphenylheptane dihydrochloride--.

Col. 101, line 21
 replace "dimethoxyisoquiolinyt"
 with --dimethoxyisoquinolinyl--.

UNITED STATES PATENT AND TRADEMARK OFFICE
CERTIFICATE OF CORRECTION

PATENT NO. : 5,981,521
DATED : November 9, 1999
INVENTOR(S) : Fortuna Haviv et al It is certified that error appears in the above-indentified patent and that said Letters Patent is hereby corrected as shown below:

Col. 103, line 44
      replace "biscyclopropyl-mmethlamino"
      with --biscyclopropyl-methylamino--.

Col. 103, line 45
      replace "dimethoxyisoquinotinyl"
      with --dimethoxyisoquinolinyl--.

Col. 103, line 47
      replace "diphenmlheptane"
      with --diphenylheptane--.

Col. 103, line 51
      replace "amino 1"
      with --amino-1--.

Col. 104, line 54
      replace "2."
      with --2;--.

Col. 104, line 60
      replace "(CH2)"
      with --(CH2)q--.

Col. 104, line 66
      replace "alkoxucarbonyl"
      with --alkoxycarbonyl--.

Col. 105, line 27
      replace "(CH2)q-NR6R7 ,wherein g is 0 to 10;"
      with --(CH2)q-NR6R7, wherein Q is 0 to 10--.

UNITED STATES PATENT AND TRADEMARK OFFICE
CERTIFICATE OF CORRECTION

PATENT NO. : 5,981,521
DATED : November 9, 1999
INVENTOR(S) : Fortuna Haviv et al It is certified that error appears in the above-indentified patent and that said Letters Patent is hereby corrected as shown below:

Col. 105, line 36
     replace "COR("
     with --COR8--.
    Col. 105, line 37
     replace "Rg"
     with --R8--.
    Col. 105, line 42
     replace "prouD"
     with --group--.
    Col. 105, line 63
     replace "comnrising"
     with --comprising--.
    Col. 106, line 12
     replace "actuating"
     with --acylating--.
    Col. 106, line 22
     replace "arc as defined"
     with --are as defined--.
    Col. 107, line 10
     replace "die"
     with --the--.

UNITED STATES PATENT AND TRADEMARK OFFICE
CERTIFICATE OF CORRECTION

PATENT NO. : 5,981,521
DATED : November 9, 1999
INVENTOR(S) : Fortuna Haviv et al It is certified that error appears in the above-indentified patent and that said Letters Patent is hereby corrected as shown below:

Col. 107, line 22
 replace " "
 with --(g) hydroxy--.

Col. 107, line 25
 replace " (i) cycloalkyl-R5 "
 with --(j) cycloalkyl-R5--.

Col. 107, line 27
 replace " "
 with --(l) NR6R7;--.

Col. 107, line 34
 replace "(CH2)-NR6R7, wherein g is 0 to 10;"
 with --(CH2)q-NR6R7, wherein q is 0 to 10;--.

Col. 109, line 7
 replace "administering"
 with --administering,--.

Signed and Sealed this

Thirteenth Day of March, 2001

Attest:

NICHOLAS P. GODICI

*Attesting Officer*   *Acting Director of the United States Patent and Trademark Office*